United States Patent [19]

Glorioso et al.

[11] Patent Number: 5,858,355
[45] Date of Patent: Jan. 12, 1999

[54] IRAP GENE AS TREATMENT FOR ARTHRITIS

[75] Inventors: Joseph C. Glorioso, Cheswick; Christopher H. Evans; Paul D. Robbins, both of Pittsburgh, all of Pa.

[73] Assignee: University of Pittsburgh of the Commonwealth System of Higher Education, Pittsburgh, Pa.

[21] Appl. No.: 381,603

[22] Filed: Jan. 27, 1995

Related U.S. Application Data

[63] Continuation-in-part of Ser. No. 27,750, Mar. 8, 1993, abandoned, and a continuation-in-part of Ser. No. 183,563, Jan. 18, 1994, abandoned, which is a continuation of Ser. No. 963,928, Oct. 20, 1992, abandoned, which is a continuation of Ser. No. 630,981, Dec. 20, 1990, abandoned.

[51] Int. Cl.$^6$ ............................ A61K 48/00; C12N 15/00
[52] U.S. Cl. ...................... 424/93.21; 424/93.2; 514/44; 935/62
[58] Field of Search .......................... 514/44; 424/93.21, 424/93.6, 93.2; 935/62

[56] References Cited

U.S. PATENT DOCUMENTS

| | | | |
|---|---|---|---|
| 4,396,601 | 8/1983 | Salser et al. | 424/94 |
| 4,766,069 | 8/1988 | Auron et al. | 435/70 |
| 4,778,806 | 10/1988 | Bender et al. | 514/336 |
| 4,780,470 | 10/1988 | Bender et al. | 514/341 |
| 4,794,114 | 12/1988 | Bender et al. | 514/333 |
| 4,816,436 | 3/1989 | Jacobs | 514/2 |
| 4,870,101 | 9/1989 | Ku et al. | 514/476 |
| 4,935,343 | 6/1990 | Allison et al. | 435/7 |
| 4,968,607 | 11/1990 | Dower et al. | 435/69.1 |
| 5,081,228 | 1/1992 | Dower et al. | 530/35.1 |
| 5,180,812 | 1/1993 | Dower et al. | 530/351 |

FOREIGN PATENT DOCUMENTS 9211359  7/1992  WIPO .

OTHER PUBLICATIONS

Aston and Bentley, "Repair of Articular Surfaces by Allografts of Articular and Growth–Plate Cartilage", *The Journal of Bone and Joint Surgery*, vol. 68 B, No. 1, pp. 29–35 (Jan. 1986).
Pettipher et al., "Interleukin 1 Induces Leukocyte Infiltration and Cartilage Proteoglycan Degradation in the Synovial Joint", *Proc. Natl. Acad. Sci. USA*, vol. 83, pp. 8749–8753 (Nov. 1986).
Korman et al., "Expression of Human Class II Major Histocompatibility Complex Antigens Using Retrovirus Vectors", *Proc. Natl. Acad. Sci. USA*, vol. 84, pp. 2150–2154 (Apr. 1987).
Banerjee et al., "Immunosuppression of Collagen–Induced Arthritis in Mice with an Anti–IL–2 Receptor Antibody", *The Journal of Immunology*, vol. 141, No. 4, pp. 1150–1154 (Aug. 1988).
Danos et al., "Safe and Efficient Generation of Recombinant Retroviruses with Amphotropic and Ecotropic Host Ranges", *Proc. Natl. Acad. Sci. USA*, vol. 85, pp. 6460–6464 (Sep. 1988).
Rosenberg et al., "Grafting Genetically Modified Cells to the Damaged Brain: Restorative Effects of NGF Expression", *Science*, vol. 242, pp. 1575–1578 (Dec. 1988).
Grande et al., "The Repair of Experimentally Produced Defects in Rabbit Articular Cartilage by Autologous Chondrocyte Transplantation", *Journal of Orthopaedic Research*, vol. 7, No. 2, pp. 208–218 (1989).
Wakitani et al., "Repair of Rabbit Articular Surfaces with Allograft Chondrocytes Embedded in Collagen Gel", *The Journal of Bone and Joint Surgery*, vol. 71–B, No. 1, pp. 74–80 (Jan. 1989).
Chin et al., "Interleukin 1 Receptors on Rabbit Articular Chondrocytes: Relationship Between Biological Activity and Receptor Binding Kinetics", *The FASEB Journal*, vol. 4, pp. 1481–1487 (Mar. 1990).
Fanslow et al., "Regulation of Alloreactivity in Vivo by a Soluble Form of the Interleukin–1 Receptor", *Science*, vol. 248, pp. 739–742 (May 1990).
Gao et al., "A Novel Cationic Liposome Reagent for Efficient Transfection of Mammalian Cells", *Biochemical and Biophysical Research Communications*, vol. 179, No. 1, pp. 280–285 (Aug. 1991).
Bandara et al., "Intraarticular Expression of IRAP by Gene Transfer", *Arthritis Rheum.*, vol. 39 (suppl), S193, C161 (1992).
Evans, "Transferring Therapeutic Genes to Joints: A Pittsburgh Idea", *The Pittsburgh Orthopaedic Journal*, vol. 3, pp. 130–131 (1992).
Evans et al., "Gene Transfer to Joints for Arthritis Therapy", *J. Cell Biochem.*, 16F:V207 (1992).
Bandara et al., "Gene Transfer to Synoviocytes: Prospects for Gene Treatment of Arthritis", *DNA and Cell Biology*, vol. 11, No. 3, pp. 227–231 (1992).
Evans et al., "Synovial Cell Transplants for Gene Transfer to Joints", *Transplantation Proceedings*, vol. 24, No. 6, p. 2966 (Dec. 1992).
Bandara et al., "Gene Transfer to Synovium", Trans. Orthop. Res. Soc., 18, p. 242 (1993).

*Primary Examiner*—Deborah Crouch
*Attorney, Agent, or Firm*—Eckert Seamans Cherin & Mellott, LLC

[57] ABSTRACT

The subject invention concerns a method of introducing at least one gene encoding a product into at least one cell of a connective tissue of a mammalian host for use in treating the mammalian host including employing recombinant techniques to produce a DNA vector molecule which contains the gene encoding for the product and infecting the connective cell of the mammalian host using the DNA vector molecule using the gene coding for the product. A method is provided for introducing at least one gene encoding a product into at least one cell of a connective tissue of a mammalian host employing non-viral means. In a specific example, isolated synovial cells were infected with a retrovirus comprising a DNA sequence encoding IRAP and the transfected cells administered to an arthritic joint. A method to produce an animal model for the study of connective tissue pathology is also disclosed. Additionally, this invention provides a method of using in vivo a gene encoding and extracellular interleukin-1 binding domain of an interleukin-1 receptor.

7 Claims, 19 Drawing Sheets

IRAP GENE AS TREATMENT FOR ARTHRITIS

CROSS-REFERENCE TO RELATED APPLICATION

This is a continuation-in-part application of U.S. application Ser. No. 08/027,750, filed Mar. 8, 1993, now abandoned, and a continuation-in-part application of U.S. application Ser. No. 08/183,563, filed Jan. 18, 1994, now abandoned, which is a continuation application of U.S. application Ser. No. 07/963,928, filed Oct. 20, 1992, now abandoned, which was a continuation application of U.S. application Ser. No. 07/630,981, filed Dec. 20, 1990, now abandoned.

BACKGROUND OF THE INVENTION

1. Field of the Invention

The present invention relates to a method of introducing at least one gene encoding a product into at least one cell of a connective tissue of a mammalian host for use in treating the mammalian host. This method discloses employing DNA vector molecules containing a gene encoding the product and infecting the connective tissue cells of the mammalian host using the DNA vector molecule. This invention provides a method of introducing at least one gene encoding a product into at least one cell of a connective tissue of a mammalian host for use in treating the mammalian host including employing non-viral means for effecting such introduction.

The present invention discloses ex vivo and in vivo techniques for delivery of a DNA sequence of interest to the connective tissue cells of the mammalian host. The ex vivo technique involves prior removal and culture of target autologous connective tissue cells, in vitro infection of the DNA sequence, DNA vector or other delivery vehicle of interest into the connective tissue cells, followed by transplantation to the modified connective tissue cells to the target joint of the mammalian host, so as to effect in vivo expression of the gene product of interest. The in vivo technique bypasses the requirement for in vitro culture of target connective tissues cells; instead relying on direct transplantation of the DNA sequence, DNA vector or other delivery vehicle to the target in vivo connective tissue cells, thus effecting expression of the gene product of interest.

The present invention also relates to a method to produce an animal model for the study of connective tissue pathologies and systemic indices of inflammation.

The present invention further relates to a method of using a gene encoding a truncated interleukin-1 receptor to resist the deleterious pathological changes associated with arthritis. More specifically, this invention provides a method wherein a gene coding for an extracellular interleukin-1 binding domain of an interleukin-1 receptor is introduced into synovial cells of a mammalian host in vivo for neutralizing the destructive activity of interleukin-1 upon cartilage and other soft tissues. As an alternative, the patients own synovial cells are transduced in vitro and introduced back into the affected joint, using transplantation procedures such as for example, intra-articular injection.

As an alternative to the in vitro manipulation of synovia, the gene encoding the product of interest is introduced into liposomes and injected directly into the area of the joint, where the liposomes fuse with synovial cells, resulting in an in vivo gene transfer to synovial tissue. As an additional alternative to the in vitro manipulation of synovia, the gene encoding the product of interest is introduced into the area of the joint as naked DNA. The naked DNA enters the synovial cell, resulting in an in vivo gene transfer to synovial tissue.

As an another alternative, hematopoietic progenitor cells or the mature lymphoid or myeloid cells may be transfected in vitro, recovered and injected into the bone marrow of the patient using techniques known to the skilled artisan.

2. Brief Description of the Related Art

Arthritis involves inflammation of a joint that is usually accompanied by pain and frequently changes in structure. Arthritis may result from or be associated with a number of conditions including infection, immunological disturbances, trauma and degenerative joint diseases such as, for example, osteoarthritis. The biochemistry of cartilage degradation in joints and cellular changes have received considerable investigation.

In a healthy joint, cells in cartilage (chondrocytes) and the surrounding synovium (synoviocytes) are in a resting state. In this resting state, these cells secrete basal levels of prostaglandin $E_2$ and various neutral proteinases, such as, for example, collagenase, gelatinase and stromelysin, with the ability to degrade cartilage. During the development of an arthritic condition, these cells become activated. In the activated state, synoviocytes and chondrocytes synthesize and secrete large amounts of prostaglandin $E_2$ and neutral proteinases.

In efforts to identify pathophysiologically relevant cell activators, it has been known that the cytokine interleukin-1 activates chondrocytes and synoviocytes and induces cartilage breakdown in vitro and in vivo. Additionally, interleukin-1 is a growth factor for synoviocytes and promotes their synthesis of matrix, two properties suggesting the involvement of interleukin-1 in the synovial hypertrophy that accompanies arthritis. In contrast, interleukin-1 inhibits cartilaginous matrix synthesis by chondrocytes, thereby suppressing repair of cartilage. Interleukin-1 also induces bone resorption and thus may account for the loss of bone density seen in rheumatoid arthritis. Interleukin-1 is inflammatory, serves as a growth factor for lymphocytes, is a chemotactic factor and a possible activator of polymorphonuclear leukocytes (PMNs). When present in a sufficient concentration, interleukin-1 may cause fever, muscle wasting and sleepiness.

The major source of interleukin-1 in the joint is the synovium. Interleukin-1 is secreted by the resident synoviocytes, which are joined under inflammatory conditions by macrophages and other white blood cells.

Much attention has been devoted to the development of a class of agents identified as the "Non-Steroidal Anti-Inflammatory Drugs" (hereinafter "NSAIDs"). The NSAIDs inhibit cartilage synthesis and repair and control inflammation. The mechanism of action of the NSAIDs appears to be associated principally with the inhibition of prostaglandin synthesis in body tissues. Most of this development has involved the synthesis of better inhibitors of cyclo-oxygenase, a key enzyme that catalyzes the formation of prostaglandin precursors (endoperoxides) from arachidonic acid. The anti-inflammatory effect of the NSAIDs is thought to be due in part to inhibition of prostaglandin synthesis and release during inflammation. Prostaglandins are also believed to play a role in modulating the rate and extent of leukocyte infiltration during inflammation. The NSAIDs include, such as, for example, acetylsalicylic acid (aspirin), fenoprofen calcium (Nalfon® Pulvules®, Dista Products Company), ibuprofen (Motrin®, The Upjohn Company), and indomethacin (Indocin®, Merck, Sharp & Dohme).

In contrast, the studies upon which the present invention is based show that production of the various neutral proteinases with the ability to degrade cartilage occurs even if prostaglandin synthesis is completely blocked.

Therapeutic intervention in arthritis is hindered by the inability to target drugs, such as the NSAIDs, to specific areas within a mammalian host, such as, for example a joint. Traditional routes of drug delivery, such as for example, oral, intravenous or intramuscular administration, depend upon vascular perfusion of the synovium to carry the drug to the joint. This is inefficient because transynovial transfer of small molecules from the synovial capillaries to the joint space occurs generally by passive diffusion. This diffusion is less efficient with increased size of the target molecule. Thus, the access of large drug molecules, for example, proteins, to the joint space is substantially restricted. Intra-articular injection of drugs circumvents those limitations; however, the half-life of drugs administered intra-articularly is generally short. Another disadvantage of intra-articular injection of drugs is that frequent repeated injections are necessary to obtain acceptable drug levels at the joint spaces for treating a chronic condition such as, for example, arthritis. Because therapeutic agents heretofore could not be selectively targeted to joints, it was necessary to expose the mammalian host to systemically high concentrations of drugs in order to achieve a sustained, intra-articular therapeutic dose. Exposure of non-target organs in this manner exacerbated the tendency of anti-arthritis drugs to produce serious side effects, such as for example, gastrointestinal upset and changes in the hematological, cardiovascular, hepatic and renal systems of the mammalian host.

It has been shown that genetic material can be introduced into mammalian cells by chemical or biologic means. Moreover, the introduced genetic material can be expressed so that high levels of a specific protein can be synthesized by the host cell. Cells retaining the introduced genetic material may include an antibiotic resistance gene thus providing a selectable marker for preferential growth of the transduced cell in the presence of the corresponding antibiotic. Chemical compounds for inhibiting the production of interleukin-1 are also known.

U.S. Pat. No. 4,778,806 discloses a method of inhibiting the production of interleukin-1 by monocytes and/or macrophages in a human by administering through the parenteral route a 2-2'-[1,3-propan-2-onediyl-bis (thio)]bis-1 H-imidazole or a pharmaceutically acceptable salt thereof. This patent discloses a chemical compound for inhibiting the production of interleukin-1. By contrast, in one embodiment of the present invention, gene therapy is employed that is capable of binding to and neutralizing interleukin-1.

U.S. Pat. No. 4,780,470discloses a method of inhibiting the production of interleukin-1 by monocytes in a human by administering a 4,5-diaryl-2 (substituted) imidazole. This patent also discloses a chemical compound for inhibiting the production of interleukin-1.

U.S. Pat. No. 4,794,114 discloses a method of inhibiting the 5-lipoxygenase pathway in a human by administering a diaryl-substituted imidazole fused to a thiazole, pyrrolidine or piperidine ring or a pharmaceutically acceptable salt thereof. This patent also discloses a chemical compound for inhibiting the production of interleukin-1.

U.S. Pat. No. 4,870,101 discloses a method for inhibiting the release of interleukin-1 and for alleviating interleukin-1 mediated conditions by administering an effective amount of a pharmaceutically acceptable anti-oxidant compound such as disulfiram, tetrakis [3-(2,6-di-tert-butyl-4-hydroxyphenyl)propionyloxy methyl]methane or 2,4-di-isobutyl-6-(N,N-dimethylamino methyl)-phenol. This patent discloses a chemical compound for inhibiting the release of interleukin-1.

U.S. Pat. No. 4,816,436 discloses a process for the use of interleukin-1 as an anti-arthritic agent. This patent states that interleukin-1, in association with a pharmaceutical carrier, may be administered by intra-articular injection for the treatment of arthritis or inflammation. In contrast, the present invention discloses a method of using and preparing a gene that is capable of binding to and neutralizing interleukin-1 as a method of resisting arthritis.

U.S. Pat. No. 4,935,343 discloses an immunoassay method for the detection of interleukin-1 beta that employs a monoclonal antibody that binds to interleukin-1 beta but does not bind to interleukin-1 alpha. This patent discloses that the monoclonal antibody binds to interleukin-1 beta and blocks the binding of interleukin-1 beta to interleukin-1 receptors, and thus blocking the biological activity of interleukin-1 beta. The monoclonal antibody disclosed in this patent may be obtained by production of an immunogen through genetic engineering using recombinant DNA technology. The immunogen is injected into a mouse and thereafter spleen cells of the mouse are immortalized by fusing the spleen cells with myeloma cells. The resulting cells include the hybrid continuous cell lines (hybridomas) that may be later screened for monoclonal antibodies. This patent states that the monoclonal antibodies of the invention may be used therapeutically, such as for example, in the immunization of a patient, or the monoclonal antibodies may be bound to a toxin to form an immunotoxin or to a radioactive material or drug to form a radio pharmaceutical or pharmaceutical.

U.S. Pat. No. 4,766,069 discloses a recombinant DNA cloning vehicle having a DNA sequence comprising the human interleukin-1 gene DNA sequence. This patent provides a process for preparing human interleukin-1 beta, and recovering the human interleukin-1 beta. This patent discloses use of interleukin-1 as an immunological reagent in humans because of its ability to stimulate T-cells and B-cells and increase immunoglobulin synthesis.

U.S. Pat. No. 4,396,601 discloses a method for providing mammalian hosts with additional genetic capability. This patent provides that host cells capable of regeneration are removed from the host and treated with genetic material including at least one marker which allows for selective advantage for the host cells in which the genetic material is capable of expression and replication. This patent states that the modified host cells are then returned to the host under regenerative conditions. In the present invention, genetic material may be directly introduced (a) into host cells in vivo or (b) into synoviocytes in vitro for subsequent transplantation back into the patient's joints.

U.S. Pat. No. 4,968,607 discloses a DNA sequence encoding a mammalian interlelukin-1 receptor protein which exhibits interleukin-1 binding activity.

U.S. Pat. No. 5,081,228 discloses a DNA sequence encoding both the murine and human interleukin-1 receptor. This patent also provides a process for the in vitro expression of said DNA sequences.

U.S. Pat. No. 5,180,812 discloses a substantially pure preparation of the human interlelukin-1 receptor protein.

In spite of these prior art disclosures, there remains a very real and substantial need for a method of introducing at least one gene encoding a product into at least one cell of a connective tissue of a mammalian host in vitro, or alternatively in vivo, for use in treating the mammalian host. Further, there is a need for a process wherein a gene encoding a truncated interleukin-1 receptor is used to resist the deleterious pathological changes associated with arthritis. More specifically there is a need for such a process where a gene coding for the extracellular interlelukin-1 binding domain of the interleukin-1 receptor, capable of binding to and neutralizing interlelukin-1 is expressed in host synovial cells in vivo. There is also a need to utilize one or more additional DNA sequences for delivery to and expression of a protein or protein fragment within a target host connective tissue cell, such as a synovial cell, so as to effect a treatment of various joint pathologies and concomitant systemic indices of inflammation.

SUMMARY OF THE INVENTION

The present invention has met the hereinbefore described need. A method of introducing at least one gene encoding a product into at least one cell of a connective tissue of a mammalian host for use in treating the mammalian host is provided for in the present invention. This method includes employing recombinant techniques to produce a DNA vector molecule containing the gene encoding for the product and infecting the connective tissue cell of the mammalian host using the DNA vector molecule containing the gene coding for the product. The DNA vector molecule can be any DNA molecule capable of being delivered and maintained within the target cell or tissue such that the gene encoding the product of interest can be stably expressed. The DNA vector molecule preferably utilized in the present invention is either a viral DNA vector molecule or a plasmid DNA viral molecule. This method preferably includes introducing the gene encoding the product into the cell of the mammalian connective tissue for a therapeutic use.

One ex vivo method of treating a connective tissue disorder disclosed throughout this specification comprises initially generating a recombinant viral vector which contains a DNA sequence encoding a protein or biologically active fragment thereof. This recombinant viral vector is then used to infect a population of in vitro cultured connective tissue cells, resulting in a population of transfected connective cells. These transfected connective tissue cell are then transplanted to a target joint space of a mammalian host, effecting subsequent expression of the protein or protein fragment within the joint space. Expression of this DNA sequence of interest is useful in substantially reducing at least one deleterious joint pathology or indicia of inflammation normally associated with a connective tissue disorder.

The connective tissue cells are selected from the group of connective tissue consisting of a synovium, a cartilage, a tendon and a ligament, preferably synovial cells.

It is also preferred that a retroviral vector, such as MFG, be utilized as the viral vector.

Another preferred step in this ex vivo method is transplantation of transduced cells by by intraarticular injection.

It will be understood by the artisan of ordinary skill that the preferred source of cells for treating a human patient are the patients own cells, such as autologous synovial cells.

More specifically, this method includes employing as the gene a gene capable of encoding at least one of the materials which is selected from the group which includes (a) a human interlelukin-1 receptor antagonist protein or a biologically active derivative or fragment thereof, preferably MFG-IRAP, (b) a Lac Z marker gene capable of encoding a beta-galactosidase protein or a biologically active derivative or fragment thereof, (c) a soluble interleukin-1 receptor protein or a biologically active derivative or fragment thereof, (d) a soluble TNF-α receptor protein or a biologically active derivative or fragment thereof; (e) a proteinase inhibitor, and (f) a cytokine, and employing as the viral vector at least one vector which is selected from the group which includes (a) a retroviral vector including at least one of the materials selected from the group which includes MFG and BAG, (b) an adeno-associated virus, (c) an adenovirus, and (d) a herpes virus, including but not limited to herpes simplex 1 or herpes simplex 2.

A further embodiment of the present invention includes employing as the gene a gene capable of encoding at least one of the materials which is selected from the group which includes (a) a human interleukin-1 receptor antagonist protein or a biologically active derivative or fragment thereof, (b) a Lac Z marker gene capable of encoding a beta-galactosidase protein or a biologically active derivative or fragment thereof, (c) a soluble interleukin-1 receptor protein or a biologically active derivative or fragment thereof, (d) a soluble TNF-α receptor protein or a biologically active derivative or fragment thereof; (e) a proteinase inhibitor, and (f) a cytokine, and employing as the DNA plasmid vector any DNA plasmid vector known to one of ordinary skill in the art capable of stable maintenance within the targeted cell or tissue upon delivery, regardless of the method of delivery utilized. One such method is the direct delivery of the DNA vector molecule, whether it be a viral or plasmid DNA vector molecule, to the target cell or tissue. This method also includes employing as the gene a gene capable of encoding at least one of the materials selected from the group which includes (a) a human interleukin-1 receptor antagonist protein or biologically active derivative or fragment thereof, (b) a Lac Z marker gene capable of encoding a beta-galactosidase protein or biologically active derivative or fragment thereof, (c) a soluble interleukin-1 receptor protein or biologically active derivative or fragment thereof, (d) a soluble TNF-α receptor protein or a biologically active derivative or fragment thereof; (e) a proteinase inhibitor, and (f) a cytokine. In a specific method disclosed as an example, and not as a limitation to the present invention, a DNA plasmid vector containing the interleukin-1 beta (IL-1α) coding sequence was ligated downstream of the cytomegalovirus (CMV) promoter. This DNA plasmid construction was encapsulated within liposomes and injected intra-articularly into the knee joints of recipient rabbits. IL-1α was expressed and significant amounts of interleukin-1 beta was recovered from the synovial tissue. An alternative is injection of the naked plasmid DNA into the knee joint, allowing direct transfection of the DNA into the synovial tissue. Injection of IL-1α into the joint of a mammalian host allows for prolonged study of various joint pathologies and systemic indices of inflammation, as described within this specification.

Another embodiment of this invention provides a method for introducing at least one gene encoding a product into at least one cell of a connective tissue of a mammalian host for use in treating the mammalian host. This method includes employing non-viral means for introducing the gene encoding for the product into the connective tissue cell. More specifically, this method includes employing non-viral means which is selected from at least one of the group which includes (a) at least one liposome, (b) $Ca_3(PO_4)_2$, (c) electroporation, and (d) DEAE-dextran, and includes employing as the gene a gene capable of encoding at least one of the materials selected from the group which includes (a) a human interleukin-1 receptor antagonist protein or biologically active derivative or fragment thereof, (b) a Lac Z marker gene capable of encoding a beta-galactosidase protein or biologically active derivative or fragment thereof, (c) a soluble interleukin-1 receptor protein or biologically active derivative or fragment thereof, (d) a soluble TNF-α receptor protein or a biologically active derivative or fragment thereof; (e) a proteinase inhibitor, and (f) a cytokine.

A further embodiment of this invention provides an additional method for introducing at least one gene encoding a product into at least one cell of a connective tissue of a mammalian host for use in treating the mammalian host. This additional method includes employing the biologic means of utilizing a virus to deliver the DNA vector molecule to the target cell or tissue. Preferably, the virus is a psuedovirus, the genome having been altered such that the psuedovirus is capable only of delivery and stable maintenance within the target cell; but not retaining an ability to replicate within the target cell or tissue. The altered viral genome is further manipulated by recombinant DNA techniques such that the viral genome acts as a DNA vector molecule which contains the heterologous gene of interest to be expressed within the target cell or tissue. This method also includes employing as the gene a gene capable of encoding at least one of the materials selected from the group which includes (a) a human interleukin-1 receptor antagonist protein or biologically active derivative or fragment thereof, (b) a Lac Z marker gene capable of encoding a beta-galactosidase protein or biologically active derivative or fragment thereof, (c) a soluble interleukin-1 receptor protein or biologically active derivative or fragment thereof, (d) a soluble TNF-α receptor protein or a biologically active derivative or fragment thereof, (e) a proteinase inhibitor, and (f) a cytokine.

A further embodiment of this invention provides for an animal model to study connective tissue pathologies and indices of systemic inflammation. This model utilizes either ex vivo or in vivo delivery of at least one gene or DNA sequence of interest encoding a product into a least one cell of a connective tissue of a mammalian host. Examples of joint pathologies which can be studied in the present invention include, but are by no means limited to, joint pathologies such as leukocytosis, synovitis, cartilage breakdown and suppression of cartilage matrix synthesis. Examples of indices of systemic inflammation which include, but are by no means limited to, erythtocyte sedimentation rate, fever and weight loss.

An embodiment of the present invention is a method to produce an animal model for the study of joint pathologies. This embodiment comprises generating a recombinant viral vector which contains a DNA sequence encoding a protein or biologically active fragment thereof, infecting a population of in vitro cultured connective tissue cells with said recombinant viral vector, resulting in a population of transfected connective cells; and, transplanting said transfected connective cells to a joint space of a mammalian host, such that subsequent expression of said protein within said joint space substantially reduces at least one deleterious joint pathology or indicia of inflammation normally associated with a connective tissue disorder.

The connective tissue cells from this embodiment are also selected from the group of connective tissue consisting of a synovium, a cartilage, a tendon and a ligament, preferably synovial cells, including but not limited to autologous cells removed directly from the mammalian host of which the target joint resides.

As with other ex vivo based methods disclosed throughout this specification, a preferable method of transplantation of transduced connective cells, such as synovial cells, is by intraarticular injection.

A DNA sequence exemplified for animal model studies is a DNA sequence encoding human IL-1α or a biologically active fragment thereof.

Another DNA sequence exemplified for animal model studies is a DNA sequence encoding human tumor necrosis factor-α or a biologically active fragment thereof.

Another embodiment of a method to produce an animal model for the study of joint pathologies utilizes a recombinant DNA plasmid vector, which contains the DNA sequence of interest encoding a protein or biologically active fragment thereof. This recombinant DNA plasmid vector is used to transform a population of in vitro cultured connective tissue cells. The transformed connective cells, preferably synovial cells, are transplanted to a joint space of a mammalian host, so as to provide data regarding various joint pathologies and systemic indices of inflammation associated with connective tissue disorders.

This particular embodiment is exemplified by the ex vivo based delivery of MPG-IL-1α to a target rabbit knee joint, causing various joint pathologies and systemic indices of inflammations.

Another exemplification of this particular embodiment of the present invention is delivery of the CMV-IL-1α plasmid construction to the rabbit knee joint via liposome-mediated delivery.

An animal model as described and exemplified in this specification measures the ability of various gene therapy applications disclosed throughout this specification to withstand challenges from known causative agents (such as IL-1α) of joint pathologies and inflammatory side effects.

An additional embodiment of the present invention relates to a method of using a DNA sequence encoding a biologically active interleukin-1 receptor-antagonist (IRAP) or portion thereof for treatment of connective tissue joint pathologies. The DNA sequence encoding IRAP or a biologically active fragment thereof may be delivered to the connective tissue of a mammalian host by any combination of various vector strategies and transduction techniques disclosed throughout this specification.

A preferred method of the embodiment of delivering IRAP to a target joint space involves delivery of the IRAP gene to the synovial lining of a mammalian host through use of a retroviral vector with the ex vivo technique disclosed within this specification. In other words, a DNA sequence of interest encoding a functional IRAP protein or protein fragment is subcloned into a retroviral vector of choice, the recombinant viral vector is then grown to adequate titers and used to infect in vitro cultured synovial cells, and the transduced synovial cells, preferably autografted cells, are transplanted into the joint of interest, preferably by intraarticular injection.

Another preferred method of the present invention involves direct in vivo delivery of the IRAP gene to the synovial lining of a mammalian host through use of either an adenovirus vector, adeno-associated virus (AAV) vector or herpes-simples virus (HSV) vector. In other words, a DNA sequence of interest encoding a functional IRAP protein or protein fragment is subcloned into the respective viral vector, the IRAP containing viral vector is then grown to adequate titers and directed into the joint space, preferably by intra-articular injection. A retroviral-IRAP construct, such as MFG-IRAP may also be utilized to directly target previously inflamed connective tissue cells within the joint space.

Direct intra-articular injection of a DNA molecule containing the gene of interest into the joint results in transfection of the recipient synovial cells and hence bypasses the requirement of removal, in vitro culturing, transfection, selection, as well as transplanting the DNA vector containing—synoviocytes (as disclosed in the Example section) to promote stable expression of the heterologous gene of interest. Methods of presenting the DNA molecule to the target connective tissue of the joint includes, but is not limited to, encapsulation of the DNA molecule into cationic liposomes, subcloning the DNA sequence of interest in a retroviral vector as described throughout this specification, or the direct injection of the DNA molecule itself into the joint. The DNA molecule, regardless of the form of presentation to the knee joint, is preferably presented as a DNA vector molecule, either as recombinant viral DNA vector molecule or a recombinant DNA plasmid vector molecule. Expression of the heterologous gene of interest is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the synovial tissue. In vivo delivery of various viral and non-viral vectors to the rabbit knee joint are described in Example XIV.

Another embodiment of the present invention is delivery of a DNA sequence of interest to the connective tissue of a mammalian host by any of the methods disclosed within this specification so as to effect in vivo expression of the human TNF-α soluble receptor or a biologically active fragment thereof.

Another embodiment of the present invention is delivery of a DNA sequence of interest to the connective tissue of a mammalian host by any of the methods disclosed within this specification so as to effect in vivo expression of various cytokines which possess anti-inflammatory and immunomodulatory characteristics, including but by no means limited to interleukin-4 and interleukin-10.

Another embodiment of the present invention is delivery of a DNA sequence of interest to the connective tissue of a mammalian host by any of the methods disclosed within this specification so as to effect in vivo expression of various antiadhesion molecules so as to inhibit cell-cell and cell-matrix interactions. Examples of such proteins or protein fragments include but are not limited to soluble ICAM-1 and soluble CD44.

Another embodiment of the present invention is delivery of a DNA sequence of interest to the connective tissue of a mammalian host by any of the methods disclosed within this specification so as to effect in vivo expression of various cartilage growth factors, including but not limited to IGF-1 and TGF-β.

Another embodiment of the present invention is delivery of a DNA sequence of interest to the connective tissue of a mammalian host by any of the methods disclosed within this specification so as to effect in vivo expression of various free radical antagonists, thus preventing the deleterious effects of free radical formation within the afflicted joint. Examples include but are not limited to the superoxide dismutase and proteins or protein fragments which inhibit NO.

Another embodiment of the present invention regarding delivery of the IRAP gene to the synovial lining of a mammalian host involves use subcloning this DNA sequence of interest into a viral vector such as adenovirus, adeno-associated virus and herpes-simplex virus. The respective recombinant IRAP based viral vector is then delivered to the joint by direct in vivo injection so as to effect in vivo expression of the IRAP protein or biologically active fragment thereof.

Another embodiment of this invention provides a method of using the gene encoding an extracellular interleukin-1 binding domain of the interleukin-1 receptor. This gene is capable of binding to and neutralizing interleukin-1 in vivo to substantially resist the degradation of cartilage in a mammalian host. Unlike previous pharmacological efforts, the method of this invention employs gene therapy in vivo to address the chronic debilitating effects of arthritis.

A preferred method of using the gene coding for the truncated interleukin-1 receptor of this invention involves employing recombinant techniques to generate a cell line which produces infectious retroviral particles containing the gene coding for the truncated interleukin-1 receptor. The producer cell line is generated by inserting the gene coding into a retroviral vector under the regulation of a suitable eukaryotic promoter, transfecting the retroviral vector containing the gene coding into the retroviral packaging cell line for the production of a viral particle that is capable of expressing the gene coding for the truncated interleukin-1 receptor, and infecting the synovial cells of a mammalian host using the viral particle.

More specifically, the method of using the hereinbefore described gene coding for the truncated interleukin-1 receptor involves introducing the viral particles obtained from the retroviral packaging cell line directly by intra-articular injection into a joint space of a mammalian host that is lined with synovial cells. In a preferred embodiment, synoviocytes recovered from the knee joint are cultured in vitro for subsequent utilization as a delivery system for gene therapy. It will be apparent that Applicants are not limited to the use of the specific synovial tissue disclosed. It would be possible to utilize other tissue sources, such as skin cells, for in vitro culture techniques. The method of using the gene of this invention may be employed both prophylactically and in the therapeutic treatment of arthritis. It will also be apparent that Applicants are not limited to prophylactic or therapeutic applications in treating only the knee joint. It would be possible to utilize the present invention either prophylactically or therapeutically to treat arthritis in any susceptible joint.

In another embodiment of this invention, a method of using the hereinbefore described gene coding for the truncated interlelukin-1 receptor involves infecting synovial cells in culture with the viral particles and subsequently transplanting the infected synovial cells back into the joint. This method of using the gene of this invention may also be employed prophylactically and in the therapeutic treatment of arthritis in any area susceptible to the disorder.

In another embodiment of this invention, a method of using the gene coding for an extracellular interleukin-1 binding domain of the interleukin-1 receptor that is capable of binding to and neutralizing interleukin-1 includes employing recombinant techniques to produce a retrovirus vector carrying two genes. The first gene encodes the extracellular interleukin-1 binding domain of the interleukin receptor, and the second gene encodes for selectable antibiotic resistance. This method of use involves transfecting the retrovirus vector into a retrovirus packaging cell line to obtain a cell line producing infectious retroviral particles carrying the gene.

Another embodiment of this invention provides a method of preparing a gene encoding an extracellular interleukin-1 binding domain of the interlelukin-1 receptor including synthesizing the gene by a polymerase chain reaction, introducing the amplified interleukin-1 receptor coding sequence into a retroviral vector, transfecting the retroviral vector into a retrovirus packaging cell line and collecting viral particles from the retrovirus packaging cell line.

In another embodiment of this invention, a compound for parenteral administration to a patient in a therapeutically effective amount is provided for that contains a gene encoding an extrelelukin-1 binding domain of the interleukin-1 receptor and a suitable pharmaceutical carrier.

Another embodiment of this invention provides for a compound for parenteral administration to a patient in a prophylactically effective amount that includes a gene encoding an extracellular interleukin-1 binding domain of the interleukin-1 receptor and a suitable pharmaceutical carrier.

An additional embodiment of the invention involves transfection of hematopoietic progenitor cells or mature lymphoid or myeloid cells with a DNA vector molecule containing any of the gene or genes disclosed throughout the specification. The transfected cells are recovered and injected into the bone marrow of the patient using techniques known and available to one of ordinary skill in the art. It will be possible, within the scope of this method, to use cells derived from donor bone marrow instead of cells derived from recipient bone marrow so as to modify rejection.

It is an object of the present invention to provide a method of introducing at least one gene encoding a product into at least one cell of a connective tissue of a mammalian host for use in treating the mammalian host.

It is an object of the invention to provide a method of introducing a gene encoding a product into at least one cell of a connective tissue of a mammalian host for a therapeutic use.

It is an object of the present invention to provide a method of introducing into the synovial lining cells of a mammalian arthritic joint at least one gene which codes for proteins having therapeutic properties.

It is an object of the present invention to provide an animal model for the study of connective tissue pathology.

It is an object of the present invention to provide a method of using in vivo a gene coding for the extracellular interleukin-1 binding domain of the interleukin-1 receptor that is capable of binding to and neutralizing substantially all isoforms of interleukin-1, including interleukin-1 alpha and interleukin-1 beta.

It is an object of the present invention to provide a method of using in vivo a gene coding for IRAP or a biologically active derivative thereof which is a competitive inhibitor of and therefore substantially neutralizes all isoforms of interleukin-1, including interleukin-1 alpha and interleukin-1 beta.

It is an object of the present invention to provide a method of using a gene in vivo in a mammalian host that is capable of binding to and neutralizing substantially all isoforms of interleukin-1 and thus, substantially resist the degradation of cartilage and protect surrounding soft tissues of the joint space.

It is an object of the present invention to provide a method of using in vivo a gene coding for the extracellular interleukin-1 binding domain of the interleukin-1 receptor that is capable of binding to and neutralizing substantially all isoforms of interleukin-1 for the prevention of arthritis in patients that demonstrate a high susceptibility for developing the disease.

It is an object of the present invention to provide a method of using in vivo a gene coding for IRAP that is capable of acting as a competitive inhibitor of and therefore substantially neutralizes all isoforms of interleukin-1 for the prevention of arthritis in patients that demonstrate a high susceptibility for developing the disease.

It is an object of the present invention to provide a method of using in vivo a gene coding for an extracellular interleukin-1 binding domain of an interleukin-1 receptor that is capable of binding to and neutralizing substantially all isoforms of interleukin-1 for the treatment of patients with arthritis.

It is an object of the present invention to provide a method of using in vivo a gene coding for IRAP or a biologically active derivative thereof which is a competitive inhibitor of and therefore substantially neutralizes all isoforms of interleukin-1 for the treatment of patients with arthritis.

It is an object of the present invention to provide a method of using in vivo a gene or genes that address the chronic debilitating pathophysiology of arthritis.

It is a further object of the present invention to provide a compound for parenteral administration to a patient which comprises a gene encoding an extracellular interleukin-1 binding domain of the interleukin-1 receptor and a suitable pharmaceutical carrier.

It is a further object of the present invention to provide a compound for parenteral administration to a patient which comprises a gene encoding IRAP and a suitable pharmaceutical carrier.

These and other objects of the invention will be more fully understood from the following description of the invention, the referenced drawings attached hereto and the claims appended hereto.

BRIEF DESCRIPTION OF THE DRAWINGS

FIGS. 8A–8C show the amino acid and nucleotide sequence of the human (SEQ ID NOS 1 and 2) and mouse (SEQ ID NOS 3 and 4) interleukin-1 receptors.

Figure 1:
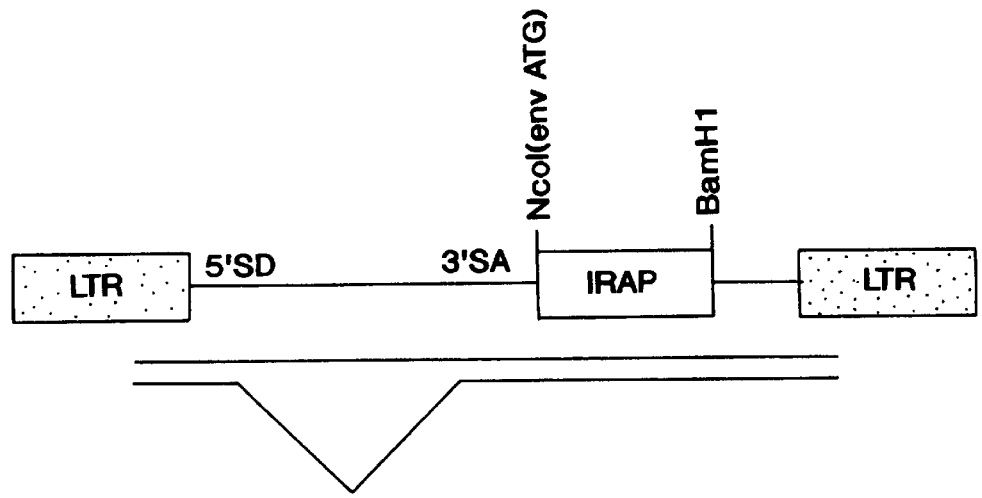
FIG. 1 shows the structure of the cDNA encoding the human interleukin-1 receptor antagonist protein (IRAP) gene inserted into the NcoI and BamHI cloning sites of the retroviral vector MFG.

Numbers of knees are shown above each column. Asterisks denote values which differ at p<0.05 (t-test).

DETAILED DESCRIPTION OF THE INVENTION

As used herein, the term "patient" includes members of the animal kingdom including but not limited to human beings.

As used herein, the term "mammalian host" includes members of the animal kingdom including but not limited to human beings.

As used herein, the term "connective tissue" includes but is not limited to a ligament, a cartilage, a tendon, and a synovium of a mammalian host.

As used herein, the term "DC-chol" means a cationic liposome containing cationic cholesterol derivatives. The "DC-chol" molecule includes a tertiary amino group, a medium length spacer arm (two atoms) and a carbamyol linker bond as described in Biochem. Biophys. Res, Commun., 179:280–285 (1991), X. Gao and L. Huang.

As used herein, "SF-chol" is defined as a type of cationic liposome.

As used herein, the term "biologically active" used in relation to liposomes denotes the ability to introduce functional DNA and/or proteins into the target cell.

As used herein, the term "biologically active" in reference to a nucleic acid, protein, protein fragment or derivative thereof is defined as an ability of the nucleic acid or amino acid sequence to mimic a known biological function elicited by the wild type form of the nucleic acid or protein.

As used herein, the term "maintenance", when used in the context of liposome delivery, denotes the ability of the introduced DNA to remain present in the cell. When used in other contexts, it means the ability of targeted DNA to remain present in the targeted cell or tissue so as to impart a therapeutic effect.

Connective tissues are difficult organs to target therapeutically. Intravenous and oral routes of drug delivery that are known in the art provide poor access to these connective tissues and have the disadvantage of exposing the mammalian host body systemically to the therapeutic agent. More specifically, known intra-articular injection of joints provides direct access to a joint. However, most of the injected drugs have a short intra-articular half-life. The present invention solves these problems by introducing into the connective tissue of a mammalian host genes encoding for proteins that may be used to treat the mammalian host. More specifically, this invention provides a method for introducing into the connective tissue of a mammalian host genes encoding for proteins with anti-arthritic properties.

The present invention provides a method of introducing at least one gene encoding a product into at least one cell of a connective tissue of a mammalian host for use in treating the mammalian host which comprises employing recombinant techniques to produce a viral vector which contains the gene encoding for the product, and infecting the connective tissue cell of the mammalian host using the viral vector containing the gene coding for the product. This method preferably includes introducing the gene encoding the product into at least one cell of the connective tissue of the mammalian host for a therapeutic use.

One ex vivo method of treating a connective tissue disorder disclosed throughout this specification comprises initially generating a recombinant viral vector which contains a DNA sequence encoding a protein or biologically active fragment thereof. This recombinant viral vector is then used to infect a population of in vitro cultured connective tissue cells, resulting in a population of transfected connective cells. These transfected connective tissue cell are then transplanted to connective tissue within a target joint space of a mammalian host, effecting subsequent expression of the protein or protein fragment within the joint space. Expression of this DNA sequence of interest is useful in substantially reducing at least one deleterious joint pathology or indicia of inflammation normally associated with a connective tissue disorder.

The connective tissue cells are selected from the group of connective tissue consisting of a synovium, a cartilage, a tendon and a ligament, preferably synovial cells.

It is also preferred that a retroviral vector, such as MFG, be utilized as the viral vector.

Another preferred step in this ex vivo method is transplantation of transduced cells by by intraarticular injection.

It will be understood by the artisan of ordinary skill that the preferred source of cells for treating a human patient are the patients own cells, such as autologous synovial cells.

In a preferred embodiment of this invention, the method as hereinbefore described includes employing as the gene a DNA sequence encoding a human interleukin-1 receptor antagonist protein (IRAP) or biologically active fragment thereof.

Therefore, a preferred embodiment of the present invention relates to a method of using a DNA sequence encoding a biologically active interleukin-1 receptor antagonist (IRAP) or portion thereof for treatment of connective tissue joint pathologies. The DNA sequence encoding IRAP or a biologically active fragment thereof may be delivered to the connective tissue of a mammalian host by any combination of various vector strategies and transduction techniques disclosed throughout this specification.

A preferred method of the embodiment of delivering IRAP to a target joint space involves delivery of the IRAP gene to the synovial lining of a mammalian host through use of a retroviral vector with the ex vivo technique disclosed within this specification. In other words, a DNA sequence of interest encoding a functional IRAP protein or protein fragment is subcloned into a retroviral vector of choice, the recombinant viral vector is then grown to adequate titers and used to infect in vitro cultured synovial cells, and the transduced synovial cells, preferably autografted cells, are transplanted into the joint of interest, preferably by intra-articular injection.

In another embodiment of this invention, the method as hereinbefore described includes employing as the gene a Lac Z marker gene capable of encoding a beta-galactosidase.

In another embodiment of this invention, the method as hereinbefore described includes employing as the gene a gene capable of encoding a soluble interleukin-1 receptor.

In another embodiment of this invention, the method as hereinbefore described includes employing as the gene a gene capable of encoding a soluble TNF-α receptor.

Another embodiment of this invention includes the method as hereinbefore described including employing as the gene a gene capable of encoding at least proteinase inhibitor. More specifically, this method preferably includes employing a tissue inhibitor of a metalloproteinases as the proteinase inhibitor.

Another embodiment of this invention includes the method as hereinbefore described including employing as the gene a gene capable of encoding at least one cytokine. More specifically, this method includes employing as the cytokine at least one material selected from the group consisting of interleukin-1 alpha (IL-1α), interleukin-1 beta (IL-1α ), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin11 (IL-11), interleukin-12 (IL-12), tumor necrosis factor-α (TNF-α), and tumor necrosis factor-β (TNF-β).

A further embodiment of this invention includes a method as hereinbefore described including employing as the cytokine at least one transforming growth factor. More specifically, this method includes employing as the transforming growth factor a growth factor selected from the group consisting of TGF-beta$_1$, TGF-beta$_2$, TGF-beta$_3$, and TGF-alpha. Each transforming growth factor is commercially available from R & D Systems, 614 McKinley Place, N.E., Minneapolis, Minn. 55413.

In another embodiment of this invention, the method as hereinbefore described includes employing as the cytokine at least one fibroblast growth factor. The fibroblast growth factors are also commercially available from R & D Systems, 614 McKinley Place, N.E., Minneapolis, Minn. 55413.

Another embodiment of this invention includes the method as hereinbefore described including employing as the viral vector a retroviral vector. More specifically, this method includes employing as the retroviral vector at least one material selected from the group consisting of MFG and BAG. A preferred embodiment of this invention includes providing the method as hereinbefore described including employing as the gene a gene capable of encoding a human interleukin-1 receptor antagonist protein and employing MFG as the retroviral vector.

Another preferred embodiment of this invention includes the method as hereinbefore described including employing a Lac Z marker gene as the gene capable of encoding a beta-galactosidase and employing MFG as the retroviral vector.

Another preferred embodiment of this invention provides the method as hereinbefore described including employing a Lac Z neo marker gene as the gene capable of encoding a beta-galactosidase and employing BAG as the retroviral vector.

In a most preferred embodiment of this invention, the method as hereinbefore described includes employing a retroviral vector selected from the group consisting of MFG and BAG and includes employing as the gene a gene capable of encoding a soluble interleukin-1 receptor.

In another embodiment of this invention, a method as hereinbefore described is provided including employing as the gene a gene capable of encoding at least one proteinase inhibitor and including employing as the retroviral vector at least one material selected from the group consisting of MFG and BAG.

In another embodiment of this invention, a method as hereinbefore described is provided which includes employing as the retroviral vector at least one material selected from the group consisting of MFG and BAG and including employing as the gene a gene capable of encoding at least one cytokine as hereinbefore described.

In another embodiment of this invention, a method is provided for introducing at least one gene encoding a product into at least one cell of a connective tissue of a mammalian host for use in treating the mammalian host which comprises employing recombinant techniques to produce a viral vector which contains the gene encoding for the product and infecting the connective tissue cell of the mammalian host using the viral vector containing the gene coding for the product, wherein the viral vector is at least one vector selected from the group consisting of an adeno-associated virus, an adenovirus, and a herpes virus, such as herpes simplex type-1 or herpes simplex type-2. This method includes employing as the gene a gene capable of encoding at least one material selected from the group which includes (a) a human interleukin-1 receptor antagonist protein, (b) a soluble interleukin-1 receptor, (c) a Lac Z marker gene capable of encoding a beta-galactosidase, (d) at least one proteinase inhibitor and (e) at least one cytokine. More specifically, this method includes employing a tissue inhibitor of metalloproteinases as the proteinase inhibitor and includes employing as the cytokine at least one of the materials selected from the group which includes (a) at least one transforming growth factor selected from the group consisting of TGF-beta$_1$, TGF-beta$_2$, TGF-beta$_3$, and TGF-alpha, (b) at least one fibroblast growth factor, (c) IL-1α, (d) IL-1α, (e) IL-2 (f) IL-3, (g) IL-4, (h) IL-5, (i) IL-6,(j) IL-7, (k) IL-8, (l) IL-9, (m) IL-10, (o) IL-12, (p) TNF-α, and (q) TNF-β.

Another embodiment of this invention includes the method as hereinbefore described including introducing the gene into a connective tissue which tissue is selected from the group consisting of a ligament, a cartilage, a tendon, and a synovium. It is preferable that this method includes employing a cruciate ligament as the ligament. Most preferable this method includes employing as the cruciate ligament a ligament selected from the group consisting of an anterior cruciate ligament and a posterior cruciate ligament.

Another embodiment of this invention includes the method as hereinbefore described including employing as the gene a gene having DNA that is capable of maintenance and expression.

A further embodiment of this invention includes the method as hereinbefore described including introducing the gene into the cell in vitro. This method also subsequently transplanting the infected cell into the mammalian host. This method includes after effecting the infecting of the connective tissue cell but before the transplanting of the infected cell into the mammalian host, storing the infected connective tissue cell. It will be appreciated by those skilled in the art that the infected connective tissue cell may be stored frozen in 10 percent DMSO in liquid nitrogen. This method includes employing a method to substantially prevent the development of arthritis in a mammalian host having a high susceptibility of developing arthritis.

The method of this invention includes employing the method on an arthritic mammalian host for a therapeutic use. This method includes employing a method to repair and regenerate the connective tissue which tissue is selected from the group consisting of a ligament, a cartilage, a tendon, and a synovium. This method includes employing the method on a mammalian host that is a human being.

Another embodiment of this invention includes a method of introducing at least one gene encoding a product into at least one cell of a connective tissue of a mammalian host for use in treating the mammalian host as hereinbefore described including effecting in vivo the infection of the cell by introducing the viral vector containing the gene coding for the product directly into the mammalian host. Preferably, this method includes effecting the direct introduction into the mammalian host by intra-articular injection. This method includes employing the method to substantially prevent a development of arthritis in a mammalian host having a high susceptibility of developing arthritis. This method also includes employing the method on an arthritic mammalian host for therapeutic use. Further this method also includes employing the method to repair and regenerate the connective tissue as hereinbefore defined.

In yet another embodiment of this invention, a method of introducing at least one gene encoding a product into at least one cell of a connective tissue of a mammalian host for use in treating the mammalian host includes employing non-viral means for introducing the gene encoding for the product into the connective tissue cell. This method includes employing non-viral means selected from the group consisting of at least one liposome, $Ca_3(PO_4)_2$, electroporation, and DEAE-dextran. This method includes employing as the liposome a material selected from the group consisting of DC-chol and SF-chol.

It will be understood that the method of this invention of introducing at least one gene encoding a product into at least one cell of a connective tissue of a mammalian host for use in treating the mammalian host that includes employing non-viral means for introducing the gene encoding for the product into the connective tissue cell is a non-infectious delivery system. An advantage of the use of a non-infectious delivery system is the elimination of insertional mutagenesis and virally induced disease.

It will be appreciated by those skilled in the art, that the viral vectors employing a liposome are not limited by cell division as is required for the retroviruses to effect infection and integration of connective tissue cells. This method employing non-viral means as hereinbefore described includes employing as the gene a gene capable of encoding at least one of the following materials selected from the group which includes (a) a human interleukin-1 receptor antagonist protein, (b) a Lac Z marker gene capable of encoding a beta-galactosidase, (c) a soluble interleukin-1 receptor, (d) at least one proteinase inhibitor, (e) at least one transforming growth factor, and (f) at least one cytokine. More specifically, this method includes employing as the cytokine a cytokine selected from the group which includes IL-1α, IL-1β, IL-2, IL-3, IL-4, IL-5, IL-6, IL-7, IL-8, IL-9, IL-10, IL-11, IL-12, TNF-α, and TNF-β, and at least one fibroblast growth factor. Preferably, IL-4 and IL-10 are the selected cytokines. Preferably, this method includes employing as the transforming growth factor a growth factor selected from the group consisting of TGF-beta$_1$, TGF-beta$_2$, TGF-beta$_3$, and TGF-alpha.

High levels of collagenase and other tissue metalloproteinases, such as stromelysin and gelatinase can be expressed in the presence of IL-1 within connective tissue. Collagenase, stromelysin, and gelatinase are inhibited by the protein TIMP ("Tissue Inhibitor of MetalloProteinases"). Therefore, another preferred embodiment of this invention includes providing the method employing non-viral means as hereinbefore described which includes employing a tissue inhibitor of metalloproteinases (TIMP) as the proteinase inhibitor. This method employing non-viral means for introducing the gene encoding for the product into the connective tissue cell as hereinbefore described includes introducing the gene into the connective tissue which tissue is selected from the group consisting of a ligament, a cartilage, a tendon, and a synovium. Preferably, this method includes employing a cruciate ligament as the ligament. The cruciate ligament is selected from the group consisting of an anterior cruciate ligament and an posterior cruciate ligament. Of course, a gene encoding a TIMP protein or biologically active fragment thereof could be delivered to the target connective tissue by any combination of means disclosed in this specification.

Another embodiment of the present invention is delivery of a DNA sequence of interest to the connective tissue of a mammalian host by any of the methods disclosed within this specification so as to effect in vivo expression of various antiadhesion molecules so as to inhibit cell-cell and cell-matrix interactions. Examples of such proteins or protein fragments include but are not limited to soluble ICAM-1 and soluble CD44.

Another embodiment of the present invention is delivery of a DNA sequence of interest to the connective tissue of a mammalian host by any of the methods disclosed within this specification so as to effect in vivo expression of various cartilage growth factors, including but not limited to IGF-1 and TGF-β.

Another embodiment of the present invention is delivery of a DNA sequence of interest to the connective tissue of a mammalian host by any of the methods disclosed within this specification so as to effect in vivo expression of various free radical antagonists, thus preventing the deleterious effects of free radical formation within the afflicted joint. Examples include but are not limited to the superoxide dismutase and proteins or protein fragments which inhibit NO.

A further embodiment of this invention provides for an animal model to study connective tissue pathologies and indices of systemic inflammation. This model utilizes either ex vivo or in vivo delivery of at least one gene or DNA sequence of interest encoding a product into a least one cell of a connective tissue of a mammalian host. Examples of joint pathologies which can be studied in the present invention include, but are by no means limited to, joint pathologies such as leukocytosis, synovitis, cartilage breakdown and suppression of cartilage matrix synthesis. Examples of indices of systemic inflammation which include, but are by no means limited to, erythtocyte sedimentation rate, fever and weight loss.

A particular embodiment of the present invention which relates to such an animal model is utilization of the ex vivo based delivery of a DNA sequence encoding human IL-1β gene to the synovial lining of the rabbit knee. In this embodiment, the human IL-1β gene was subcloned into the MFG retroviral vector by known methods, resulting in MFG-IL-1β. This recombinant retroviral construct was used to transduce autologous synovial cells cultured in vitro. These transduced cells were then delivered to the rabbit knees as described throughout this specification. Delivery of the human IL-1α gene to the synovial lining of the rabbit knee in this fashion caused a severe, chronic, monarticular arthritis. Pathologies included leukocytosis, synovitis, cartilage breakdown and suppression of cartilage matrix synthesis. Various systemic indices of inflammation were also effected, including an increased erythrocyte sedimentation rate, fever and weight loss.

In another example of this particular embodiment of the present invention, the human IL-1α gene was subcloned into a DNA plasmid vector, downstream of a CMV promoter. This CMV-IL-1β plasmid construct was encapsulated in liposomes and delivered to a target joint space as described in Example X. Forty eight hours subsequent to injection 1 ng on IL-1β was recovered from the knee joint area.

An animal model as described and exemplified in this specification measures the ability of various gene therapy applications disclosed throughout this specification to withstand challenges from known causative agents (such as IL-1β) of joint pathologies and inflammatory side effects.

Another preferred method of the present invention involves direct in vivo delivery of the IRAP gene to the synovial lining of a mammalian host through use of either an adenovirus vector, adeno-associated virus (AAV) vector or herpes-simples virus (HSV) vector. In other words, a DNA sequence of interest encoding a functional IRAP protein or protein fragment is subcloned into the respective viral vector, the IRAP containing viral vector is then grown to adequate titers and directed into the joint space, preferably by intra-articular injection. A retroviral-IRAP construct, such as MFG-IRAP may also be utilized to directly target previously inflamed connective tissue cells within the joint space.

Direct intra-articular injection of a DNA molecule containing the gene of interest into the joint results in transfection of the recipient synovial cells and hence bypasses the requirement of removal, in vitro culturing, transfection, selection, as well as transplanting the DNA vector containing—synoviocytes (as disclosed in the Example section) to promote stable expression of the heterologous gene of interest. Methods of presenting the DNA molecule to the target connective tissue of the joint includes, but is not limited to, encapsulation of the DNA molecule into cationic liposomes, subcloning the DNA sequence of interest in a retroviral vector as described throughout this specification, or the direct injection of the DNA molecule itself into the joint. The DNA molecule, regardless of the form of presentation to the knee joint, is preferably presented as a DNA vector molecule, either as recombinant viral DNA vector molecule or a recombinant DNA plasmid vector molecule. Expression of the heterologous gene of interest is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the synovial tissue. In vivo delivery of various viral and non-viral vectors to the rabbit knee joint are described in Example XV.

Another embodiment of this invention provides the method of introducing at least one gene encoding a product into at least one cell of a connective tissue of a mammalian host for use in treating the mammalian host which includes employing non-viral means as hereinbefore described and includes employing as the gene a gene having DNA that is capable of maintenance and expression.

In yet a further embodiment of this invention, the method of introducing at least one gene encoding a product into at least one cell of a connective tissue of a mammalian host for use in treating the mammalian host is provided that includes employing non-viral means for introducing the gene encoding for the product into the connective tissue cell in vitro and includes subsequently transplanting the cell having the gene into the mammalian host. Another embodiment of this invention provides a method including after introducing the gene encoding for the product in the connective tissue cell and before the transplanting of the connective tissue cell having the gene into the mammalian host, storing the connective tissue cell having the gene. This method includes storing connective tissue cell frozen in 10 percent DMSO in liquid nitrogen. This method includes employing a method to substantially prevent the development of arthritis in a mammalian host having a high susceptibility of developing arthritis. Further, this method includes employing the method on an arthritic mammalian host for a therapeutic use. This method includes employing the method to repair and regenerate the connective tissue which tissue is selected from the group consisting of a ligament, a cartilage, a tendon, and a synovium.

A further embodiment of this invention provides a method of introducing at least one gene encoding a product into at least one cell of a connective tissue of a mammalian host for use in treating the mammalian host which includes employing non-viral means in vivo for directly introducing the gene encoding for the product into the connective tissue cell of the mammalian host. The non-viral means is selected from the group consisting of at least one liposome, $Ca_3(PO_4)_2$ and DEAE-dextran. Preferably, this method includes effecting the in vivo introduction into the mammalian host by intra-articular injection. This method includes employing the method to substantially prevent the development of arthritis in a mammalian host having a high susceptibility of developing arthritis. Further, this method includes employing the method on an arthritic mammalian host for a therapeutic use. This method also includes employing the method to repair and regenerate the connective tissue which tissue is selected from the group consisting of a ligament, a cartilage, a tendon, and a synovium.

Another embodiment of the present invention is a method to produce an animal model for the study of connective tissue pathology. As will be understood by those skilled in the art, over-expression of interleukin-1 in the joint of a mammalian host is generally responsible for the induction of an arthritic condition. This invention provides a method for producing an animal model using the hereinbefore described gene transfer technology of this invention. Preferably, the method of this invention provides a method for producing an animal model using the hereinbefore described gene transfer technology of this invention to effect an animal model for arthritis. For example, constitutive expression of interleukin-1 in the joint of a rabbit following the method of gene transfer provided for by this invention leads to the onset of an arthritic condition. It will be appreciated by those skilled in the art that this rabbit model is suitable for use for the testing of therapeutic agents. This method includes introducing at least one gene encoding a product into at least one cell of a connective tissue of a mammalian host comprising (a) employing recombinant techniques to produce a viral vector which contains the gene encoding for the product and (b) infecting the connective tissue cell of the mammalian host using the viral vector containing the gene coding for the product for effecting the animal model. This method includes employing as the gene a material selected from the group consisting of a cytokine and a proteinase. This method includes employing as the cytokine a material selected from the group consisting of IL-1α, IL-1β and TNF-1α. This method includes employing as the proteinase a matrix metalloproteinase. The matrix metalloproteinase is an enzyme selected from the group consisting of a collagenase, a gelatinase and a stromelysin. It will be apparent that use of the term "a collagenase, a gelatinase and a stromolysin" is meant to include the plural, and not be limited to the singular. It is well known in the art that numerous collagenases, gelatinases and stromolysins could be employed as a matrix metalloproteinase in the present invention. A further embodiment of this invention provides a method to produce an animal model for the study of connective tissue pathology which includes employing non-viral means for introducing at least one gene encoding a product into at least one cell of a connective tissue of a mammalian host for effecting the animal model. The non-viral means is selected from the group consisting of at least one liposome, $Ca_3(PO_4)_2$, electroporation, and DEAE-dextran. This method includes employing as the gene a material selected from the group consisting of a cytokine and a proteinase. This method includes employing as the cytokine a material selected from the group consisting of IL-1α, IL-1β and TNF-α. This method also includes employing as the proteinase a matrix metalloproteinase. The matrix metalloproteinase includes an enzyme selected from at least one of the group consisting of a collagenase, a gelatinase, and a stromelysin.

A further embodiment of the present invention includes employing as the gene a gene capable of encoding at least one of the materials which is selected from the group which includes (a) a human interleukin-1 receptor antagonist protein or a biologically active derivative or fragment thereof, (b) a Lac Z marker gene capable of encoding a beta-galactosidase protein or a biologically active derivative or fragment thereof, (c) a soluble interleukin-1 receptor protein or a biologically active derivative or fragment thereof, (d) a proteinase inhibitor, (e) a soluble tumor necrosis factor receptor protein or a biologically active derivative or fragment thereof and (f) a cytokine, and employing as the DNA vector any DNA vector, preferably a plasmid or viral vector, known to one of ordinary skill in the art capable of stable maintenance within the targeted cell or tissue upon delivery, regardless of the method of delivery utilized. In one embodiment of the invention, synoviocytes are transfected in vivo subsequent to direct intra-articular injection of a DNA molecule containing the gene of interest into the joint. Transfection of the recipient synovial cells bypasses the requirement of removal, culturing, in vitro transfection, selection and transplanting the DNA vector containing—synoviocytes (as disclosed in the Example section) to promote stable expression of the heterologous gene of interest. Methods of injecting the DNA molecule into the joint includes, but is not limited to, encapsulation of the DNA molecule into cationic liposomes or the direct injection of the DNA molecule itself into the joint. Expression of the heterologous gene of interest subsequent to in vivo transfection of the synovial tissue is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the synovial tissue. As an example, and not a limitation, of the present invention, a DNA plasmid vector containing the IL-1β coding sequence ligated downstream of the CMV promoter was encapsulated within liposomes and injected into the knee joints of recipient rabbits. Interleukin-1 beta was expressed in synovial tissue, as significant amounts of interlelukin-1 beta was recovered from the synovial tissue within the region of intra-articular injection.

A further embodiment of this invention provides an additional method for introducing at least one gene encoding a product into at least one cell of a connective tissue of a mammalian host for use in treating the mammalian host. This additional method includes employing the biologic means of utilizing a virus to deliver the DNA vector molecule to the target cell or tissue. Preferably, the virus is a psuedovirus, the genome having been altered such that the psuedovirus is capable only of delivery and stable maintenance within the target cell; but not retaining an ability to replicate within the target cell or tissue. The altered viral genome is further manipulated by recombinant DNA techniques such that the viral genome acts as a DNA vector molecule which contains the heterologous gene of interest to be expressed within the target cell or tissue. This method also includes employing as the gene a gene capable of encoding at least one of the materials selected from the group which includes (a) a human interleukin-1 receptor antagonist protein or biologically active derivative or fragment thereof, (b) a Lac Z marker gene capable of encoding a beta-galactosidase protein or biologically active derivative or fragment thereof, (c) a soluble interleukin-1 receptor protein or biologically active derivative or fragment thereof, (d) a proteinase inhibitor and (e) a soluble tumor necrosis factor receptor protein or a biologically active derivative or fragment thereof and (f) a cytokine.

The following examples are offered by way of illustration of the present invention, and not by way of limitation.

EXAMPLE I
Packaging of AAV

The only cis-acting sequences required for replication and packaging of recombinant adeno-associated virus (AAV) vector are the AAV terminal repeats. Up to 4 kb of DNA can be inserted between the terminal repeats without effecting viral replication or packaging. The virus rep proteins and viral capsid proteins are required in trans for virus replication as is an adeno-associated virus helper. To package a recombinant AAV vector, the plasmid containing the terminal repeats and the therapeutic gene is co-transfected into cells with a plasmid that expresses the rep and capsid proteins. The transfected cells are then infected with adeno-associated virus and virus isolated from the cells about 48–72 hours post-transfection. The supernatants are heated to about 56° Centigrade to inactivate the adeno-associated virus, leaving a pure virus stock of recombinant AAV.

EXAMPLE II
Electroporation

The connective tissue cells to be electroporated are placed into Hepes buffer saline (HBS) at a concentration of about $10^7$ cells per ml. The DNA to be electroporated is added at a concentration of about 5–20 ug/ml of HBS. The mixture is placed into a cuvette and inserted into the cuvette holder that accompanies the Bio-RAD electroporation device (1414 Harbour Way South, Richmond, Calif. 94804). A range between about 250 and 300 volts at a capacitance of about 960 ufarads is required for introduction of DNA into most eukaryotic cell types. Once the DNA and the cells are inserted into the Bio-RAD holder, a button is pushed and the set voltage is delivered to the cell-DNA solution. The cells are removed from the cuvette and replated on plastic dishes.

EXAMPLE III

The cDNA encoding the human interleukin-1 receptor antagonist (IRAP) was inserted into the NcoI and BamHI cloning sites of the retroviral vector MFG as shown in FIG. 1. Specifically, a Pst1 to BamHI fragment from the IRAP cDNA was linked to a synthetic oligonucleotide adapter from the NcoI site (representing the start site of translation for IRAP) to the Pst1 site (approximately 12 base pairs downstream from the NcoI site) to the MFG backbone digested at NcoI and BamHI in a three part ligation reaction. This three part ligation involving a synthetic oligo and two DNA fragments is well known by those skilled in the art of cloning. LTR means long terminal repeats, 5'SD means 5'splice donor, 3'SA means 3' splice acceptor. The straight arrow and the crooked arrow in FIG. 1 represent unspliced and spliced messenger RNAs respectively. IRAP is encoded by the spliced message.

Figure 2:
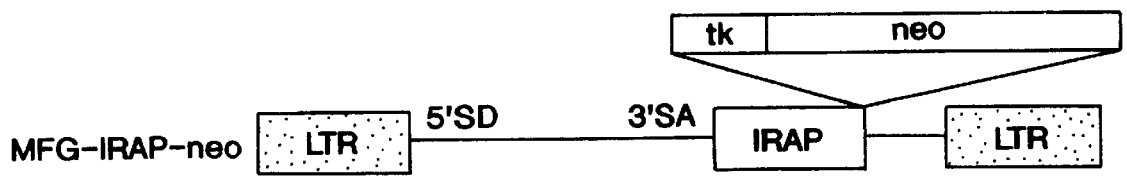
FIG. 2 shows the structure of the cDNA encoding the human interleukin-1 receptor antagonist protein (IRAP) gene with a selectable neo marker inserted into the retroviral vector MFG.
Figure 3:
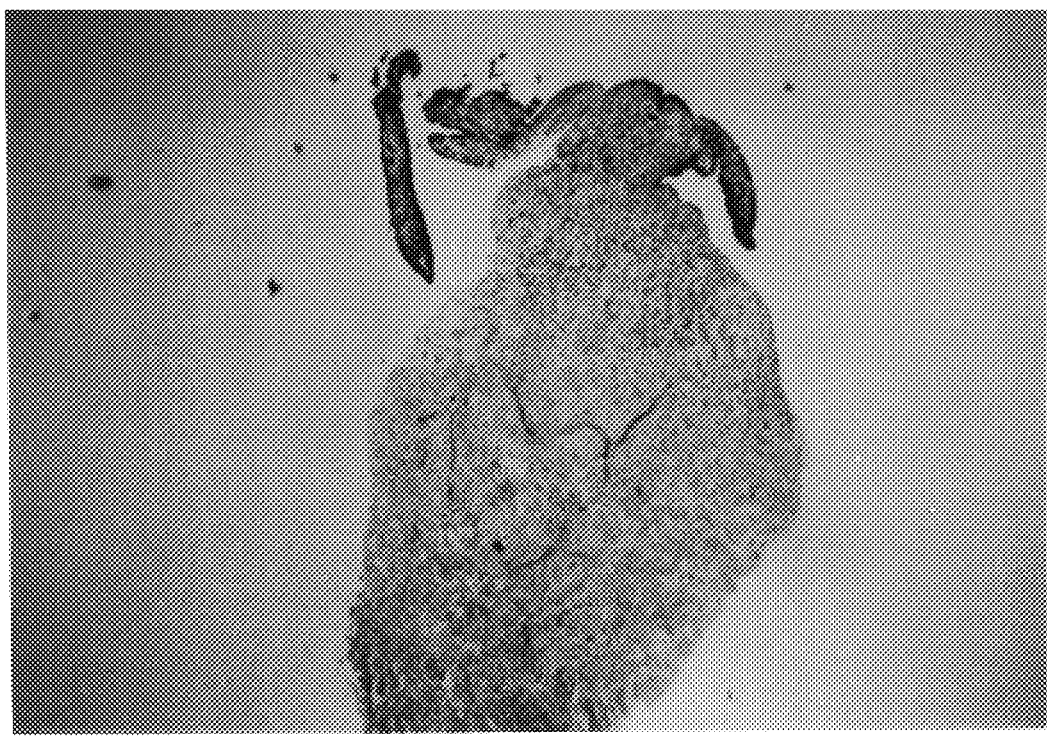
FIG. 3 shows a micrograph of synovium recovered from the knee of a rabbit approximately one month after intra-articular injection of Lac Z$^+$, neo synoviocytes employing the methods of this invention.

FIG. 2 shows the cDNA encoding the human interleukin-1 receptor antagonist protein (IRAP) with a selectable neo gene marker. FIG. 3 shows a low power micrograph of synovium recovered from the knee of a rabbit one month after intra-articular injection of Lac $Z^+$, neo$^+$ synoviocytes. Tissue was stained histochemically for the presence of beta-galactosidase. This micrograph counterstained with eosin revealed an area of intensely stained, transplanted cells demonstrating that these cells have colonized the synovial lining of the recipient joint.

EXAMPLE IV
Animal Models

The methods of this invention of transferring genes to the synovia of mammalian joints permit the production and analysis of joint pathologies that were not previously possible. This is because the only other way of delivering potentially arthriotogenic compounds to the joint is by intra-articular injection. Not only are such compounds quickly cleared from joints, but the effects of bolus injections of these compounds do not accurately mimic physiological conditions where they are constantly produced over a long period of time. In contrast, the gene transfer technologies of this invention permit selected proteins of known or suspected involvement in the arthritic process to be expressed intra-articularly over an extended period of time, such as for example, at least a three month period. The animal models of this invention therefore permits the importance of each gene product to the arthritic process to be evaluated individually. Candidate genes include, but are not restricted to, those coding for cytokines such as interleukin-1 (IL-1) alpha, IL-1 beta, and TNF-alpha, and matrix metalloproteinases such as collagenases, gelatinases and stromelysins.

Additionally, the gene transfer techniques of this invention are suitable for use in the screening of potentially therapeutic proteins. In this use, the animal models of the invention are initiated in joints whose synovia express gene coding for potential anti-arthritic proteins. Candidate proteins include, but are not restricted to, inhibitors of proteinases such as, for example, the tissue inhibitor of metalloproteinases, and cytokines such as, for example, transforming growth factor-beta.

EXAMPLE V

Method For Using Synoviocytes As A Delivery System For Gene Therapy

Rabbits are killed by intravenous injection of 4 ml nembutol, and their knees quickly shaved. Synovia are surgically removed from each knee under aseptic conditions, and the cells removed from their surrounding matrix by sequential digestion with trypsin and collagenase (0.2% w/v in Gey's Balanced Salt Solution) for about 30 minutes and about 2 hours, respectively. The cells recovered in this way are seeded into 25 cm$^2$ culture flasks with about 4 ml of Ham's $F_{12}$ nutrient medium supplemented with 10% fetal bovine serum, about 100 U/ml penicillin and about 100 μg/ml streptomycin, and incubated at about 37° in an atmosphere of 95% air, 5% $CO_2$. Following about 3–4 days incubation, the cells attain confluence. At this stage, the culture medium is removed and the cell sheet washed twice with approximately 5 mls of Gey's Balanced Salt Solution to remove non-adherent cells such as lymphocytes. The adherent cells are then treated with trypsin (0.25% w/v in balanced salt solution). This treatment detaches the fibroblastic, Type B synoviocytes, but leaves macrophages, polymorphonuclear leukocytes and the Type A synoviocytes attached to the culture vessel. The detached cells are recovered, re-seeded into 25 cm$^2$ culture vessels at a 1:2 split ratio, medium is added and the culture returned to the incubator. At confluence this procedure is repeated.

After the third such passage, the cells are uniformly fibroblastic and comprise a homogeneous population of Type B synoviocytes. At this stage, cells are infected with the retroviral vector.

Following infection, cells are transferred to fresh nutrient medium supplemented with about 1 mg/ml G418 (GIBCO/BRL, P.O. Box 68, Grand Island, N.Y. 14072-0068) and returned to the incubator. Medium is changed every three days as neo cells die and the neo$^+$ cells proliferate and attain confluency. When confluent, the cells are trypsinized and subcultured as described above. One flask is set aside for staining with X-gal to confirm that the neo$^+$ cells are also Lac Z$^+$. When the subcultures are confluent, the medium is recovered and tested for the presence of IRAP, soluble IL-1R or other appropriate gene products as hereinbefore described. Producing synoviocyte cultures are then ready for transplantation.

The day before transplantation, the cells are recovered by trypsinizing, as hereinbefore described. These cells are then suspended in nutrient medium, and incubated overnight in an untreated plastic centrifuge tube. Under these conditions, the cells do not adhere, but they regenerate their cell surface proteins that were removed by trypsinizing.

The following morning, the cells are recovered by centrifuging, washed several times by resuspension in Gey's Balanced Salt Solution and finally resuspended at a concentration of about $10^6$–$10^7$ cells/ml in Gey's solution. Approximately 1 ml of this suspension is then introduced into the knee joint of a recipient rabbit by intra-articular injection. For this purpose a 1 ml syringe with a 25-gauge hypodermic needle is used. Injection is carried out through the patellar tendon. Experiments in which radiopaque dye was injected have confirmed that this method successfully introduces material into all parts of the joint.

Variations on the disclosed harvesting, culture and transplantation conditions in regard to the numerous examples presented within this specification will be evident upon inspection of this specification. Several tangential points may be useful to one practicing the ex vivo based gene therapy portion of the disclosed invention:

(1) If the yield of synoviocytes from the harvested synovial tissue is poor, the surgical technique may be at fault. The synovium has a strong tendency to retract when cut. Therefore, the inner capsule is grasped firmly, and with it the synovium, while excising this tissue. A small (about 2 mm) transverse incision can be made inferiorly, followed by sliding one point of the forceps into the joint space so that the synovium and inner capsule are sandwiched between the points of the forceps. The tissue is then excised without releasing the tissue thus preventing retraction of the synovium.

(2) A two compartment digestion chamber may be used to initially separate the cells from extracellular debris. In lieu of this choice, synovial tissue may be digested in a single chamber vessel and filtered through a nylon monofilament mesh of 45 μm pore size.

(3) When resuspending cells, the smallest amount of medium possible can be used to prevent formation of clumps of cells, which are difficult to separate once formed.

(4) During trypsinization, synoviocytes can lose the stellate/dendritic morphology that they possess in adherence, and assume a rounded shape. The cells initially will detach in clumps of rounded cells; one may allow the majority of cells to separate from each other before stopping trypsinization.

(5) Synoviocytes may be transduced with multiple transgenes by use of retroviral vectors containing multiple transgenes or by sequential transduction by multiple retroviral vectors. In sequential transduction, the second transduction should be made following selection, when applicable, and passage after the first transduction.

(6) As the synovium is a well-innervated structure, intra-articular injection can be painful, especially if done rapidly. Intra-articular injection of a 1 ml volume should take 10 to 15 seconds.

(7) In the animal model, the depth of the needle stick should not exceed 1 cm during intraarticular injection, and depression of the syringe plunger should meet with little to no resistance. Resistance to advancement of the syringe plunger indicates that the tip of the needle is not in the joint space.

(8) In the animal model, to retrieve a useful volume of the injected Gey's solution during joint lavage, the needle should not be inserted too deeply, otherwise it may penetrate the posterior capsule and may lacerate the popliteal artery. Firm massage of the suprapatellar, infrapatellar, and lateral aspects of the knee during aspiration helps to increase the amount of fluid recovered; in general, it should be possible to recover $\geq$0.5 ml of fluid. When knees are badly inflamed, lavage is often difficult because of the presence of large numbers of leukocytes, fibrin, and other debris in the joint.

Under such conditions the only recourse is to sacrifice the animal and recover the Gey's solution surgically.

EXAMPLE VI

The method of Example V for producing generally uniformly fibroblastic cells of a homogeneous population of Type B synoviocytes was followed to effect growing cultures of lapine synovial fibroblasts. These growing cultures of lapine synovial fibroblasts were subsequently infected with an amphotropic retroviral vector carrying marker genes coding for beta-galactosidase (Lac Z) and resistance to the neomycin analogue G418 (neo$^+$). Following infection and growth in selective medium containing about 1 mg/ml G418, all cells stained positively in a histochemical stain for beta-galactosidase.

Neo selected cells carrying the Lac Z marker gene were transplanted back into the knees of recipient rabbits to examine the persistence and expression of these genes in vivo. Two weeks following transplantation, islands of Lac Z$^+$ cells within the synovium of recipient knees were observed. This confirmed the ability of the method of this invention to introduce marker genes into rabbit synovia and to express them in situ.

EXAMPLE VII

Neo-selected, Lac Z$^+$ synoviocytes were recovered from cell culture, suspended in Gey's Balanced Salt Solution and injected intra-articularly into the knee joints of recipient rabbits (about $10^5$–$10^7$ cells per knee). Contralateral control knees received only a carrier solution. At intervals up to 3 months following transplant, the rabbits were killed and their synovia and surrounding capsule recovered. Each sample may be analyzed in three ways. A third of the synovium was stained histochemically en masse for the presence of beta-galactosidase. A second portion may be used for immunocytochemistry using antibodies specific for bacterial beta-galactosidase. The final portion may be digested with trypsin and collagenase, and the cells thus recovered cultured in the presence of G418.

Staining of the bulk synovial tissue revealed extensive areas of Lac Z$^+$ cells, visible to the naked eye. Control synovia remained colorless. Histochemical examination of synovia revealed the presence of islands of cells staining intensely positive for beta-galactosidase. These cells were present on the superficial layer of the synovial lining, and were absent from control synovia. From such tissue it was possible to grow Lac Z$^+$, neo$^+$ cells. Cells recovered from control tissue were Lac Z$^-$ and died when G418 was added to the culture. This indicates that the transplanted, transduced synovial fibroblasts have successfully recolonized the synovia of recipient joints, and continue to express the two marker genes, Lac Z and neo. Maintaining intra-articular Lac Z and neo expression in transplanted synoviocytes has been effected for 3 months using primary cells and one month using the HIG-82 cell line.

EXAMPLE VIII

Based upon the methods of the hereinbefore presented examples, and employing standard recombinant techniques well known by those skilled in the art, the human IRAP gene was incorporated into an MFG vector as shown in FIG. 1. Following the infection of synoviocyte cultures of rabbit origin with this viral vector, IRAP was secreted into the culture medium.

Figure 4:
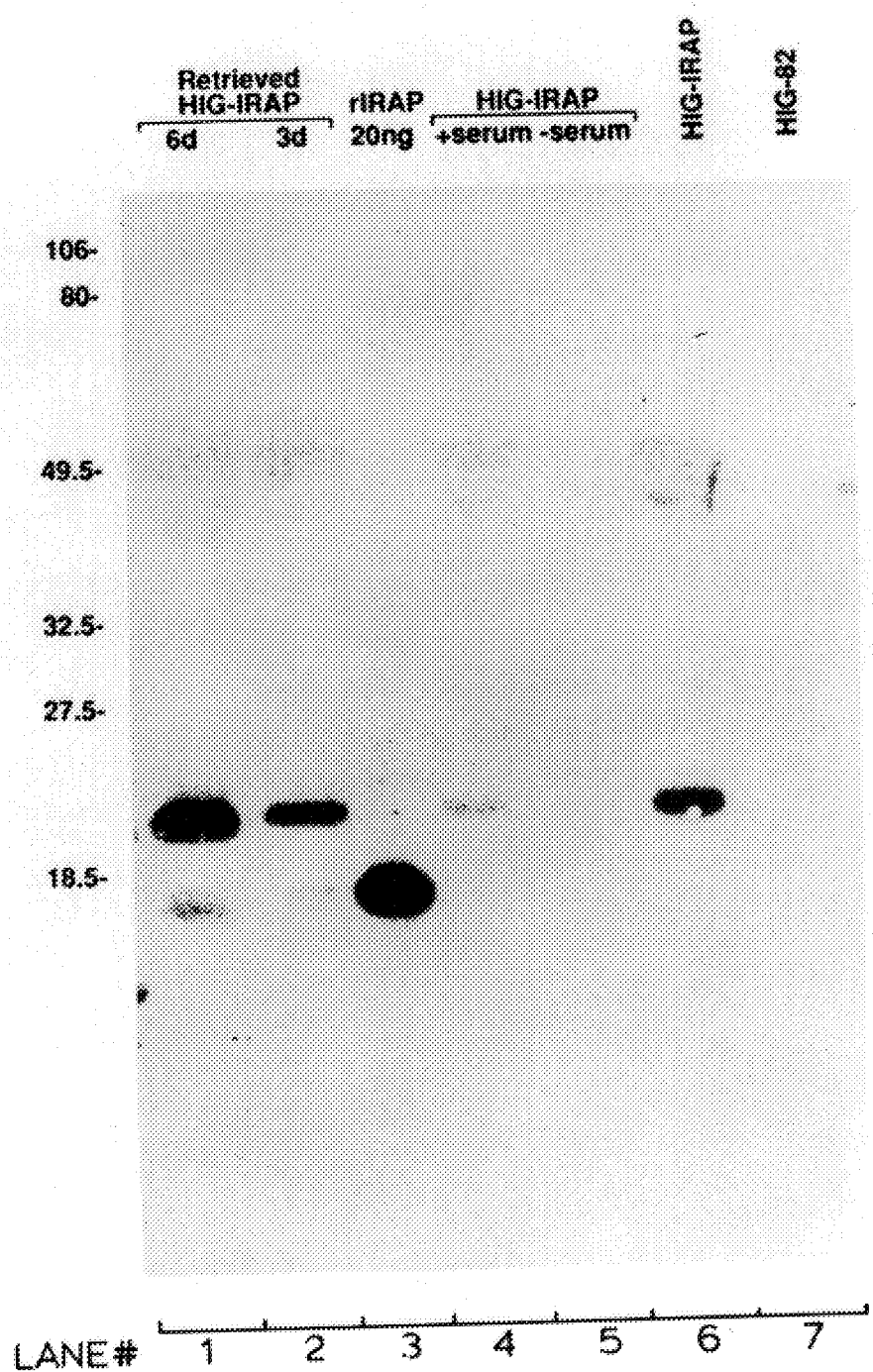
FIG. 4 shows a Western blot demonstrating the production of interleukin-1 receptor antagonist protein by four cultures of HIG-82 cells (Georgescu, et al., 1988, In Vitro 24: 1015–1022) infected using the method of this invention employing the MFG-IRAP viral vector.

Western blotting, well known by those skilled in the art, was carried out using an IRAP-specific rabbit polyclonal antibody that does not recognize human or rabbit IL-1 alpha or IL-1 beta, or rabbit IRAP. FIG. 4 shows a Western blot which sets forth the production of IRAP by four cultures of HIG-82 cells infected with MFG-IRAP. Three forms of the IRAP are present: a non-glycosylated form which runs with recombinant standards, and two larger glycosylated forms. The results of the Western blotting shown in FIG. 4 demonstrated that IRAP was produced by HIG-82 synoviocyte cell line (Georgescu, 1988, In Vitro 24:1015–1022) following infection with the MFG-IRAP vector of this invention. The Western blotting of FIG. 4 shows the IRAP concentration of the conditioned medium is as high as 50 ng/ml. This is approximately equal to 500 ng IRAP/$10^6$ cells/day. Lane 1 and Lane 2 of FIG. 4 show that the recipient synovia tissue secrete substantial amounts of HIG-IRAP at 3 days (Lane 2) and 6 days (Lane 1). Lane 3 shows human recombinant IRAP. Lane 6 indicates that rabbit synovial cells produce a larger glycosylated version of this molecule after infection with MFG-IRAP. Lane 7 indicates that native rabbit synovial cells do not produce this glycosylated form.

Figure 5:
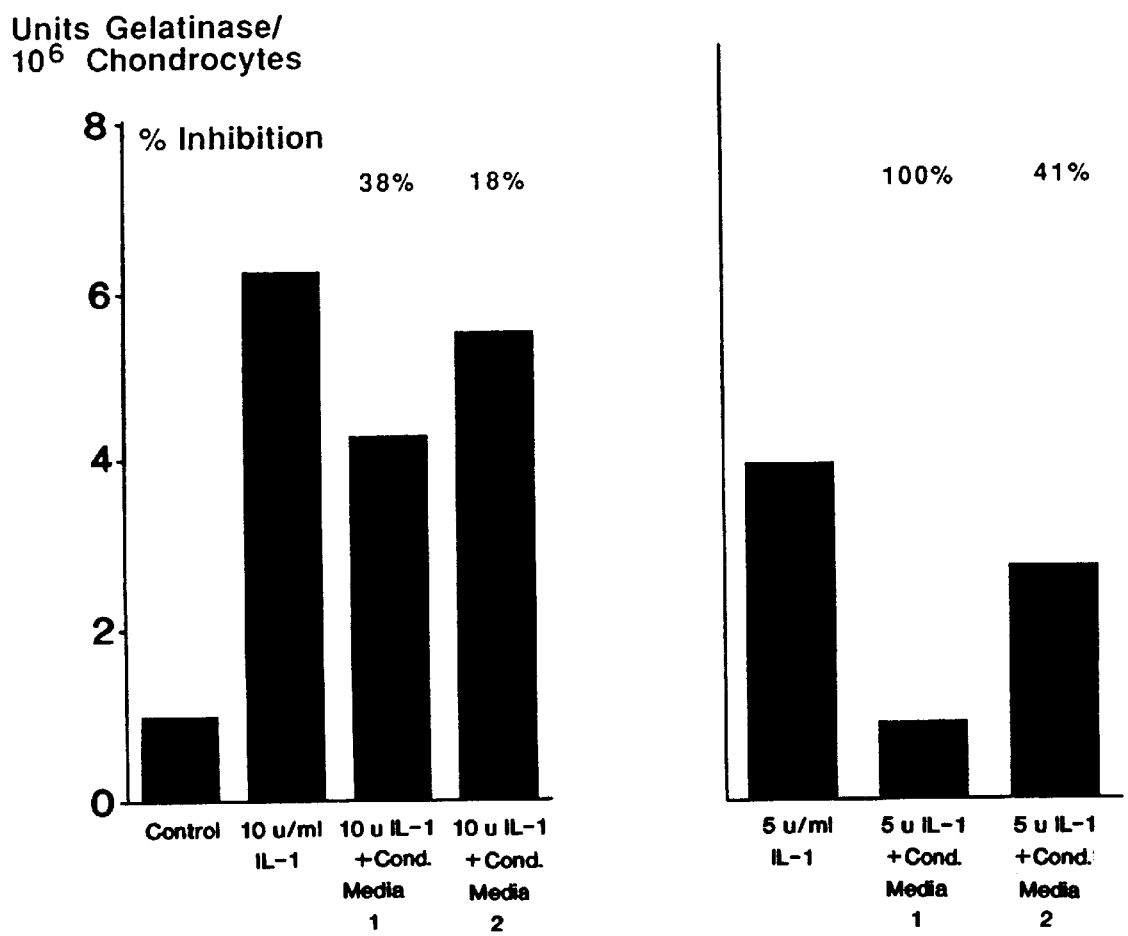
FIG. 5 shows data demonstrating the inhibition of chondrocytes by the addition of medium conditioned by MFG-IRAP infected HIG-82 cells.

FIG. 5 shows that medium conditioned by IRAP$^+$ synoviocytes blocks the induction of neutral metalloproteinases in articular chondrocytes exposed to recombinant human IL-1 beta. Chondrocytes normally secrete 1 U/$10^6$ cells, or less, gelatinase into their culture media. FIG. 5 shows that when to about 5 U/ml or 10 U/ml IL-1 are added, gelatinase production increases to over 4 U and 6 U/$10^8$ cells, respectively. Addition of medium conditioned by MFG-IRAP-infected HIG-82 cells employed by the method of this invention suppressed gelatinase production by IL-1 treated chondrocytes. With 5 U/ml IL-1 (FIG. 5, right panel) inhibition was 100% for one culture and 41% for the other. With 10 U/ml IL-1, inhibition was reduced to 38% and 18% (FIG. 5, left panel) as is expected of a competitive inhibitor. These data demonstrate that the IRAP produced by HIG-82 cells infected with MFG-IRAP is biologically active.

EXAMPLE IX

This example demonstrates the uptake and expression of Lac Z gene by synoviocytes using infection by a liposome (lipofection). A six well plate containing synoviocyte cultures were transduced with the Lac Z gene by lipofection. The content of each well is as follows:

Well 1 Control cells, treated with liposomes alone

Well 2 Control cells, treated with DNA alone

Well 3 DNA+150 nmole liposomes

Well 4 DNA+240 nmole liposomes

Well 5 DNA+300 nmole liposomes

Well 6 DNA+600 nmole liposomes

Figure 6:
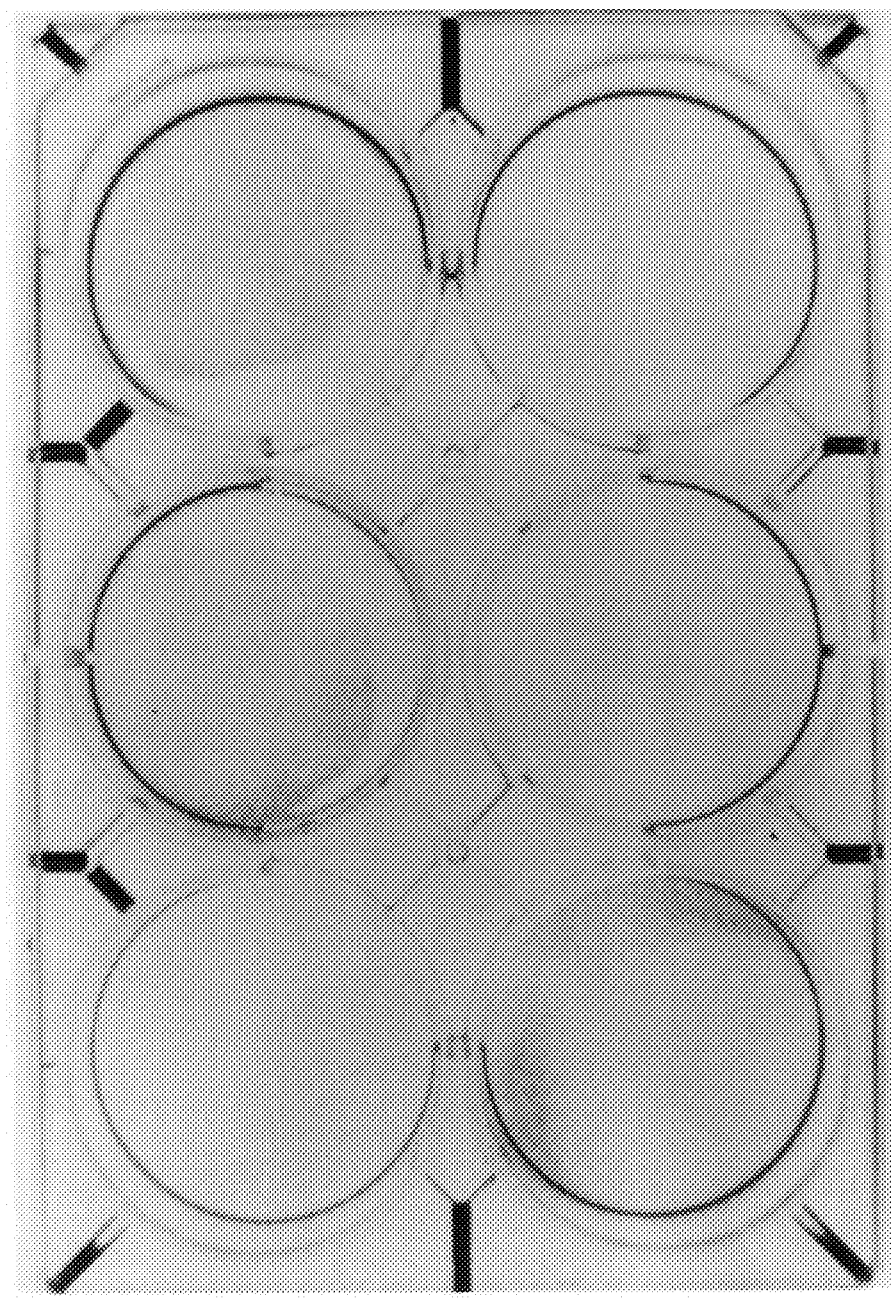
FIG. 6 shows the uptake and expression of the Lac Z gene by synoviocytes using lipofection. Well 1—Control cells, treated with liposomes alone; Well 2—Control cells, treated with DNA alone; Well 3—DNA+150 nmole liposomes; Well 4—DNA+240 nmole liposomes; Well 5—DNA+300 nmole liposomes; Well 6—DNA+600 nmole liposomes.

Wells 3–6 containing sub-confluent cultures of synovial fibroblasts were infected with 6 ug of DNA complexed with 150–600 nmoles/well of "DC-chol" liposome or in the alternative, with "SF-chol". Three days later, cells were stained histochemically for expression of beta-galactosidase (FIG. 6).

Table 1 shows the results of using the liposomes "DC-chol" and "SF-chol" in converting synoviocyte cultures to the Lac Z$^+$ phenotype without selection. Table 1 sets forth that the "DC-chol" liposome in a concentration of about 300 nmole/well converted generally 30% of the synovial cells in synoviocyte cultures to the Lac Z$^+$ phenotype without selection. Reduced expression was shown in Well 6 for "DC-chol" due to the toxic effect of the high liposome concentration.

TABLE 1

| Liposome, nmole/well | % Lac Z⁺ Cells | |
|---|---|---|
| | DC-chol | SP-chol |
| 150 | 10 | 0.5 |
| 240 | 22 | 1.0 |
| 300 | 30 | 2.8 |
| 600 | NA | 3.5 |

In another embodiment of this invention, a gene and method of using this gene provides for the neutralization of interleukin-1. Interleukin-1 is a key mediator of cartilage destruction in arthritis. Interleukin-1 also causes inflammation and is a very powerful inducer of bone resorption. Many of these effects result from the ability of interleukin-1 to increase enormously the cellular synthesis of prostaglandin $E_2$, the neutral proteinases—collagenase, gelatinase, and stromelysin, and plasminogen activator. The catabolic effects of interleukin-1 upon cartilage are exacerbated by its ability to suppress the synthesis of the cartilaginous matrix by chondrocytes. Interleukin-1 is present at high concentrations in synovial fluids aspirated from arthritic joints and it has been demonstrated that intra-articular injection of recombinant interleukin-1 in animals causes cartilage breakdown and inflammation.

Figure 7:
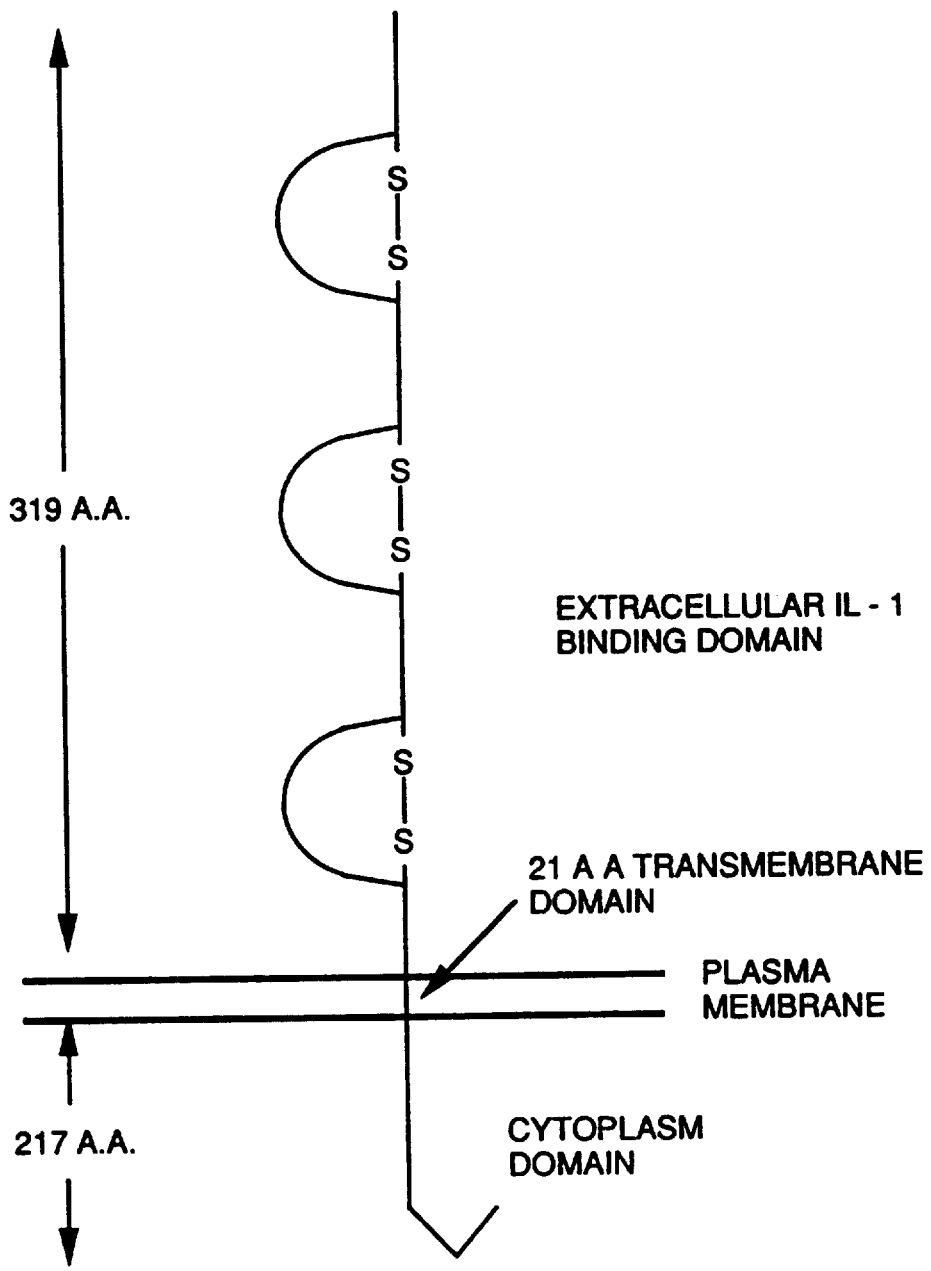
FIG. 7 shows the interleukin-1 binding domain amino acid arrangement.
Figure 8A:
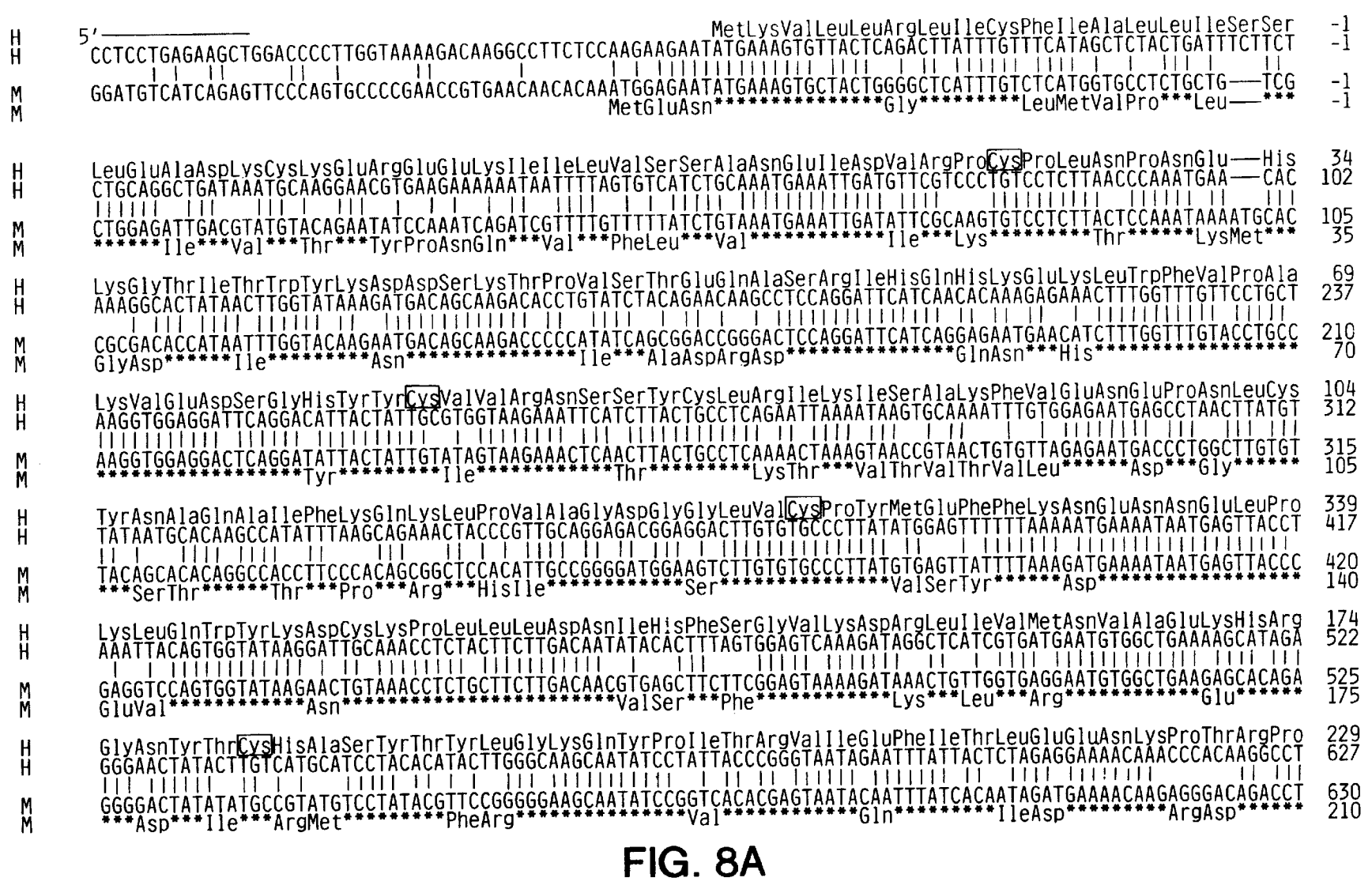
Figure 8B:
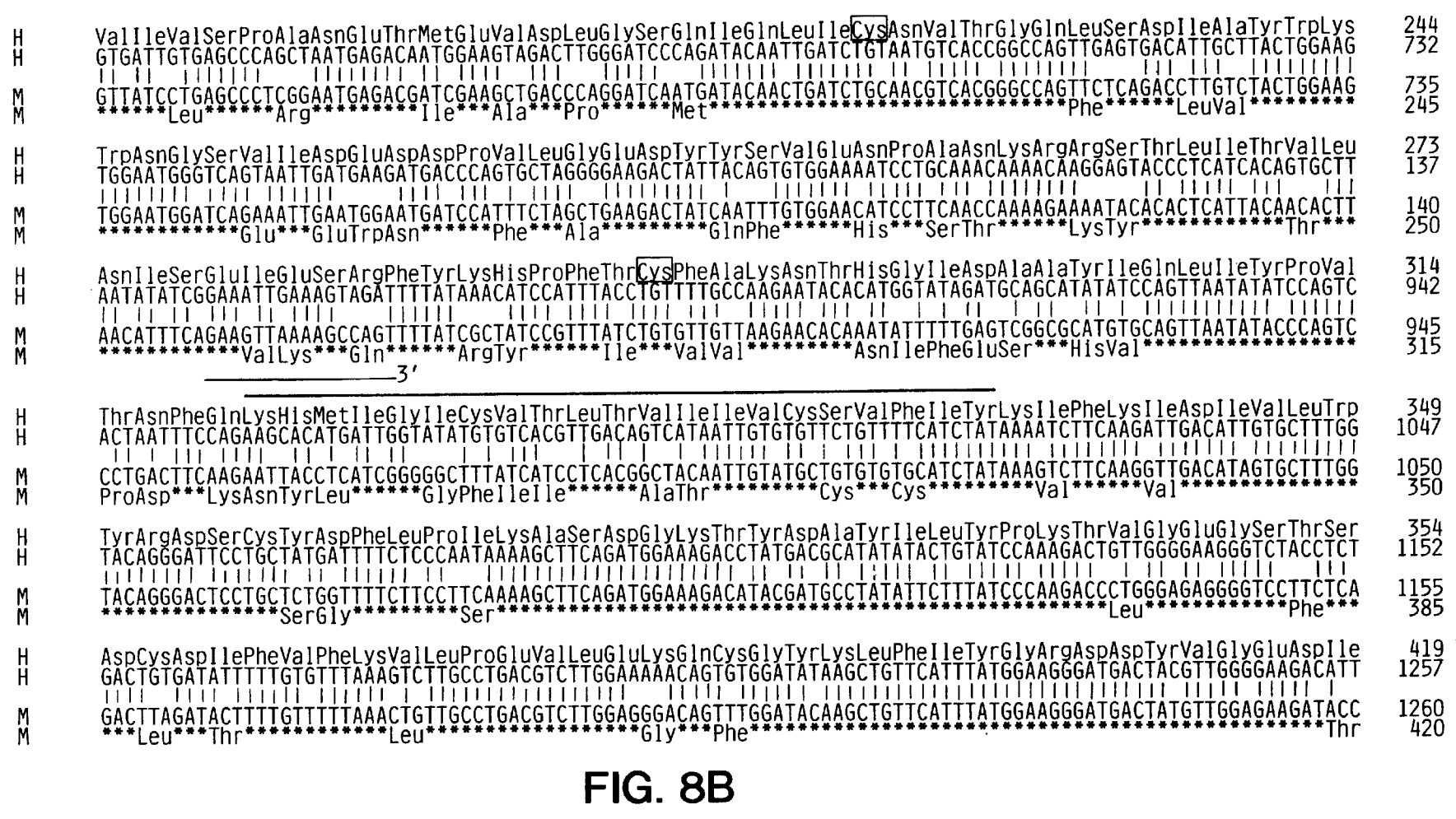

Interleukin-1 exists as several species, such as unglycosylated polypeptide of 17,000 Daltons. Two species have previously been cloned, interleukin-1 alpha and interleukin-1 beta. The alpha form has a pI of approximately 5, and the beta form has a pI around 7. Despite the existence of these isoforms, interleukin-1 alpha and interleukin-1 beta have substantially identical biological properties and share common cell surface receptors. The type I interleukin-1 receptor is a 80 kDa (kilodalton) glycoprotein and contains an extracellular, interleukin-1 binding portion of 319 amino acids which are arranged in three immunoglobulin-like domains held together by disulfide bridges as shown in FIG. 7. A 21 amino acid trans-membrane domain joins the extracellular portion to the 217 amino acid cytoplasmic domain. FIGS. 8A–8C show the amino acid and nucleotide sequence of the human and mouse interleukin-1 receptors. In FIG. 8B, the 21 amino acid trans-membrane region of the interleukin-1 receptor is marked by the thicker solid line. In FIGS. 8A and 8B, the position of the 5' and 3' oligonucleotides for PCR are marked by thinner short lines, respectively. The lysine amino acid just 5' to the trans-membrane domain to be mutated to a stop codon is marked by a solid circle in FIG. 8B.

Synovium is by far the major, and perhaps the only, intra-articular source of interleukin-1 in the arthritic joint. Snyovia recovered from arthritic joints secrete high levels of interleukin-1. Both the resident synoviocytes and infiltrating blood mononuclear cells within the synovial lining produce interleukin-1.

The present invention provides a method of using in vivo a gene coding for a truncated form of the interleukin-1 receptor which retains its ability to bind interleukin-1 with high affinity but which is released extracellularly and therefore inactive in signal transduction. The binding of this truncated and modified receptor to interleukin-1 inhibits the intra-articular activity of interleukin-1.

This method of using a gene encoding the extracellular interleukin-1 binding domain of an interleukin-1 receptor that is capable of binding to and neutralizing interleukin-1 includes employing a retroviral vector carrying a truncated interleukin-1 receptor gene which encodes a truncated and soluble active form of the receptor. The expression of the novel interleukin-1 receptor gene is controlled by regulatory sequences contained within the vector that are active in eukaryotic cells. This recombinant viral vector is transfected into cell lines stably expressing the viral proteins in trans required for production of infectious virus particles carrying the recombinant vector. These viral particles are used to deliver the recombinant interleukin-1 receptor to the recipient synovial cells by direct virus infection in vivo.

Figure 9:
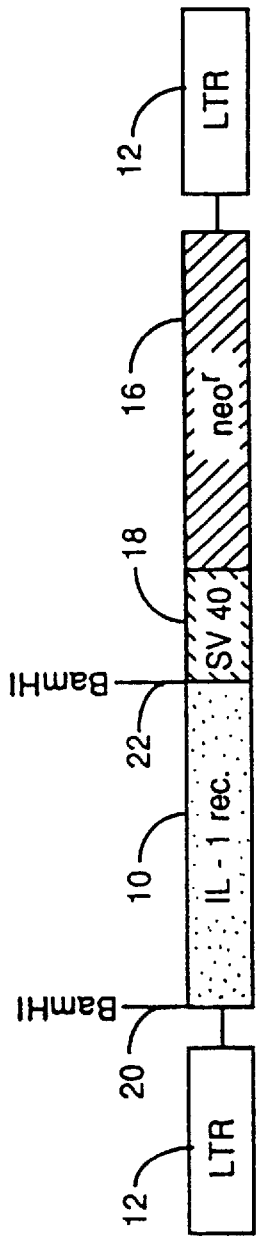
FIG. 9 shows gene encoding a truncated interleukin-1 receptor inserted into a retroviral vector.

The soluble human interleukin-1 receptor to be inserted into the retroviral vector may be generated by a polymerase chain reaction (PCR). An oligonucleotide complementary to the 5' leader sequence of the human interleukin-1 receptor (GCGGATCCCCTCCTAGAAGCT; SEQ ID NO: 5) and an oligonucleotide complementary to a region just upstream from the transmembrane domain of the interleukin-1 receptor (GCGGATCCCATGTGCTACTGG; SEQ ID NO: 6) are used as primers for PCR. The primer for the region of the interleukin-1 receptor adjacent to the trans-membrane domain contains a single base change so that the lys codon at amino acid 336 (AAG) is changed to a stop codon (TAG). By inserting a translation stop codon just upstream from the transmembrane domain, a truncated form of interleukin-1 receptor that is secreted by the cell is generated. A BamHI recognition sequence (GGATCC) is added to the 5' end of the PCR primers, and following amplification, the resulting interleukin-1 receptor fragment is cloned into a BamHI site. A cDNA library from human T-cells is used as a source for the interlelukin-1 receptor cDNA. To amplify the appropriate region of the interleukin-1 receptor from the cDNA library, the complementary primers are added to the DNA and 50 cycles of annealing, primer extension and denaturation are performed using a thermocycler and standard PCR reaction conditions well known by those persons skilled in the art. Following amplification of the interleukin-1 soluble receptor using the PCR process, the resulting fragment is digested with BamHI and inserted into the pLJ retroviral vector. The pLJ retroviral vector is available from A. J. Korman and R. C. Mulligan. See also *Proc. Natl. Acad. Sci.,* Vol. 84, pp. 2150–2154 (April 1987) co-authored by Alan J. Korman, J. Daniel Frantz, Jack L. Strominger and Richard C. Mulligan. Restriction analysis was performed to determine the correct orientation of the insert.

The retrovirus vector carrying the truncated interleukin-1 receptor is transferred into the CRIP (*Proc. Natl. Acad. Sci.,* Vol. 85, pp. 6460–6464 (1988), O. Danos and R. C. Mulligan) packaging cell line using a standard $CaPO_4$ transfection procedure and cells wherein the viral vector is stably integrated and is selected on the basis of resistance to the antibiotic G418. The viral vector containing the neomycin resistant (neo-r) gene is capable of imparting resistance of the cell line to G418. The CRIP cell line expresses the three viral proteins required for packaging the vector viral RNAs into infectious particles. Moreover, the viral particles produced by the CRIP cell line are able to efficiently infect a wide variety of mammalian cell types including human cells. All retroviral particles produced by this cell line are defective for replication but retain the ability to stably integrate into synovial cells thereby becoming an heritable trait of these cells. Virus stocks produced by this method are substantially free of contaminating helper-virus particles and are also non-pathogenic.

More specifically, the truncated interleukin-1 gene can be inserted into a retroviral vector under the regulation of a suitable eukaryotic promoter such as the retroviral promoter already contained within the gene transfer vector, such as for example, the pLJ vector shown in FIG. 9. FIG. 9 shows the structure of the pLJ interleukin receptor retroviral vector and partial restriction endonuclease map. Reference numeral 10 shows the interleukin-1 receptor inserted into a retroviral vector. Reference numeral 12 indicates long terminal repeats (LTR's) at each end of the structure of the pLJ interleukin receptor retroviral vector shown in FIG. 8. These LTR's regulate the viral transcription and expression of the interleukin-1 receptor. Bacterial gene encoding resistance to the antibiotic neomycin (neo-r) is shown at reference numeral 16. The Simian Virus 40 enhancer promoter (SV 40) is indicated at reference numeral 18, and regulates the expression of the neo-r gene. Reference numbers 20 and 22, respectively, show the sites wherein the resulting interleukin receptor fragment is cloned. It will be understood by those persons skilled in the art that other vectors containing different eukaryotic promoters may also be utilized to obtain a generally maximal level of interleukin-1 receptor expression. The vectors containing the truncated, and modified interleukin-1 receptor will be introduced into a retroviral packaging cell line (CRIP) by transfection and stable transformants isolated by selection for the expression of the neomycin resistance gene also carried by the pLJ vector. The CRIP cell line expresses all the proteins required for packaging of the exogenous retroviral RNA. Viral particles produced by the G418-selected CRIP cell lines will carry a recombinant retrovirus able to infect mammalian cells and stably express the interleukin-1 truncated receptor. The viral particles are used to infect synovial cells directly in vivo by injecting the virus into the joint space.

Another embodiment of this invention provides a method for using the hereinbefore described viral particles to infect in culture synovial cells obtained from the lining of the joint of a mammalian host. The advantage of the infection of synovial cells in culture is that infected cells harboring the interleukin-1 receptor retroviral construct can be selected using G418 for expression of the neomycin resistance gene. The infected synovial cells expressing the interleukin-1 receptor can then be transplanted back into the joint by intra-articular injection. The transplanted cells will express high levels of soluble interleukin-1 receptor in the joint space thereby binding to and neutralizing substantially all isoforms of interleukin-1, including interleukin-1 alpha and interleukin-1 beta.

The method used for transplantation of the synovial cells within the joint is a routine and relatively minor procedure used in the treatment of chronic inflammatory joint disease. Although synovium can be recovered from the joint during open surgery, it is now common to perform synovectomies, especially of the knee, through the arthroscope. The arthroscope is a small, hollow rod inserted into the knee via a small puncture wound. In addition to permitting the intra-articular insertion of a fibre-option system, the arthroscope allows access to surgical instruments, such that snyovial tissue can be removed arthroscopically. Such procedures can be carried out under "spinal" anesthetic and the patient allowed home the same day. In this manner sufficient synovium can be obtained from patients who will receive this gene therapy. The synovial cells (synoviocytes) contained within the excised tissue may be aseptically recovered by enzymic digestion of the connective tissue matrix. Generally, the synovium is cut into pieces of approximately 1 millimeter diameter and digested sequentially with trypsin (0.2% w/v in Gey's Balanced Salt Solution) for 30 minutes at 37° Centigrade, and collagenase (0.2% w/v in Gey's Balanced Salt Solution) for 2 hours at 37° Centigrade. Cells recovered from this digestion are seeded into plastic culture dishes at a concentration of $10^4$–$10^5$ cells per square centimeter with Hank's $F_{12}$ medium supplemented with 10% fetal bovine serum and antibiotics. After 3–7 days, the culture medium is withdrawn. Non-adherent cells such as lymphocytes are removed by washing with Gey's Balanced Salt Solution and fresh medium added. The adherent cells can now be used as they are, allowed to grow to confluency or taken through one or more subcultures. Subcultivating expands the cell number and removes non-dividing cells such as macrophages.

Following genetic manipulation of the cells thus recovered, they can be removed from the culture dish by trypsinizing, scraping or other means, and made into a standard suspension. Gey's Balanced Salt Solution or other isotonic salt solutions of suitable composition, or saline solution are suitable carriers. A suspension of cells can then be injected into the recipient mammalian joint. Intra-articular injections of this type are routine and easily carried out in the doctor's office. No surgery is necessary. Very large numbers of cells can be introduced in this way and repeat injections carried out as needed.

Another embodiment of this invention is the gene produced by the hereinbefore described method of preparation. This gene carried by the retrovirus may be incorporated in a suitable pharmaceutical carrier, such as for example, buffered physiologic saline, for parenteral administration. This gene may be administered to a patient in a therapeutically effective dose. More specifically, this gene may be incorporated in a suitable pharmaceutical carrier at a therapeutically effective dose and administered by intra-articular injection. Therefore, the preferred mode regarding the ex vivo method of delivery is the removal of the patients connective tissue (e.g., synovia), in vitro culture of this connective tissue, transduction of the DNA sequence of interest, followed by the above-mentioned manipulation prior to delivery to the afflicted joint of the patient.

In another embodiment of this invention, this gene may be administered to patients as a prophylactic measure to prevent the development of arthritis in those patients determined to be highly susceptible of developing this disease. More specifically, this gene carried by the retrovirus may be incorporated in a suitable pharmaceutical carrier at a prophylactically effective dose and administered by parenteral injection, including intra-articular injection.

EXAMPLE X

Fifty micrograms of a DNA plasmid vector molecule containing the interleukin-1 beta coding sequence ligated downstream of the CMV promoter was encapsulated within cationic liposomes, mixed with Geys biological buffer and injected intra-articularly into the knee joints of a rabbit. Forty eight hours subsequent to injection one nanogram of interleukin-1 beta was recovered from the knee joint area. Therefore, injection of the DNA containing liposome solution within the region of the synovial tissue prompted fusion of the liposomes to the synovial cells, transfer of the DNA plasmid vector into synovial cells and subsequent expression of the IL-1 beta gene. Additionally, it is possible to inject non-encapsulated (i.e., naked) DNA into the joint area and monitor transfection of the DNA vector into the synovial cells as determined by subsequent expression of the IL-1 beta gene in synovial cells. Therefore, either method may be utilized as a plausible alternative to the in vitro manipulation of synovia also exemplified in the present invention.

EXAMPLE XI

Figure 10:
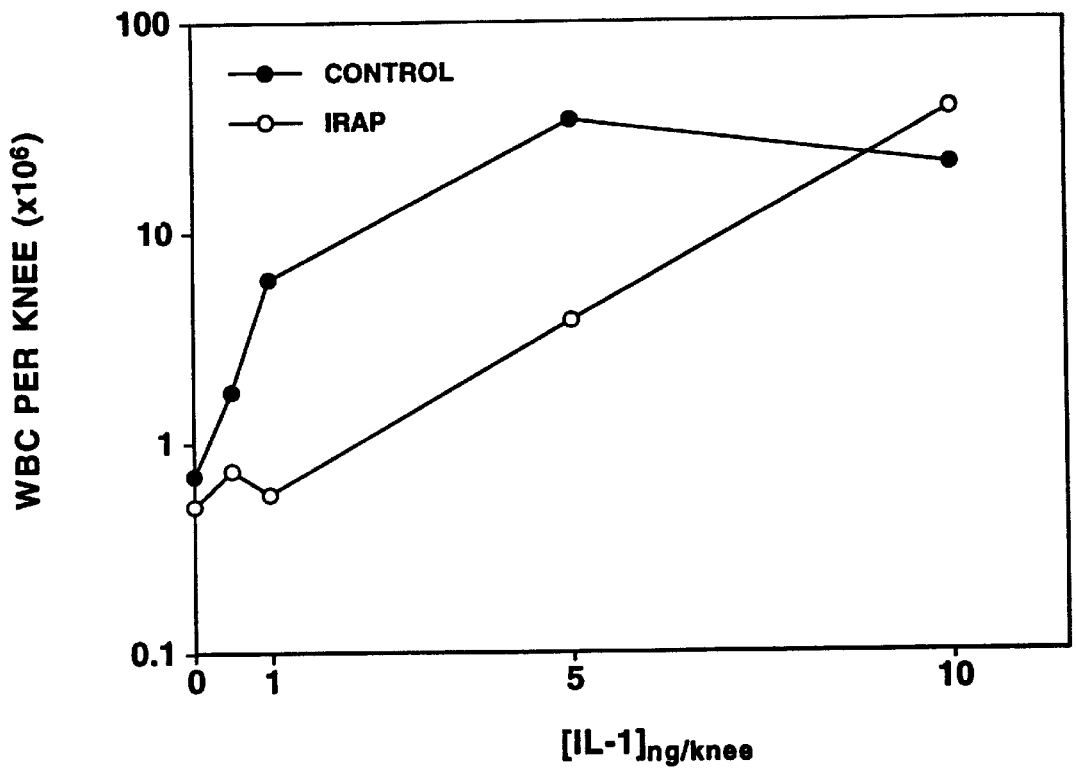
FIG. 10 shows antiinflammatory properties of the MFG-IRAP transgene. MFG-IRAP/HIG-82 cells ($10^7$) or untransduced HIG-82 cells ($10^7$) were transplanted to the knee joints of rabbits 3 days before intraarticular challenge with the indicated amounts of recombinant human interleukin-1 beta (rhIL-1β). Lavage of joints occurred 18 hours later, after which infiltrating leukocytes were counted.

The in vivo biological activity of the MFG-IRAP construct was tested as the ability to suppress the effects of IL-1β. Rabbit knees were injected with recombinant human IL-1β, known to cause an increased concentration of leukocytes within the afflicted joint space. Introduction of MFG-IRAP/HIG-82 cells into rabbit knees strongly suppresses IL-1β production of leukocytes to the afflicted joint space. In contrast, control HIG-82 cells do not suppress the leukocyte infiltration to the joint space challenged with IL-1β (see FIG. 10). Inhibition is greatest at the lowest doses of human recombinant IL-1β (hrIL-1β), as expected by the competitive mechanism through which IRAP antagonizes IL-1. Therefore, this rabbit model confirms that in vivo, intra-articular expression of IRAP is biologically active and can protect the joint from inflammation provoked by IL-1.

EXAMPLE XII

This example further evaluates ex vivo delivery into rabbit knee joints of the MFG-IRAP construct. As known, IRAP is an acidic glycoprotein of approximately 25 kDa that functions as a natural antagonist of the biological actions of interlelukin-1 (IL-1) by binding to IL-1 receptors. Unlike IL-1, IRAP has no agonist activity, instead acting as a competitive inhibitor of the binding of IL-1.

This example shows that in vivo expression of IRAP by genetically modified synovial cells inhibits IL-1β-induced leukocyte infiltration into the joint space, synovial thickening and hypercellularity, and loss of proteoglycans from articular cartilage.

As mentioned within this specification, the preferred mode of treating a patient through the ex vivo route will be by transplanting genetically modified autologous synovial cells by intra-articular injection. However, HIG-82 cells, easily maintained in culture, were used for these experiments to show that intra-articularly expressed IRAP is effective in inhibiting the physiological sequelae of intra-articularly injected IL-1.

MFG-IRAP/HIG-82 cells or control (uninfected HIG-82) cells, were transplanted into rabbit knees by intra-articular injection by the methods disclosed within this specification. Briefly, cultures of these cells were infected with MFG-IRAP. Media conditioned for 3 days by infected MFG-IRAP/HIG 82 cells were assayed for human IRAP by ELISA assay using a commercial kit (R&D Systems, Minneapolis, Minn., U.S.A.) and found to contain approximately 500 ng IRAP/$10^6$ cells. Western blotting confirmed the presence of human IRAP of size 22–25 kDa. HIG-IRAP cells were trypsinized, suspended in Gey's balanced salt solution and 1 ml of suspension, containing $10^7$ cells, was injected intra-articularly into the left knee joints of New Zealand White rabbits (2.5 kg). The contralateral control knees received a similar injection of untransduced HIG-82 cells.

Three days following transplantation of the cells, knee joints were challenged by various doses of a single intra-articular injection of human recombinant IL-1β dissolved in 0.5 ml Gey's solution. Control knees were injected with 0.5 ml of Gey's solution.

Eighteen hours after injection of hrIL-1β, rabbits were killed and the knee joints evaluated histopathologically and for expression of IRAP. Each joint was first lavaged with 1 ml Gey's solution containing 10 mM EDTA. Cell counts in these washings were performed with a hemocytometer. An aliquot was removed for cytospinning and staining with 'DiffQuick' (Baxter Scientific Products) before examination under light microscopy. Washings were then centrifuged. Supernatants were removed for IRAP ELISA and for the determination of glycosaminoglycan (GAG) concentrations as an index of cartilage breakdown. GAG determinations were carried out with the dimethylmethylene blue assay (Farndale, et al., 1986, Biochim Biophys Acta 883: 173–177).

Synovia were dissected from the knee joints, fixed in 70% ethanol, dehydrated, embedded in paraffin, sectioned at 5 μm and stained with hematoxylin and eosin.

Figure 11:
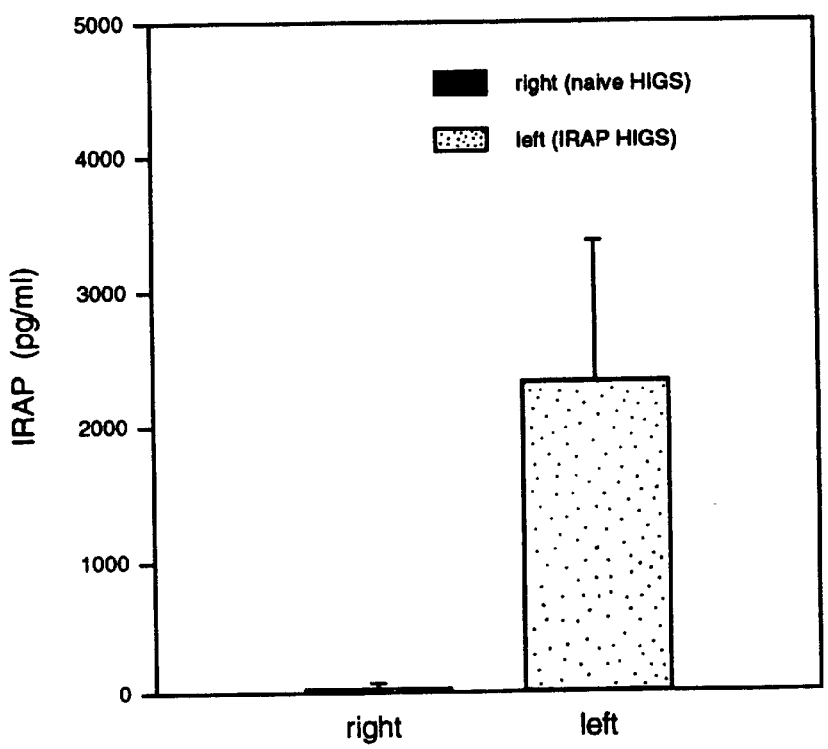
FIG. 11 shows levels of human IRAP in rabbit knees four days following transplant of synoviocytes. Either untransduced (naive) HIG-82 cells or cells carrying a human IRAP gene (MGF-IRAP/HIG-82) were injected intra-articularly in the knee joints or rabbits ($10^7$ cells/knee). Four days later, knees were lavaged and the concentration of human IRAP determined by ELISA. Values given are means+S.D. (n=15).
Figure 12A:
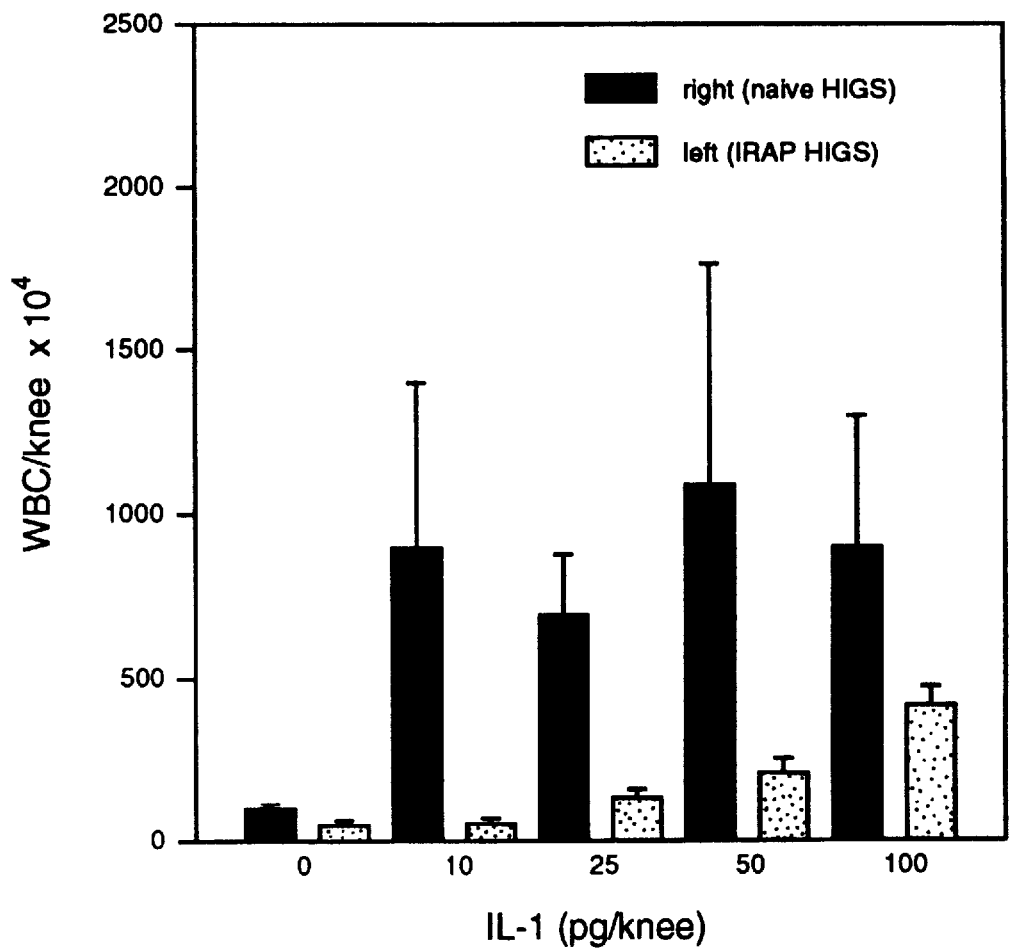
FIGS. 12(A–C) shows inhibition of IL-1 induced leukocyte infiltration in knees expressing IRAP gene. Either naive or IRAP-transduced HIG-82 cells were transplanted into rabbit knee joints, as indicated Three days later 0–100 pg/knee hrIL-1B was intra-articularly injected at the indicated doses. The following day, knee joints were lavaged and the leukocytic infiltrate analyzed by counting with a hemocytometer and by cytospinning. Means+S.E. (n=3). (a) White blood cells (WBC) per knee. (b) Stained cytospin preparation of lavages from control knee injected with IL-1. Preparation was diluted 1:10 prior to cytospinning. (c) Stained cytospin preparation of lavages from IRAP-secreting knee injected with IL-1. The preparation was not diluted.

An average of 2.5 ng human IRAP per knee was measured in joint lavages 4 days following transplant of MFG-IRAP/HIG 82 cells. Contralateral, control knees receiving naive HIG-82 cells had no detectable human IRAP (FIG. 11). To determine whether the observed level of IRAP expression was sufficient to inhibit the effects of IL-1 in vivo, increasing concentrations of IL-1β (0–100 pg) were injected into both the control and IRAP knees. As is shown in FIG. 12a, injection of hrIL-1β into control knees provoked a marked leukocytosis which was strongly suppressed in the genetically modified knees. There was also a statistically significant reduction in the white blood cell count in knees containing MFG-IRAP/HIG 82 cells which had not been injected with IL-1. This may reflect the influence of IRAP upon the slight inflammatory effect of injecting cells into joints. The degree of suppression by IRAP decreased as the amount of injected hrIL-1β increased, in keeping with the competitive mode of inhibition existing between IRAP and IL-1. No dose-response for hrIL-1β alone is evident in these particular experiments because this specific batch of IL-1 was especially effective in eliciting maximal response even at the lowest dose used.

Figure 12B:
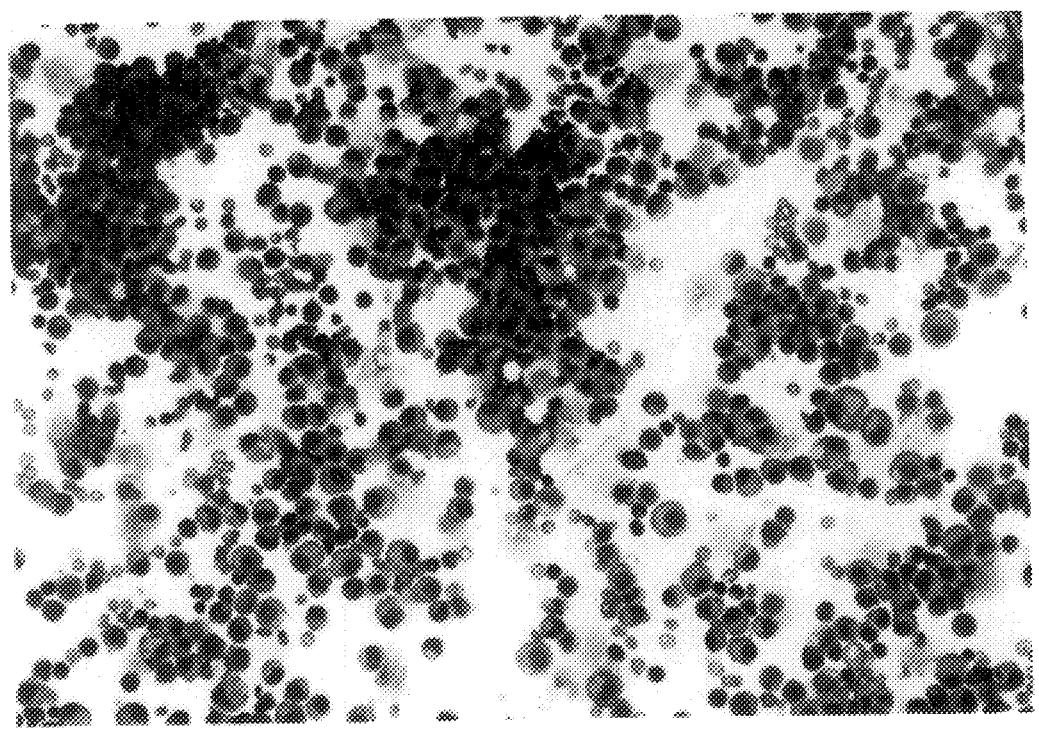
Figure 12C:
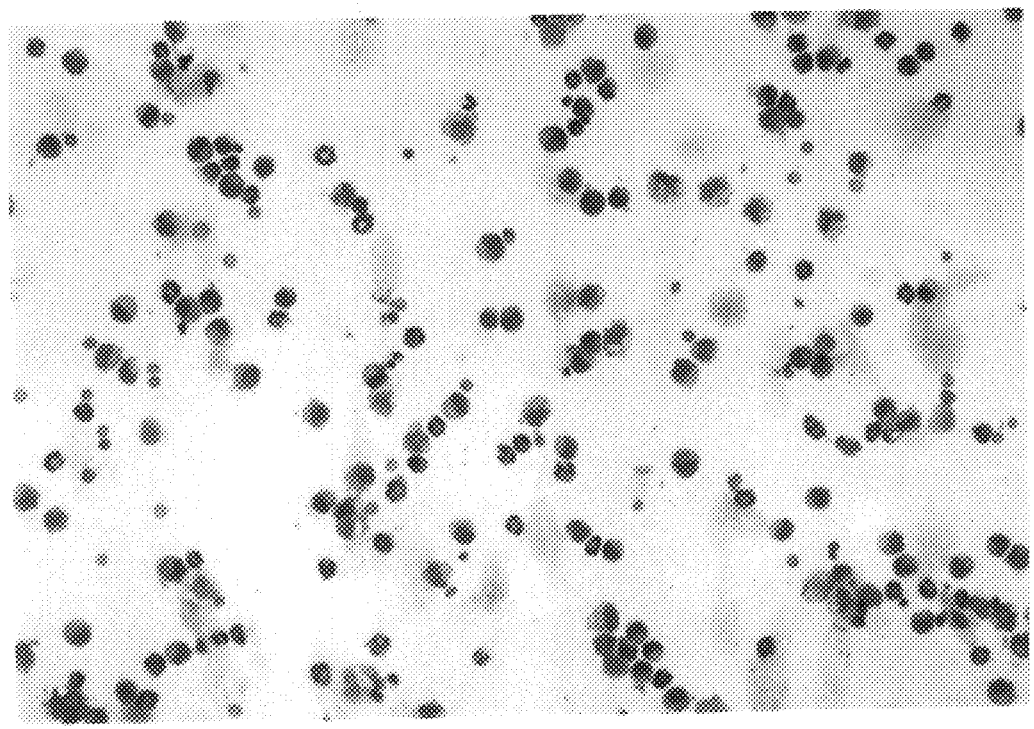

Examination of cytospins (FIGS. 12b, 12c) revealed that most of the infiltrating leukocytes were neutrophils and monocytes. These preparations also serve to illustrate the efficiency with which leukocytosis was suppressed by the IRAP gene. Ten times the volume of lavage fluid is represented on the cytospin obtained from the IRAP-producing knees (FIG. 12c) compared to the non-IRAP knees (FIG. 12b).

Figure 13:
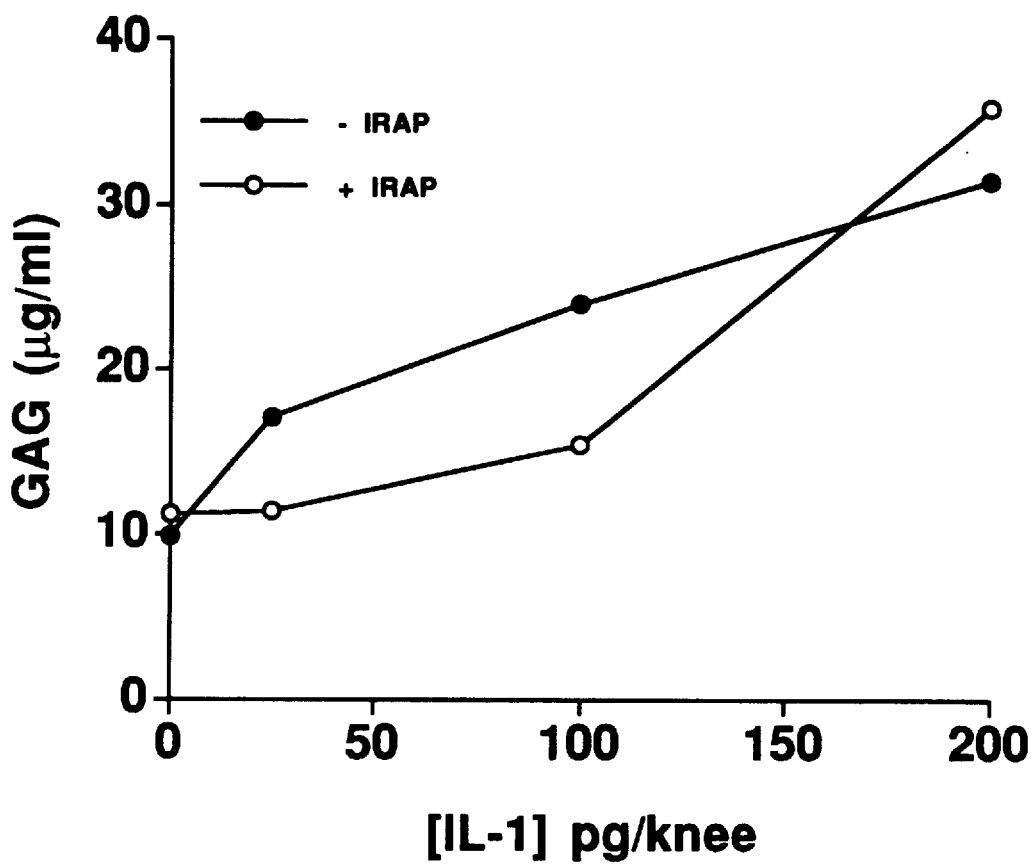
FIG. 13 shows suppression of IL-1 induced loss of proteoglycans from articular cartilage. Either naive or IRAP-transduced HIG-82 cells were transplanted into rabbits knee joints. Three days later, 0–200 pg/knee hrIL-1 was intra-articularly injected at the indicated doses. The following day, knee joints were lavaged and the level of glycosaminoglycans (GAG) as an index of cartilage breakdown was determined.

To determine if intra-articularly expressed IRAP was able to block cartilage breakdown, the concentration of glycosaminoglycans (GAG) in joint lavages was determined. GAG analyses of the washings from the control and IRAP expressing knees (FIG. 13) confirmed that transfer of the IRAP gene partially inhibited breakdown of the cartilaginous matrix in response to IL-1. Again, inhibition was strongest at the lowest concentrations of IL-1 and was abolished at the highest dose of IL-1 (FIG. 13).

Figure 14A:
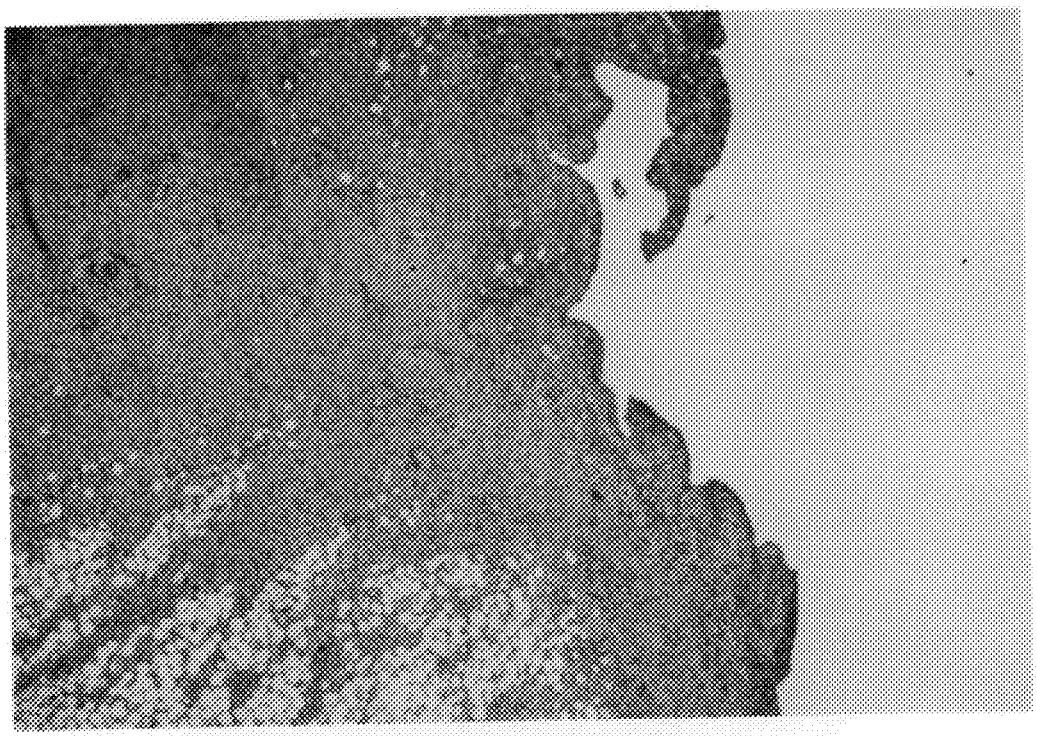
FIGS. 14A–D shows suppression of IL-1 mediated synovial changes in knees expressing IRAP. Ten pg hrIL-1B was injected intra-articularly in each case. Synovia were harvested 18 hours after injection of IL-1β, i.e. 4 days after transplantation of naive or IRAP-secreting HIG-82 cells. (a) Control synovium following injection of IL-1, magnification×10. (b) IRAP-secreting synovium following injection of IL-1, magnification×10. (c) Control synovium following injection of IL-1, magnification×160. (d) IRAP-secreting synovium, magnification+160.
Figure 14B:
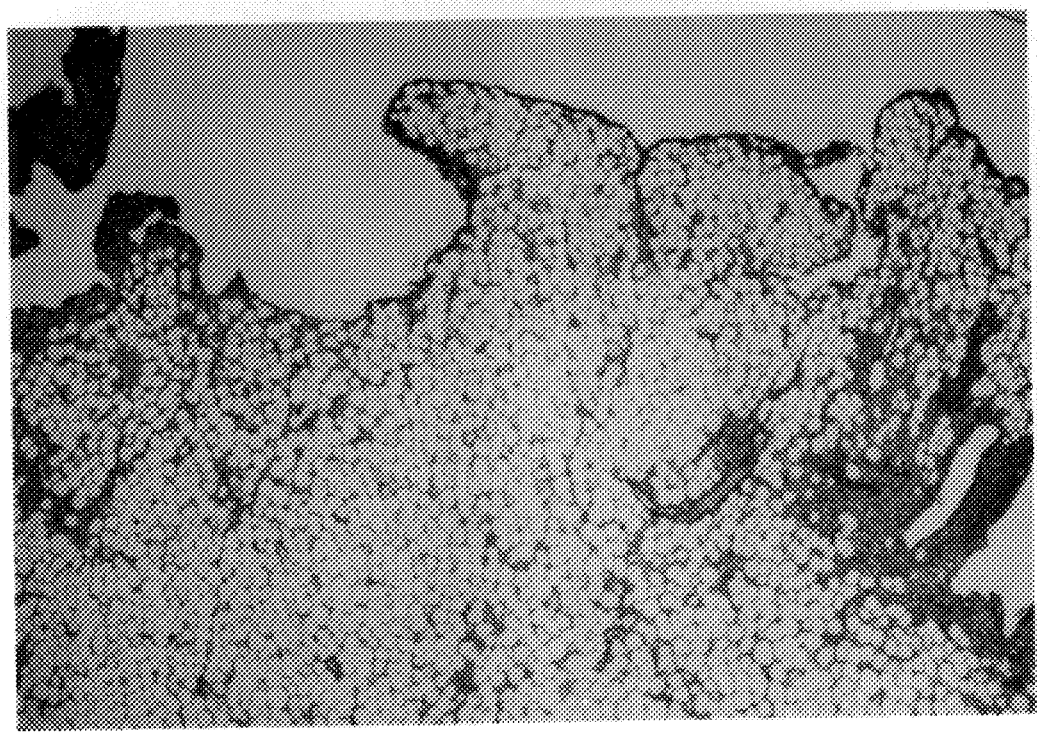
Figure 14C:
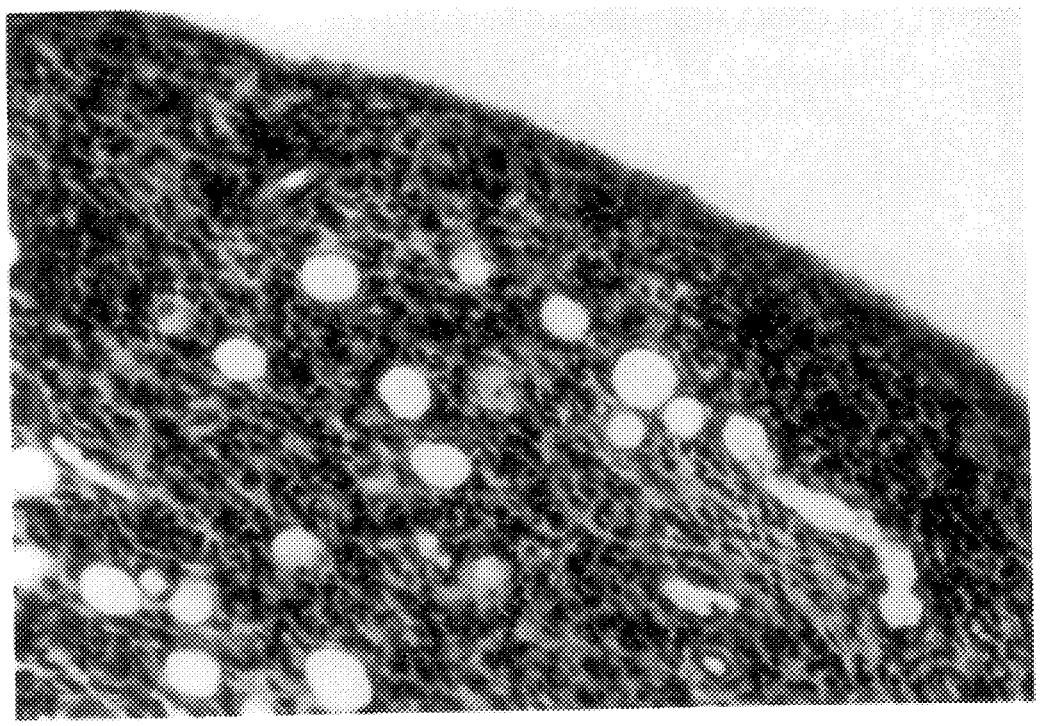
Figure 14D:
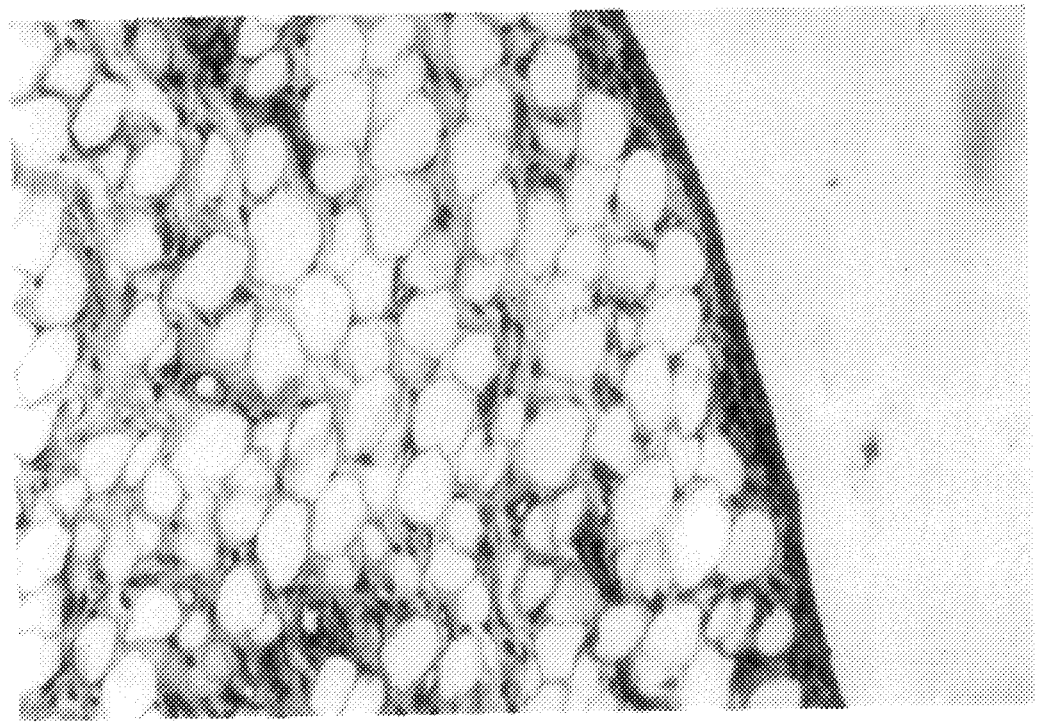

In response to 10 pg of injected hrIL-1β, control synovia became hypertrophic (FIG. 14a) and hypercellular (FIG. 14c). The increased cellularity of the synovia appeared to involve both increased numbers of synoviocytes and infiltration by leukocytes. In knees where MFG-IRAP/HIG 82 cells were present, these changes were completely suppressed and the synovia were nearly indistinguishable from control synovia (FIGS. 14b, 14d).

The ex vivo transfer of the human IRAP gene to the synovial lining of rabbit knees clearly protects these joints from the pathophysiological sequelae of subsequent intra-articular challenge by hrIL-1β.

Measurements of the amounts of IL-1 present in human, recombinant synovial fluids provide values in the range of 0–500 pg/ml (Westacott, et al., 1990, Ann Rheum Dis. 49: 676–681; Malvak, et al., 1993, Arthritis Rheum 36: 781–789). Thus the amounts of IRAP expressed intra-articularly during the present, short-term experiments should be sufficient to block the biological activities of IL-1 at the concentrations present in human arthritic joints.

EXAMPLE XIII

This example shows that the level of intraarticular IRAP expressed subsequent to ex vivo transplantation of synoviocytes transduced with MFG-IRAP is sufficient to inhibit several pathophysiological changes associated with antigen-induced arthritis of the rabbit knee. Intraarticularly expressed IRAP has both a chondroprotective and anti-inflammatory effect during the acute phase of this disease. Data disclosed in Example XII support the contention that the invention as disclosed and claimed is a marked improvement for treating connective tissue disorders such as arthritis in comparison to delivery of proteins to the afflicted joint. Example XII shows that ex vivo transfer of MFG-IRAP to the rabbit knee as disclosed throughout this specification results in the intraarticular accumulation of nanogram quantities of glycosylated, biologically active IRAP. This present example shows that this same gene therapy based product inhibits joint pathologies in a rabbit model of human rheumatoid arthritis.

Young adult rabbits were subjected to a surgical, partial synovectomy of the left knee joint to provide autologous cells. These autologous cells were used to produce cultures of rabbit synovial fibroblasts (type B synoviocytes) from these biopsies as described in Example V and Example IX. Subconfluent cultures were then transduced by infection with MFG–IRAP. Expression of the transgene was confirmed by measuring the concentrations of human IRAP in the conditioned media; values typically range from 100–500 ng IRAP/$10^6$cells/3 days. Sister cultures of synoviocytes from the same animal were infected with a BAG virus encoding the lac Z and neo$^r$ marker genes, and then selected for growth in the presence of G418 (1 mg/ml) to serve as controls. Untransduced synoviocytes were also used as additional controls.

During the period that the cells were being grown and transduced, the donor rabbits were sensitized to ovalbumin by a series of two intradermal injections of 5 mg ovalbumin emulsified in adjuvant, given two weeks apart. Two weeks after the second injection, an acute monarticular arthritis was initiated by the injection of 5 mg ovalbumin dissolved in 1 ml saline into the right knee joints. By this time the left, donor knees had regenerated their synovia, and were each injected with 1 ml saline as controls.

One day after the onset of arthritis, $10^7$ autologous cells, transduced with either the IRAP gene, or lac Z and neo genes, were injected into each arthritic knee, and each contralateral, non-arthritic knee. In other control experiments, knees were injected with untransduced, autologous cells. Groups of rabbits were killed 3 and 7 days later, corresponding to the middle and end of the acute phase of this arthropathy. Knees were lavaged with 1 ml of saline, prior to the removal of synovial tissue and articular cartilage for analysis.

Figure 15:
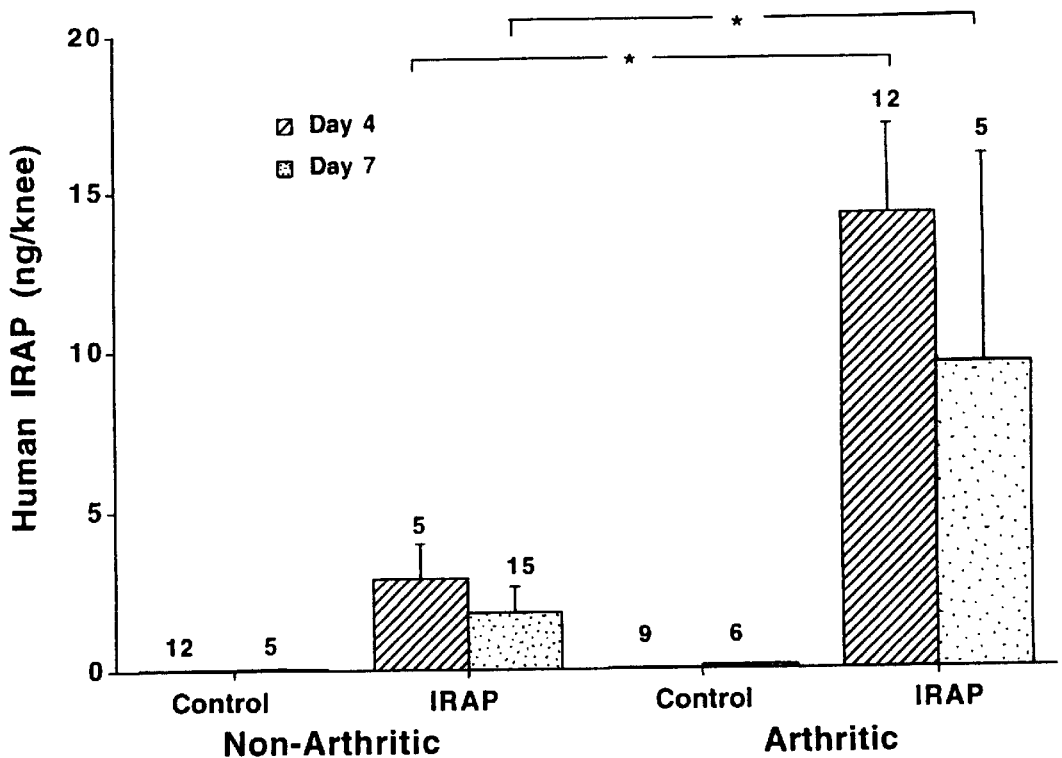
FIG. 15 shows expression of human IRAP in normal and arthritic knees of rabbits. Antigen-induced arthritis was initiated by injecting 5 mg ovalbumin into one knee joint (arthritic knee) of pre-sensitized rabbits on day 1. The contralateral knee (non-arthritic knee) received carrier solution only. On day 2, autologous synoviocytes ($10^7$/knee in 1 ml saline) were transferred to selected knee joints by intraarticular injection. Certain non-arthritic knees and arthritic knees received cells transduced with the human IRAP gene. Other non-arthritic and arthritic knees received untransduced cells or cells transduced with lac Z and neo$^r$ genes (controls). As the results obtained with these two types of control cells were indistinguishable, they have been pooled in the figures. Detailed methods for synoviocyte culture, transduction and intraarticular implantation are disclosed throughout this specification On day 4, knees were lavaged with 1 ml saline. On day 7, rabbits were killed and the knees again lavaged. The concentrations of human IRAP in the lavage fluids were determined by ELISA using a commercial kit (R&D Systems, Minneapolis, Minn.). Values given are means±S.E. Numbers of knees are shown above each column. Asterisks denote values which differ at p<0.05 (t-test).

Intraarticular expression of the MFG-IRAP transgene was evaluated by ELISA measurements of human IRAP in the lavage fluids. IRAP concentrations in the control, non-arthritic knees is shown in FIG. 15. IRAP concentrations in the arthritic knees were always several-fold higher than in normal knees at both time points (FIG. 15). In both non-arthritic and arthritic knees transduced with MFG-IRAP, there was a slight decrease in IRAP expression with time. No human IRAP could be detected in sera obtained from normal or arthritic rabbits.

Figure 16:
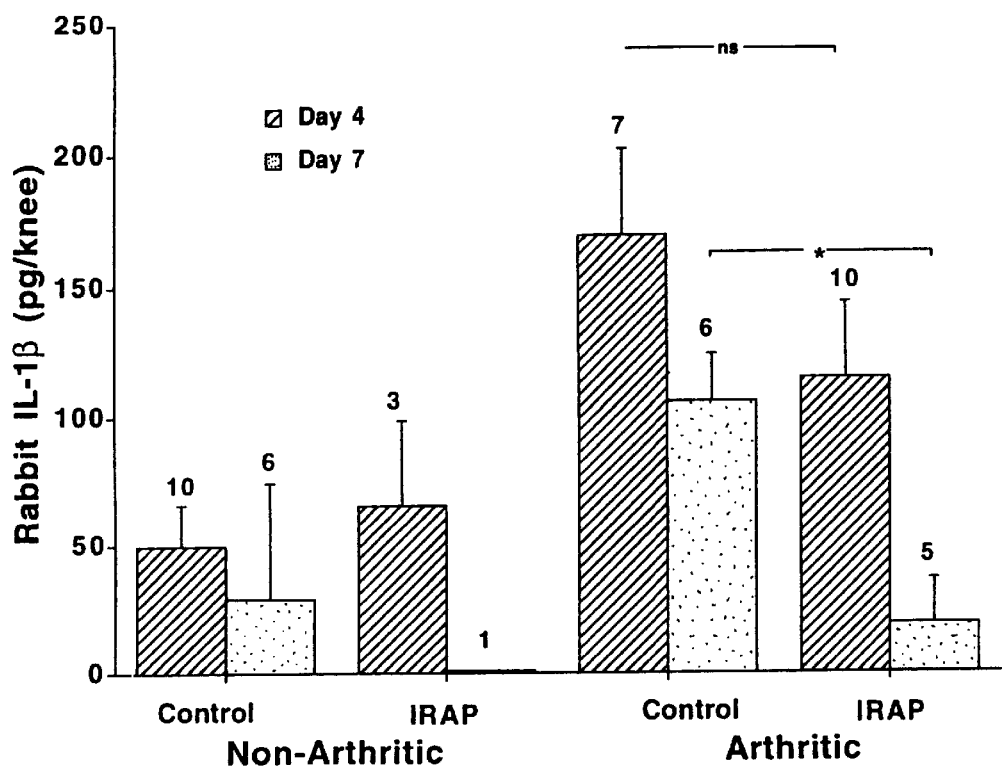
FIG. 16 shows concentrations of rabbit IL-1β in the normal and arthritic knee joints of rabbits. Experimental conditions were identical to those described in FIG. 15. However, lavage fluids were assayed for rabbit IL-1α and rabbit IL-1β by RIA using a commercial kit (Cytokine Sciences, Boston, Mass.). Low levels of IL-1α are present in non-arthritic knees as a reflection of the slight inflammatory effects provoked by intraarticular injection. No IL-1α was detectable in any of the samples. Values given are means±S.E. Numbers of knees are shown above each column. Asterisks denote values which differ at p<0.05 (t-test).

During the course of these experiments, the intraarticular concentration of rabbit IL-1 in arthritic knees was in the range of 100–200 pg/knee (FIG. 16). No IL-1α could be detected by RIA of the lavage fluids. Thus the concentration of IRAP within these knees exceeded the concentration of IL-1 by factors of approximately 10–50. Concentrations of IL-1 were lower in day 7 arthritic knees receiving the IRAP gene (FIG. 16), suggesting that IRAP had inhibited an autocrine amplification loop.

Two major pathologies predominate in the rheumatoid joint: loss of articular cartilage and inflammation. The former occurs through a combination of reduced synthesis and enhanced degradation of the cartilaginous matrix. Whereas inflammation is manifest as a synovitis accompanied by influx of leukocytes into the joint space.

Figure 17A:
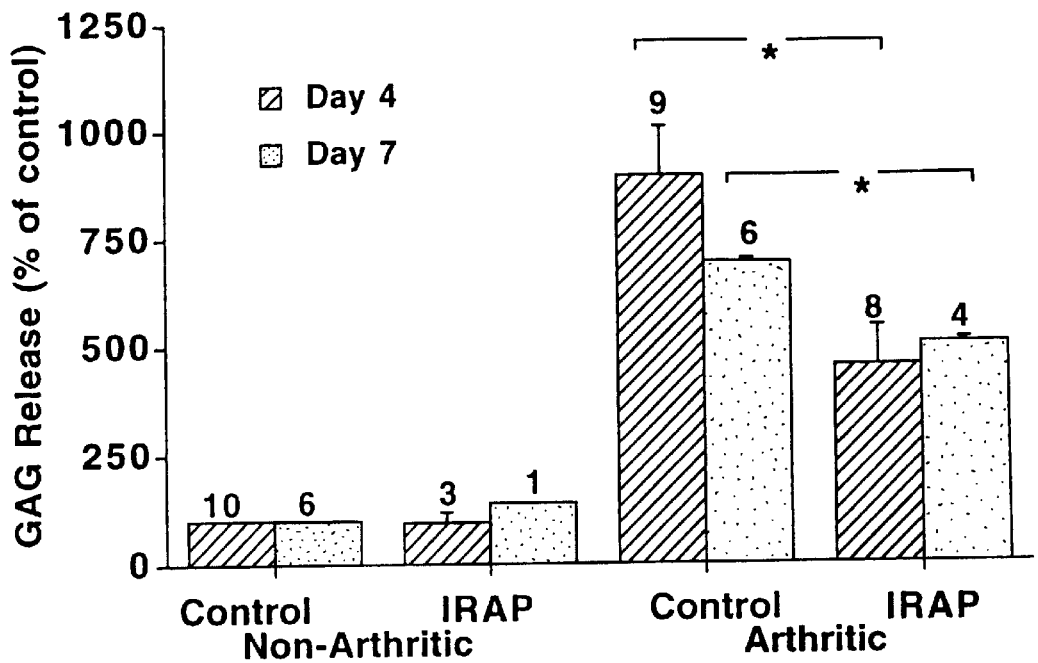
FIGS. 17A–B shows the effect of IRAP gene transfer on cartilage matrix metabolism. Experimental conditions were as described for FIG. 15, except that rabbits were killed both at days 4 and 7. GAG concentrations in the lavage fluids (FIG. 17a) were measured spectrophotometrically by the dimethymethylene blue assay (Farndale, et al., 1986, Biochim. Biophy. Acta 883: 173–177). Fragments of articular cartilage were shaved from the femoral condyles of the knees and GAG synthesis (FIG. 17b) was measured as the uptake of $^{35}SO_4^{2-}$ into macromolecular material as described (Taskiran, et al., 1994, Biophys. Res. Commun. 200:142–148). Results are shown in each case as percent of control. Values given are means±S.E. Numbers of knees are shown above each column.
Figure 17B:
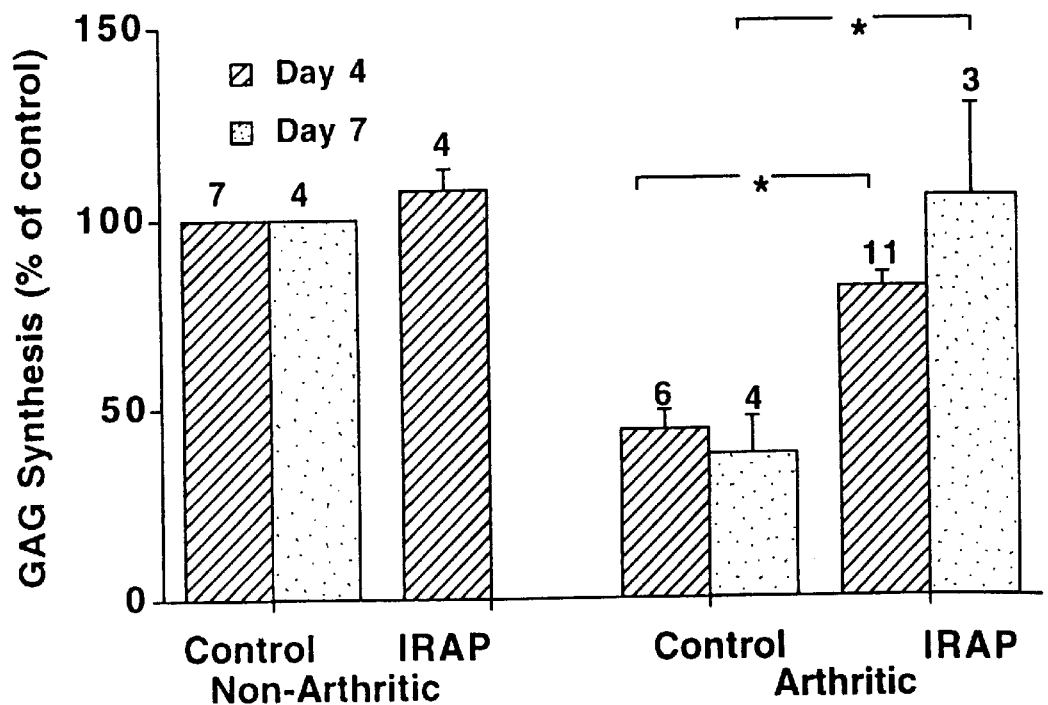
Figure 18:
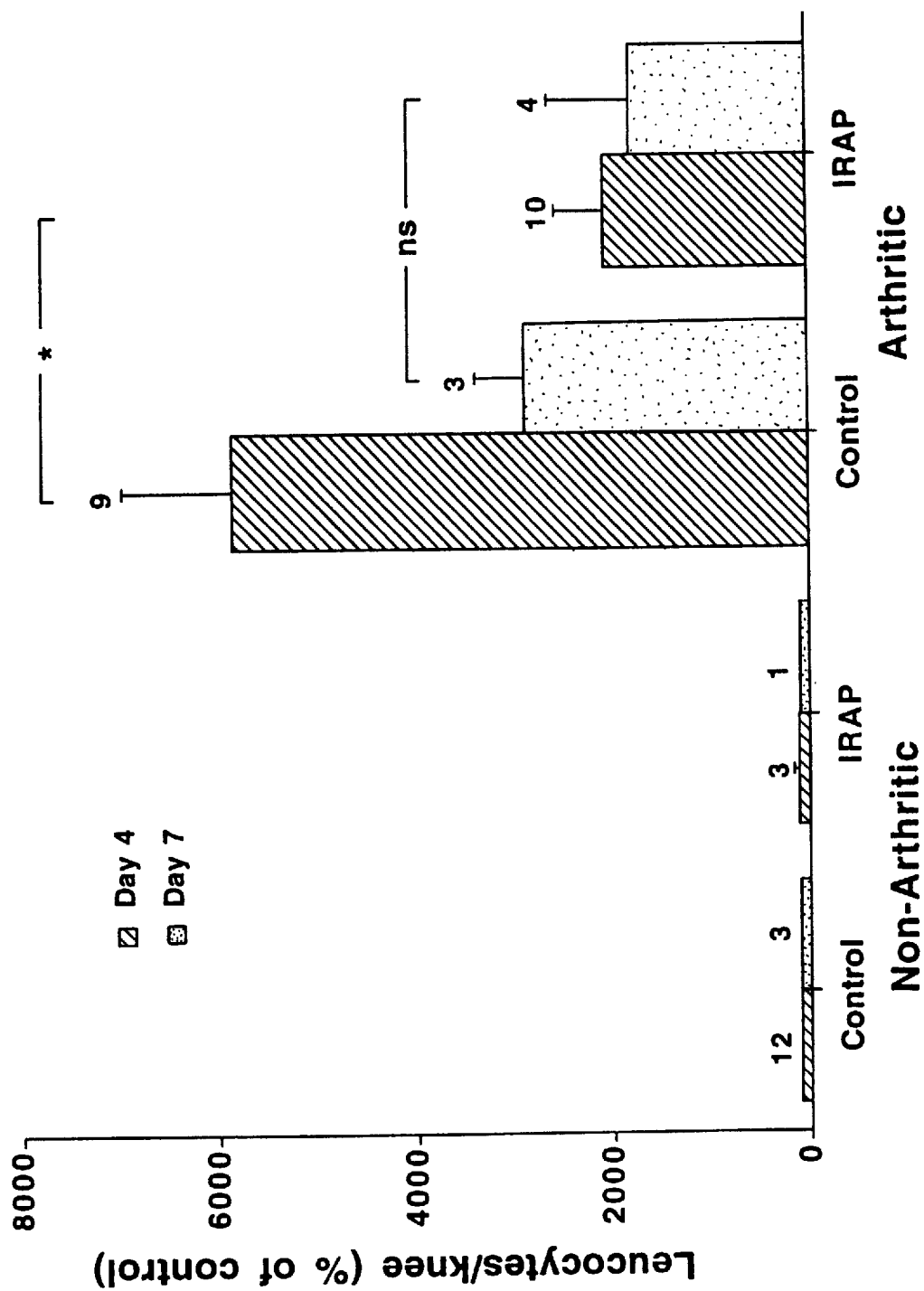
FIG. 18 shows effects of IRAP gene transfer on leucocytosis. Experiment conditions were identical to those described in FIG. 15. Numbers of leukocytes in the lavage fluids were determined with a hemocytometer. Values shown are means±S.E.

The onset of antigen-induced arthritis in this Example was accompanied by cartilage destruction, as reflected in the increased glycosaminoglycan (GAG) content of the lavage fluids (FIG. 17a), and reduced synthesis of cartilage proteoglycans, as reflected by lower uptake of $^{35}SO_4^{2-}$ (FIG. 17b). Knees expressing the MFG-IRAP transgene, but not control knees, were substantially protected from these changes. GAG release (FIG. 17a) was inhibited 55% on day 4 and 32% on day 7. Suppression of GAG synthesis (FIG. 17b) was inhibited by 68% on day 4 and 100% on day 7. The MFG-IRAP transgene also strongly reduced the influx of leukocytes into the joint space (FIG. 18), an effect that was stronger at day 4 (65% inhibition) than at day 7 (38% inhibition); indeed, the difference at day 7 failed to reach statistical significance.

The MFG-IRAP construct is utilized to exemplify the presently claimed invention. In addition to this construct, the ex vivo based teachings of this specification have been utilized to transfer to synovial cells and express in vivo DNA sequences encoding human IL-1α, human TNF-α soluble receptor, vIL-10, Lac Z and neo$^r$.

EXAMPLE XIV

The methods disclosed throughout this specification were utilized to express MFG-human IL-1 soluble receptor type I and type II constructs (with neo$^r$) within in vitro cultured synoviocytes. These transfected synoviocytes produce 1–2 ng/$10^6$ cells of IL-1 soluble receptor types I and II, following neo-selection. The additional methods disclosed throughout this specification may be utilized to procure in vivo expression data regarding these MFG-human IL-1 soluble receptor type I and type II constructs.

EXAMPLE XV

Rabbits were injected intraarticularly in one knee joint with a specific viral or non-viral vector disclosed in Table II. Contralateral knees were injected with a control, usually with the identical viral or non-viral vector with a different passenger gene. At intervals from 2 days to 2 weeks following intraarticular injection, rabbits were sacrificed and the knee joints harvested and stained with X-Gal to assay for LacZ expression. The results are depicted in Table II. The recombinant adenovirus vector comprising a CMV-LacZ fusion and the recombinant HSV vector comprising a CMV-LacZ fusion generated the highest expression level subsequent to intraarticular injection. The recombinant retroviral vector, MFG-LacZ, was not expressed in vivo, lending credence to the concept that retroviral vectors require actively dividing cells during the infection process and the concomitant low mitotic activity of synoviocytes in the joint lining.

However, an intra-articular injection of MFG-IRAP to synovial cells of an inflamed joint space supported retroviral transduction. Injection of MFG-IRAP into an inflamed rabbit knee lead to the intrarticular accumulation of 414.7 pg/knee at 24 hours post injection. The contralateral knee contained only 46.05 pg of human IRAP, close to background level.

TABLE II

| VECTOR | PROMOTER | In Vitro LAC Z cells (%) | In Vivo LEVEL | DURATION (Days) |
|---|---|---|---|---|
| Retrovirus (MFG) | LTR | 20–30 | 0 | 0 |
| HSV | CMV | 1 (toxic) | +++ | 5–7 |
| Adenovirus | CMV | 100 | +++ | ≧14 |

TABLE II-continued

| VECTOR | PROMOTER | EXPRESSION | | |
|---|---|---|---|---|
| | | In Vitro LAC Z cells (%) | In Vivo LEVEL | DURATION (Days) |
| Liposome (DC-chol) | CMV | 20–30 | + | 1–2 |
| None (naked DNA) | CMV | 0 | ± | 1–2 |

Level of in vivo expression was evaluated subjectively on a scale of 0–+++, based upon the degree of staining with X-Gal.
LTR = viral long terminal repeat
CMV = cytomegalovirus These data demonstrate that the gene therapy methods disclosed and claimed in the present invention can be used to modulate the disease process in an animal model of arthritis. In turn, these Examples enable the claimed gene therapy based treatment of connective tissue pathologies and systemic indices of inflammation within the afflicted joint (s). It will be appreciated by those skilled in the art that this invention provides a method of introducing into a connective tissue cell of a mammalian host in vitro, or in the alternative in vivo, at least one gene which codes for proteins with therapeutic properties. This method includes employing genes having DNA that is capable of maintenance and expression.

It will be appreciated by those skilled in the art that this invention provides a method of introducing at least one gene encoding a product into at least one cell of the connective tissue of a mammalian host for treating an arthritic condition of the mammalian host.

It will be understood by those skilled in the art that this invention provides a method to repair and regenerate the connective tissue of a mammalian host.

It will be further understood that the present invention discloses ex vivo and in vivo techniques for delivery of a DNA sequence of interest to the connective tissue cells of the mammalian host. The ex vivo technique involves prior removal and culture of target autologous connective tissue cells, in vitro infection of the DNA sequence, DNA vector or other delivery vehicle of interest into the connective tissue cells, followed by transplantation to the modified connective tissue cells to the target joint of the mammalian host, so as to effect in vivo expression of the gene product of interest. The in vivo technique bypasses the requirement for in vitro culture of target connective tissues cells; instead relying on direct transplantation of the DNA sequence, DNA vector or other delivery vehicle to the target in vivo connective tissue cells, thus effecting expression of the gene product of interest.

It will be further understood that this invention provides a method to produce an animal model for the study of connective tissue pathology.

It will be appreciated by those persons skilled in the art that this invention provides a method of using and a method of preparing a gene encoding an extracellular interleukin-1 binding domain of an interleukin-1 receptor that is capable of binding to and neutralizing substantially all isoforms of interleukin-1, and thus substantially protect cartilage of a mammalian host from pathological degradation. In addition, it will be understood by those persons skilled in the art that the method of using the gene of this invention will reduce inflammation, protect soft tissues of the joint and suppress the loss of bone that occurs in patients suffering with arthritis.

It will be appreciated by those persons skilled in the art that the viral vectors employed in the hereinbefore described invention may be employed to transfect synovial cells in vivo or in culture, such as by direct intra-articular injection or transplantation of autologous synovial cells from the patient transduced with the retroviral vector carrying the truncated interleukin-1 receptor gene.

It will also be understood that a class of DNA sequences, as described throughout this specification, including but not limited to IRAP, may use the claimed methods to effect reduction of inflammation, protect soft tissues of the joint and suppress the loss of bone that occurs in patients suffering with arthritis.

Whereas particular embodiments of this invention have been described above for purposes of illustration, it will be evident to those persons skilled in the art that numerous variations of the details of the present invention may be made without departing from the invention as defined in the appended claims.

What is claimed is:

1. A method of treating arthritis comprising:

a) generating a recombinant viral vector comprising a DNA sequence encoding interleukin-1 receptor antagonist protein operatively linked to a promoter;

b) infecting in vitro a population of autologous cultured synovial cells with said recombinant viral vector, resulting in a population of transfected synovial cells; and c) transplanting said transfected synovial cells by intraarticular injection to an arthritic joint space of a mammalian host, such that expression of said DNA sequence within said joint space results in a reduction of cartilage destruction or a reduction in synovitis.

2. The method of claim 1 wherein said recombinant viral vector is a retroviral vector.

3. The method of claim 2 wherein said recombinant retroviral vector is MFG-IRAP.

4. The method of claim 1 wherein said population of transfected synovial cells are stored prior to transplantation.

5. The method of claim 4 wherein said population of transfected synovial cells are stored in 10% DMSO under liquid nitrogen prior to transplantation.

6. A method of treating arthritis comprising:

a) generating a recombinant plasmid vector comprising a DNA sequence encoding interleukin-1 receptor antagonist protein operatively linked to a promoter;

b) transforming in vitro a population of autologous cultured synovial cells with said recombinant plasmid vector, resulting in a population of transformed synovial cells; and c) transplanting said transformed synovial cells by intraarticular injection to an arthritic joint space of a mammalian host, such that expression of said DNA sequence within said joint space results in a reduction of cartilage destruction or a reduction in synovitis.

7. The method of claim 6 wherein said transforming step is accomplished by a means selected from the group consisting of liposome encapsulation, calcium phosphate, electroporation and DEAE-dextran.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1770 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
        ( A ) LIBRARY: Human T-cell cDNA Library
        ( B ) CLONE: Human Interleukin-1 Receptor ( i x ) FEATURE:

-continued (A) NAME/KEY: CDS
(B) LOCATION: 55..1764

(xi) SEQUENCE DESCRIPTION: SEQ ID NO:1:

| | | | | | |
|---|---|---|---|---|---|
| CCTCCTGAGA AGCTGGACCC CTTGGTAAAA GACAAGGCCT TCTCCAAGAA GAAT ATG | | | | | 57 |
| | | | | Met | |
| | | | | 1 | |

| AAA | GTG | TTA | CTC | AGA | CTT | ATT | TGT | TTC | ATA | GCT | CTA | CTG | ATT | TCT | TCT | 105 |
| Lys | Val | Leu | Leu | Arg | Leu | Ile | Cys | Phe | Ile | Ala | Leu | Leu | Ile | Ser | Ser | |
| | | | 5 | | | | 10 | | | | | 15 | | | | |

| CTG | GAG | GCT | GAT | AAA | TGC | AAG | GAA | CGT | GAA | GAA | AAA | ATA | ATT | TTA | GTG | 153 |
| Leu | Glu | Ala | Asp | Lys | Cys | Lys | Glu | Arg | Glu | Glu | Lys | Ile | Ile | Leu | Val | |
| | | | 20 | | | | 25 | | | | | 30 | | | | |

| TCA | TCT | GCA | AAT | GAA | ATT | GAT | GTT | CGT | CCC | TGT | CCT | CTT | AAC | CCA | AAT | 201 |
| Ser | Ser | Ala | Asn | Glu | Ile | Asp | Val | Arg | Pro | Cys | Pro | Leu | Asn | Pro | Asn | |
| | | 35 | | | | | 40 | | | | | 45 | | | | |

| GAA | CAC | AAA | GGC | ACT | ATA | ACT | TGG | TAT | AAA | GAT | GAC | AGC | AAG | ACA | CCT | 249 |
| Glu | His | Lys | Gly | Thr | Ile | Thr | Trp | Tyr | Lys | Asp | Asp | Ser | Lys | Thr | Pro | |
| 50 | | | | | 55 | | | | | 60 | | | | | 65 | |

| GTA | TCT | ACA | GAA | CAA | GCC | TCC | AGG | ATT | CAT | CAA | CAC | AAA | GAG | AAA | CTT | 297 |
| Val | Ser | Thr | Glu | Gln | Ala | Ser | Arg | Ile | His | Gln | His | Lys | Glu | Lys | Leu | |
| | | | | 70 | | | | | 75 | | | | | 80 | | |

| TGG | TTT | GTT | CCT | GCT | AAG | GTG | GAG | GAT | TCA | GGA | CAT | TAC | TAT | TGC | GTG | 345 |
| Trp | Phe | Val | Pro | Ala | Lys | Val | Glu | Asp | Ser | Gly | His | Tyr | Tyr | Cys | Val | |
| | | | 85 | | | | 90 | | | | | 95 | | | | |

| GTA | AGA | AAT | TCA | TCT | TAC | TGC | CTC | AGA | ATT | AAA | ATA | AGT | GCA | AAA | TTT | 393 |
| Val | Arg | Asn | Ser | Ser | Tyr | Cys | Leu | Arg | Ile | Lys | Ile | Ser | Ala | Lys | Phe | |
| | | 100 | | | | | 105 | | | | | 110 | | | | |

| GTG | GAG | AAT | GAG | CCT | AAC | TTA | TGT | TAT | AAT | GCA | CAA | GCC | ATA | TTT | AAG | 441 |
| Val | Glu | Asn | Glu | Pro | Asn | Leu | Cys | Tyr | Asn | Ala | Gln | Ala | Ile | Phe | Lys | |
| | | 115 | | | | | 120 | | | | | 125 | | | | |

| CAG | AAA | CTA | CCC | GTT | GCA | GGA | GAC | GGA | GGA | CTT | GTG | TGC | CCT | TAT | ATG | 489 |
| Gln | Lys | Leu | Pro | Val | Ala | Gly | Asp | Gly | Gly | Leu | Val | Cys | Pro | Tyr | Met | |
| 130 | | | | | 135 | | | | | 140 | | | | | 145 | |

| GAG | TTT | TTT | AAA | AAT | GAA | AAT | AAT | GAG | TTA | CCT | AAA | TTA | CAG | TGG | TAT | 537 |
| Glu | Phe | Phe | Lys | Asn | Glu | Asn | Asn | Glu | Leu | Pro | Lys | Leu | Gln | Trp | Tyr | |
| | | | | 150 | | | | | 155 | | | | | 160 | | |

| AAG | GAT | TGC | AAA | CCT | CTA | CTT | CTT | GAC | AAT | ATA | CAC | TTT | AGT | GGA | GTC | 585 |
| Lys | Asp | Cys | Lys | Pro | Leu | Leu | Leu | Asp | Asn | Ile | His | Phe | Ser | Gly | Val | |
| | | | 165 | | | | | 170 | | | | | 175 | | | |

| AAA | GAT | AGG | CTC | ATC | GTG | ATG | AAT | GTG | GCT | GAA | AAG | CAT | AGA | GGG | AAC | 633 |
| Lys | Asp | Arg | Leu | Ile | Val | Met | Asn | Val | Ala | Glu | Lys | His | Arg | Gly | Asn | |
| | | 180 | | | | | 185 | | | | | 190 | | | | |

| TAT | ACT | TGT | CAT | GCA | TCC | TAC | ACA | TAC | TTG | GGC | AAG | CAA | TAT | CCT | ATT | 681 |
| Tyr | Thr | Cys | His | Ala | Ser | Tyr | Thr | Tyr | Leu | Gly | Lys | Gln | Tyr | Pro | Ile | |
| | 195 | | | | | 200 | | | | | 205 | | | | | |

| ACC | CGG | GTA | ATA | GAA | TTT | ATT | ACT | CTA | GAG | GAA | AAC | AAA | CCC | ACA | AGG | 729 |
| Thr | Arg | Val | Ile | Glu | Phe | Ile | Thr | Leu | Glu | Glu | Asn | Lys | Pro | Thr | Arg | |
| 210 | | | | | 215 | | | | | 220 | | | | | 225 | |

| CCT | GTG | ATT | GTG | AGC | CCA | GCT | AAT | GAG | ACA | ATG | GAA | GTA | GAC | TTG | GGA | 777 |
| Pro | Val | Ile | Val | Ser | Pro | Ala | Asn | Glu | Thr | Met | Glu | Val | Asp | Leu | Gly | |
| | | | | 230 | | | | | 235 | | | | | 240 | | |

| TCC | CAG | ATA | CAA | TTG | ATC | TGT | AAT | GTC | ACC | GGC | CAG | TTG | AGT | GAC | ATT | 825 |
| Ser | Gln | Ile | Gln | Leu | Ile | Cys | Asn | Val | Thr | Gly | Gln | Leu | Ser | Asp | Ile | |
| | | | 245 | | | | | 250 | | | | | 255 | | | |

| GCT | TAC | TGG | AAG | TGG | AAT | GGG | TCA | GTA | ATT | GAT | GAA | GAT | GAC | CCA | GTG | 873 |
| Ala | Tyr | Trp | Lys | Trp | Asn | Gly | Ser | Val | Ile | Asp | Glu | Asp | Asp | Pro | Val | |
| | | | 260 | | | | | 265 | | | | | 270 | | | |

| CTA | GGG | GAA | GAC | TAT | TAC | AGT | GTG | GAA | AAT | CCT | GCA | AAC | AAA | AGA | AGG | 921 |
| Leu | Gly | Glu | Asp | Tyr | Tyr | Ser | Val | Glu | Asn | Pro | Ala | Asn | Lys | Arg | Arg | |
| | 275 | | | | | 280 | | | | | 285 | | | | | |

-continued

| | | | | | | | | | | | | | | | | |
|---|---|---|---|---|---|---|---|---|---|---|---|---|---|---|---|---|
| AGT | ACC | CTC | ATC | ACA | GTG | CTT | AAT | ATA | TCG | GAA | ATT | GAA | AGT | AGA | TTT | 969 |
| Ser | Thr | Leu | Ile | Thr | Val | Leu | Asn | Ile | Ser | Glu | Ile | Glu | Ser | Arg | Phe | |
| 290 | | | | 295 | | | | | 300 | | | | | 305 | | |
| TAT | AAA | CAT | CCA | TTT | ACC | TGT | TTT | GCC | AAG | AAT | ACA | CAT | GGT | ATA | GAT | 1017 |
| Tyr | Lys | His | Pro | Phe | Thr | Cys | Phe | Ala | Lys | Asn | Thr | His | Gly | Ile | Asp | |
| | | | | 310 | | | | | 315 | | | | | 320 | | |
| GCA | GCA | TAT | ATC | CAG | TTA | ATA | TAT | CCA | GTC | ACT | AAT | TTC | CAG | AAG | CAC | 1065 |
| Ala | Ala | Tyr | Ile | Gln | Leu | Ile | Tyr | Pro | Val | Thr | Asn | Phe | Gln | Lys | His | |
| | | | 325 | | | | | 330 | | | | | 335 | | | |
| ATG | ATT | GGT | ATA | TGT | GTC | ACG | TTG | ACA | GTC | ATA | ATT | GTG | TGT | TCT | GTT | 1113 |
| Met | Ile | Gly | Ile | Cys | Val | Thr | Leu | Thr | Val | Ile | Ile | Val | Cys | Ser | Val | |
| | | | 340 | | | | | 345 | | | | | 350 | | | |
| TTC | ATC | TAT | AAA | ATC | TTC | AAG | ATT | GAC | ATT | GTG | CTT | TGG | TAC | AGG | GAT | 1161 |
| Phe | Ile | Tyr | Lys | Ile | Phe | Lys | Ile | Asp | Ile | Val | Leu | Trp | Tyr | Arg | Asp | |
| | | 355 | | | | | 360 | | | | | 365 | | | | |
| TCC | TGC | TAT | GAT | TTT | CTC | CCA | ATA | AAA | GCT | TCA | GAT | GGA | AAG | ACC | TAT | 1209 |
| Ser | Cys | Tyr | Asp | Phe | Leu | Pro | Ile | Lys | Ala | Ser | Asp | Gly | Lys | Thr | Tyr | |
| 370 | | | | | 375 | | | | | 380 | | | | | 385 | |
| GAC | GCA | TAT | ATA | CTG | TAT | CCA | AAG | ACT | GTT | GGG | GAA | GGG | TCT | ACC | TCT | 1257 |
| Asp | Ala | Tyr | Ile | Leu | Tyr | Pro | Lys | Thr | Val | Gly | Glu | Gly | Ser | Thr | Ser | |
| | | | | 390 | | | | | 395 | | | | | 400 | | |
| GAC | TGT | GAT | ATT | TTT | GTG | TTT | AAA | GTC | TTG | CCT | GAG | GTC | TTG | GAA | AAA | 1305 |
| Asp | Cys | Asp | Ile | Phe | Val | Phe | Lys | Val | Leu | Pro | Glu | Val | Leu | Glu | Lys | |
| | | | 405 | | | | | 410 | | | | | 415 | | | |
| CAG | TGT | GGA | TAT | AAG | CTG | TTC | ATT | TAT | GGA | AGG | GAT | GAC | TAC | GTT | GGG | 1353 |
| Gln | Cys | Gly | Tyr | Lys | Leu | Phe | Ile | Tyr | Gly | Arg | Asp | Asp | Tyr | Val | Gly | |
| | | 420 | | | | | 425 | | | | | 430 | | | | |
| GAA | GAC | ATT | GTT | GAG | GTC | ATT | AAT | GAA | AAC | GTA | AAG | AAA | AGC | AGA | AGA | 1401 |
| Glu | Asp | Ile | Val | Glu | Val | Ile | Asn | Glu | Asn | Val | Lys | Lys | Ser | Arg | Arg | |
| | 435 | | | | | 440 | | | | | 445 | | | | | |
| CTG | ATT | ATC | ATT | TTA | GTC | AGA | GAA | ACA | TCA | GGC | TTC | AGC | TGG | CTG | GGT | 1449 |
| Leu | Ile | Ile | Ile | Leu | Val | Arg | Glu | Thr | Ser | Gly | Phe | Ser | Trp | Leu | Gly | |
| 450 | | | | | 455 | | | | | 460 | | | | | 465 | |
| GGT | TCA | TCT | GAA | GAG | CAA | ATA | GCC | ATG | TAT | AAT | GCT | CTT | GTT | CAG | GAT | 1497 |
| Gly | Ser | Ser | Glu | Glu | Gln | Ile | Ala | Met | Tyr | Asn | Ala | Leu | Val | Gln | Asp | |
| | | | | 470 | | | | | 475 | | | | | 480 | | |
| GGA | ATT | AAA | GTT | GTC | CTG | CTT | GAG | CTG | GAG | AAA | ATC | CAA | GAC | TAT | GAG | 1545 |
| Gly | Ile | Lys | Val | Val | Leu | Leu | Glu | Leu | Glu | Lys | Ile | Gln | Asp | Tyr | Glu | |
| | | | 485 | | | | | 490 | | | | | 495 | | | |
| AAA | ATG | CCA | GAA | TCG | ATT | AAA | TTC | ATT | AAG | CAG | AAA | CAT | GGG | GCT | ATC | 1593 |
| Lys | Met | Pro | Glu | Ser | Ile | Lys | Phe | Ile | Lys | Gln | Lys | His | Gly | Ala | Ile | |
| | | 500 | | | | | 505 | | | | | 510 | | | | |
| CGC | TGG | TCA | GGG | GAC | TTT | ACA | CAG | GGA | CCA | CAG | TCT | GCA | AAG | ACA | AGG | 1641 |
| Arg | Trp | Ser | Gly | Asp | Phe | Thr | Gln | Gly | Pro | Gln | Ser | Ala | Lys | Thr | Arg | |
| | 515 | | | | | 520 | | | | | 525 | | | | | |
| TTC | TGG | AAG | AAT | GTC | AGG | TAC | CAC | ATG | CCA | GTC | CAG | CGA | CGG | TCA | CCT | 1689 |
| Phe | Trp | Lys | Asn | Val | Arg | Tyr | His | Met | Pro | Val | Gln | Arg | Arg | Ser | Pro | |
| 530 | | | | | 535 | | | | | 540 | | | | | 545 | |
| TCA | TCT | AAA | CAC | CAG | TTA | CTG | TCA | CCA | GCC | ACT | AAG | GAG | AAA | CTG | CAA | 1737 |
| Ser | Ser | Lys | His | Gln | Leu | Leu | Ser | Pro | Ala | Thr | Lys | Glu | Lys | Leu | Gln | |
| | | | | 550 | | | | | 555 | | | | | 560 | | |
| AGA | GAG | GCT | CAC | GTG | CCT | CTC | GGG | TAGCATGGA | | | | | | | | 1770 |
| Arg | Glu | Ala | His | Val | Pro | Leu | Gly | | | | | | | | | |
| | | | 565 | | | | 570 | | | | | | | | | |

( 2 ) INFORMATION FOR SEQ ID NO:2:

( i ) SEQUENCE CHARACTERISTICS:
        ( A ) LENGTH: 569 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Lys | Val | Leu | Leu | Arg | Leu | Ile | Cys | Phe | Ile | Ala | Leu | Leu | Ile | Ser |
|---|---|---|---|---|---|---|---|---|---|---|---|---|---|---|---|
| 1 | | | | 5 | | | | | 10 | | | | | 15 | |

| Ser | Leu | Glu | Ala | Asp | Lys | Cys | Lys | Glu | Arg | Glu | Glu | Lys | Ile | Ile | Leu |
|---|---|---|---|---|---|---|---|---|---|---|---|---|---|---|---|
| | | | | 20 | | | | | 25 | | | | | 30 | |

| Val | Ser | Ser | Ala | Asn | Glu | Ile | Asp | Val | Arg | Pro | Cys | Pro | Leu | Asn | Pro |
|---|---|---|---|---|---|---|---|---|---|---|---|---|---|---|---|
| | | 35 | | | | | 40 | | | | | 45 | | | |

| Asn | Glu | His | Lys | Gly | Thr | Ile | Thr | Trp | Tyr | Lys | Asp | Asp | Ser | Lys | Thr |
|---|---|---|---|---|---|---|---|---|---|---|---|---|---|---|---|
| | | 50 | | | | | 55 | | | | | 60 | | | |

| Pro | Val | Ser | Thr | Glu | Gln | Ala | Ser | Arg | Ile | His | Gln | His | Lys | Glu | Lys |
|---|---|---|---|---|---|---|---|---|---|---|---|---|---|---|---|
| 65 | | | | | 70 | | | | | 75 | | | | | 80 |

| Leu | Trp | Phe | Val | Pro | Ala | Lys | Val | Glu | Asp | Ser | Gly | His | Tyr | Tyr | Cys |
|---|---|---|---|---|---|---|---|---|---|---|---|---|---|---|---|
| | | | | 85 | | | | | 90 | | | | | 95 | |

| Val | Val | Arg | Asn | Ser | Ser | Tyr | Cys | Leu | Arg | Ile | Lys | Ile | Ser | Ala | Lys |
|---|---|---|---|---|---|---|---|---|---|---|---|---|---|---|---|
| | | | 100 | | | | | 105 | | | | | 110 | | |

| Phe | Val | Glu | Asn | Glu | Pro | Asn | Leu | Cys | Tyr | Asn | Ala | Gln | Ala | Ile | Phe |
|---|---|---|---|---|---|---|---|---|---|---|---|---|---|---|---|
| | | | 115 | | | | | 120 | | | | | 125 | | |

| Lys | Gln | Lys | Leu | Pro | Val | Ala | Gly | Asp | Gly | Gly | Leu | Val | Cys | Pro | Tyr |
|---|---|---|---|---|---|---|---|---|---|---|---|---|---|---|---|
| | 130 | | | | | 135 | | | | | 140 | | | | |

| Met | Glu | Phe | Phe | Lys | Asn | Glu | Asn | Asn | Glu | Leu | Pro | Lys | Leu | Gln | Trp |
|---|---|---|---|---|---|---|---|---|---|---|---|---|---|---|---|
| 145 | | | | | 150 | | | | | 155 | | | | | 160 |

| Tyr | Lys | Asp | Cys | Lys | Pro | Leu | Leu | Leu | Asp | Asn | Ile | His | Phe | Ser | Gly |
|---|---|---|---|---|---|---|---|---|---|---|---|---|---|---|---|
| | | | | 165 | | | | | 170 | | | | | 175 | |

| Val | Lys | Asp | Arg | Leu | Ile | Val | Met | Asn | Val | Ala | Glu | Lys | His | Arg | Gly |
|---|---|---|---|---|---|---|---|---|---|---|---|---|---|---|---|
| | | | 180 | | | | | 185 | | | | | 190 | | |

| Asn | Tyr | Thr | Cys | His | Ala | Ser | Tyr | Thr | Tyr | Leu | Gly | Lys | Gln | Tyr | Pro |
|---|---|---|---|---|---|---|---|---|---|---|---|---|---|---|---|
| | | 195 | | | | | 200 | | | | | 205 | | | |

| Ile | Thr | Arg | Val | Ile | Glu | Phe | Ile | Thr | Leu | Glu | Glu | Asn | Lys | Pro | Thr |
|---|---|---|---|---|---|---|---|---|---|---|---|---|---|---|---|
| | 210 | | | | | 215 | | | | | 220 | | | | |

| Arg | Pro | Val | Ile | Val | Ser | Pro | Ala | Asn | Glu | Thr | Met | Glu | Val | Asp | Leu |
|---|---|---|---|---|---|---|---|---|---|---|---|---|---|---|---|
| 225 | | | | | 230 | | | | | 235 | | | | | 240 |

| Gly | Ser | Gln | Ile | Gln | Leu | Ile | Cys | Asn | Val | Thr | Gly | Gln | Leu | Ser | Asp |
|---|---|---|---|---|---|---|---|---|---|---|---|---|---|---|---|
| | | | | 245 | | | | | 250 | | | | | 255 | |

| Ile | Ala | Tyr | Trp | Lys | Trp | Asn | Gly | Ser | Val | Ile | Asp | Glu | Asp | Asp | Pro |
|---|---|---|---|---|---|---|---|---|---|---|---|---|---|---|---|
| | | | | 260 | | | | | 265 | | | | | 270 | |

| Val | Leu | Gly | Glu | Asp | Tyr | Tyr | Ser | Val | Glu | Asn | Pro | Ala | Asn | Lys | Arg |
|---|---|---|---|---|---|---|---|---|---|---|---|---|---|---|---|
| | | 275 | | | | | 280 | | | | | 285 | | | |

| Arg | Ser | Thr | Leu | Ile | Thr | Val | Leu | Asn | Ile | Ser | Glu | Ile | Glu | Ser | Arg |
|---|---|---|---|---|---|---|---|---|---|---|---|---|---|---|---|
| | 290 | | | | | 295 | | | | | 300 | | | | |

| Phe | Tyr | Lys | His | Pro | Phe | Thr | Cys | Phe | Ala | Lys | Asn | Thr | His | Gly | Ile |
|---|---|---|---|---|---|---|---|---|---|---|---|---|---|---|---|
| 305 | | | | | 310 | | | | | 315 | | | | | 320 |

| Asp | Ala | Ala | Tyr | Ile | Gln | Leu | Ile | Tyr | Pro | Val | Thr | Asn | Phe | Gln | Lys |
|---|---|---|---|---|---|---|---|---|---|---|---|---|---|---|---|
| | | | | 325 | | | | | 330 | | | | | 335 | |

| His | Met | Ile | Gly | Ile | Cys | Val | Thr | Leu | Thr | Val | Ile | Ile | Val | Cys | Ser |
|---|---|---|---|---|---|---|---|---|---|---|---|---|---|---|---|
| | | | 340 | | | | | 345 | | | | | 350 | | |

| Val | Phe | Ile | Tyr | Lys | Ile | Phe | Lys | Ile | Asp | Ile | Val | Leu | Trp | Tyr | Arg |
|---|---|---|---|---|---|---|---|---|---|---|---|---|---|---|---|
| | | 355 | | | | | 360 | | | | | 365 | | | |

| Asp | Ser | Cys | Tyr | Asp | Phe | Leu | Pro | Ile | Lys | Ala | Ser | Asp | Gly | Lys | Thr |
|---|---|---|---|---|---|---|---|---|---|---|---|---|---|---|---|
| | 370 | | | | | 375 | | | | | 380 | | | | |

| Tyr | Asp | Ala | Tyr | Ile | Leu | Tyr | Pro | Lys | Thr | Val | Gly | Glu | Gly | Ser | Thr |
|---|---|---|---|---|---|---|---|---|---|---|---|---|---|---|---|
| 385 | | | | | 390 | | | | | 395 | | | | | 400 |

```
Ser  Asp  Cys  Asp  Ile  Phe  Val  Phe  Lys  Val  Leu  Pro  Glu  Val  Leu  Glu
               405                      410                      415

Lys  Gln  Cys  Gly  Tyr  Lys  Leu  Phe  Ile  Tyr  Gly  Arg  Asp  Asp  Tyr  Val
               420                      425                 430

Gly  Glu  Asp  Ile  Val  Glu  Val  Ile  Asn  Glu  Asn  Val  Lys  Lys  Ser  Arg
          435                           440                 445

Arg  Leu  Ile  Ile  Ile  Leu  Val  Arg  Glu  Thr  Ser  Gly  Phe  Ser  Trp  Leu
     450                      455                      460

Gly  Gly  Ser  Ser  Glu  Glu  Gln  Ile  Ala  Met  Tyr  Asn  Ala  Leu  Val  Gln
465                      470                      475                      480

Asp  Gly  Ile  Lys  Val  Val  Leu  Leu  Glu  Leu  Glu  Lys  Ile  Gln  Asp  Tyr
                    485                      490                      495

Glu  Lys  Met  Pro  Glu  Ser  Ile  Lys  Phe  Ile  Lys  Gln  Lys  His  Gly  Ala
               500                      505                      510

Ile  Arg  Trp  Ser  Gly  Asp  Phe  Thr  Gln  Gly  Pro  Gln  Ser  Ala  Lys  Thr
               515                      520                 525

Arg  Phe  Trp  Lys  Asn  Val  Arg  Tyr  His  Met  Pro  Val  Gln  Arg  Arg  Ser
     530                      535                      540

Pro  Ser  Ser  Lys  His  Gln  Leu  Leu  Ser  Pro  Ala  Thr  Lys  Glu  Lys  Leu
545                      550                      555                      560

Gln  Arg  Glu  Ala  His  Val  Pro  Leu  Gly
                    565
```

(2) INFORMATION FOR SEQ ID NO:3:

(i) SEQUENCE CHARACTERISTICS:
        (A) LENGTH: 1782 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vii) IMMEDIATE SOURCE:
        (A) LIBRARY: Mouse T-cell cDNA Library
        (B) CLONE: Mouse Interleukin-1 Receptor (ix) FEATURE:
        (A) NAME/KEY: CDS
        (B) LOCATION: 46..1776

(xi) SEQUENCE DESCRIPTION: SEQ ID NO:3:

```
GGATGTCATC  AGAGTTCCCA  GTGCCCCGAA  CCGTGAACAA  CACAA ATG GAG AAT             54
                                                      Met Glu Asn
                                                       1

ATG AAA GTG CTA CTG GGG CTC ATT TGT CTC ATG GTG CCT CTG CTG TCG           102
Met Lys Val Leu Leu Gly Leu Ile Cys Leu Met Val Pro Leu Leu Ser
     5               10                  15

CTG GAG ATT GAC GTA TGT ACA GAA TAT CCA AAT CAG ATC GTT TTG TTT           150
Leu Glu Ile Asp Val Cys Thr Glu Tyr Pro Asn Gln Ile Val Leu Phe
 20              25                  30                      35

TTA TCT GTA AAT GAA ATT GAT ATT CGC AAG TGT CCT CTT ACT CCA AAT           198
Leu Ser Val Asn Glu Ile Asp Ile Arg Lys Cys Pro Leu Thr Pro Asn
             40                  45                  50

AAA ATG CAC GGC GAC ACC ATA ATT TGG TAC AAG AAT GAC AGC AAG ACC           246
Lys Met His Gly Asp Thr Ile Ile Trp Tyr Lys Asn Asp Ser Lys Thr
                 55                  60                  65

CCC ATA TCA GCG GAC CGG GAC TCC AGG ATT CAT CAG CAG AAT GAA CAT           294
Pro Ile Ser Ala Asp Arg Asp Ser Arg Ile His Gln Gln Asn Glu His
```

-continued

```
              70                          75                          80
CTT  TGG  TTT  GTA  CCT  GCC  AAG  GTG  GAG  GAC  TCA  GGA  TAT  TAC  TAT  TGT     342
Leu  Trp  Phe  Val  Pro  Ala  Lys  Val  Glu  Asp  Ser  Gly  Tyr  Tyr  Tyr  Cys
     85                      90                       95

ATA  GTA  AGA  AAC  TCA  ACT  TAC  TGC  CTC  AAA  ACT  AAA  GTA  ACC  GTA  ACT     390
Ile  Val  Arg  Asn  Ser  Thr  Tyr  Cys  Leu  Lys  Thr  Lys  Val  Thr  Val  Thr
100                      105                      110                      115

GTG  TTA  GAG  AAT  GAC  CCT  GGC  TTG  TGT  TAC  AGC  ACA  CAG  GCC  ACC  TTC     438
Val  Leu  Glu  Asn  Asp  Pro  Gly  Leu  Cys  Tyr  Ser  Thr  Gln  Ala  Thr  Phe
                    120                      125                      130

CCA  CAG  CGG  CTC  CAC  ATT  GCC  GGG  GAT  GGA  AGT  CTT  GTG  TGC  CCT  TAT     486
Pro  Gln  Arg  Leu  His  Ile  Ala  Gly  Asp  Gly  Ser  Leu  Val  Cys  Pro  Tyr
               135                      140                      145

GTG  AGT  TAT  TTT  AAA  GAT  GAA  AAT  AAT  GAG  TTA  CCC  GAG  GTC  CAG  TGG     534
Val  Ser  Tyr  Phe  Lys  Asp  Glu  Asn  Asn  Glu  Leu  Pro  Glu  Val  Gln  Trp
          150                      155                      160

TAT  AAG  AAC  TGT  AAA  CCT  CTG  CTT  CTT  GAC  AAC  GTG  AGC  TTC  TTC  GGA     582
Tyr  Lys  Asn  Cys  Lys  Pro  Leu  Leu  Leu  Asp  Asn  Val  Ser  Phe  Phe  Gly
     165                      170                      175

GTA  AAA  GAT  AAA  CTG  TTG  GTG  AGG  AAT  GTG  GCT  GAA  GAG  CAC  AGA  GGG     630
Val  Lys  Asp  Lys  Leu  Leu  Val  Arg  Asn  Val  Ala  Glu  Glu  His  Arg  Gly
180                      185                      190                      195

GAC  TAT  ATA  TGC  CGT  ATG  TCC  TAT  ACG  TTC  CGG  GGG  AAG  CAA  TAT  CCG     678
Asp  Tyr  Ile  Cys  Arg  Met  Ser  Tyr  Thr  Phe  Arg  Gly  Lys  Gln  Tyr  Pro
                    200                      205                      210

GTC  ACA  CGA  GTA  ATA  CAA  TTT  ATC  ACA  ATA  GAT  GAA  AAC  AAG  AGG  GAC     726
Val  Thr  Arg  Val  Ile  Gln  Phe  Ile  Thr  Ile  Asp  Glu  Asn  Lys  Arg  Asp
               215                      220                      225

AGA  CCT  GTT  ATC  CTG  AGC  CCT  CGG  AAT  GAG  ACG  ATC  GAA  GCT  GAC  CCA     774
Arg  Pro  Val  Ile  Leu  Ser  Pro  Arg  Asn  Glu  Thr  Ile  Glu  Ala  Asp  Pro
          230                      235                      240

GGA  TCA  ATG  ATA  CAA  CTG  ATC  TGC  AAC  GTC  ACG  GGC  CAG  TTC  TCA  GAC     822
Gly  Ser  Met  Ile  Gln  Leu  Ile  Cys  Asn  Val  Thr  Gly  Gln  Phe  Ser  Asp
     245                      250                      255

CTT  GTC  TAC  TGG  AAG  TGG  AAT  GGA  TCA  GAA  ATT  GAA  TGG  AAT  GAT  CCA     870
Leu  Val  Tyr  Trp  Lys  Trp  Asn  Gly  Ser  Glu  Ile  Glu  Trp  Asn  Asp  Pro
260                      265                      270                      275

TTT  CTA  GCT  GAA  GAC  TAT  CAA  TTT  GTG  GAA  CAT  CCT  TCA  ACC  AAA  AGA     918
Phe  Leu  Ala  Glu  Asp  Tyr  Gln  Phe  Val  Glu  His  Pro  Ser  Thr  Lys  Arg
                    280                      285                      290

AAA  TAC  ACA  CTC  ATT  ACA  ACA  CTT  AAC  ATT  TCA  GAA  GTT  AAA  AGC  CAG     966
Lys  Tyr  Thr  Leu  Ile  Thr  Thr  Leu  Asn  Ile  Ser  Glu  Val  Lys  Ser  Gln
               295                      300                      305

TTT  TAT  CGC  TAT  CCG  TTT  ATC  TGT  GTT  GTT  AAG  AAC  ACA  AAT  ATT  TTT    1014
Phe  Tyr  Arg  Tyr  Pro  Phe  Ile  Cys  Val  Val  Lys  Asn  Thr  Asn  Ile  Phe
          310                      315                      320

GAG  TCG  GCG  CAT  GTG  CAG  TTA  ATA  TAC  CCA  GTC  CCT  GAC  TTC  AAG  AAT    1062
Glu  Ser  Ala  His  Val  Gln  Leu  Ile  Tyr  Pro  Val  Pro  Asp  Phe  Lys  Asn
     325                      330                      335

TAC  CTC  ATC  GGG  GGC  TTT  ATC  ATC  CTC  ACG  GCT  ACA  ATT  GTA  TGC  TGT    1110
Tyr  Leu  Ile  Gly  Gly  Phe  Ile  Ile  Leu  Thr  Ala  Thr  Ile  Val  Cys  Cys
340                      345                      350                      355

GTG  TGC  ATC  TAT  AAA  GTC  TTC  AAG  GTT  GAC  ATA  GTG  CTT  TGG  TAC  AGG    1158
Val  Cys  Ile  Tyr  Lys  Val  Phe  Lys  Val  Asp  Ile  Val  Leu  Trp  Tyr  Arg
                    360                      365                      370

GAC  TCC  TGC  TCT  GGT  TTT  CTT  CCT  TCA  AAA  GCT  TCA  GAT  GGA  AAG  ACA    1206
Asp  Ser  Cys  Ser  Gly  Phe  Leu  Pro  Ser  Lys  Ala  Ser  Asp  Gly  Lys  Thr
               375                      380                      385

TAC  GAT  GCA  TAT  ATT  CTT  TAT  CCC  AAG  ACC  CTG  GGA  GAG  GGG  TCC  TTC    1254
Tyr  Asp  Ala  Tyr  Ile  Leu  Tyr  Pro  Lys  Thr  Leu  Gly  Glu  Gly  Ser  Phe
```

|     |     |     |     |     | 390 |     |     |     |     | 395 |     |     |     |     | 400 |     |      |
|-----|-----|-----|-----|-----|-----|-----|-----|-----|-----|-----|-----|-----|-----|-----|-----|-----|------|
| TCA | GAC | TTA | GAT | ACT | TTT | GTT | TTT | AAA | CTG | TTG | CCT | GAG | GTC | TTG | GAG |     | 1302 |
| Ser | Asp | Leu | Asp | Thr | Phe | Val | Phe | Lys | Leu | Leu | Pro | Glu | Val | Leu | Glu |     |      |
| 405 |     |     |     |     | 410 |     |     |     |     | 415 |     |     |     |     |     |     |      |

| GGA | CAG | TTT | GGA | TAC | AAG | CTG | TTC | ATT | TAT | GGA | AGG | GAT | GAC | TAT | GTT | 1350 |
|-----|-----|-----|-----|-----|-----|-----|-----|-----|-----|-----|-----|-----|-----|-----|-----|------|
| Gly | Gln | Phe | Gly | Tyr | Lys | Leu | Phe | Ile | Tyr | Gly | Arg | Asp | Asp | Tyr | Val |      |
| 420 |     |     |     |     | 425 |     |     |     |     | 430 |     |     |     |     | 435 |      |

| GGA | GAA | GAT | ACC | ATC | GAG | GTT | ACT | AAT | GAA | AAT | GTA | AAG | AAA | AGC | AGG | 1398 |
|-----|-----|-----|-----|-----|-----|-----|-----|-----|-----|-----|-----|-----|-----|-----|-----|------|
| Gly | Glu | Asp | Thr | Ile | Glu | Val | Thr | Asn | Glu | Asn | Val | Lys | Lys | Ser | Arg |      |
|     |     |     |     | 440 |     |     |     |     | 445 |     |     |     |     | 450 |     |      |

| AGG | CTG | ATT | ATC | ATT | CTA | GTG | AGA | GAT | ATG | GGA | GGC | TTC | AGC | TGG | CTG | 1446 |
|-----|-----|-----|-----|-----|-----|-----|-----|-----|-----|-----|-----|-----|-----|-----|-----|------|
| Arg | Leu | Ile | Ile | Ile | Leu | Val | Arg | Asp | Met | Gly | Gly | Phe | Ser | Trp | Leu |      |
|     |     |     | 455 |     |     |     |     | 460 |     |     |     |     | 465 |     |     |      |

| GGC | CAG | TCA | TCT | GAA | GAG | CAA | ATA | GCC | ATA | TAC | AAT | GCT | CTC | ATC | CAG | 1494 |
|-----|-----|-----|-----|-----|-----|-----|-----|-----|-----|-----|-----|-----|-----|-----|-----|------|
| Gly | Gln | Ser | Ser | Glu | Glu | Gln | Ile | Ala | Ile | Tyr | Asn | Ala | Leu | Ile | Gln |      |
|     |     | 470 |     |     |     |     | 475 |     |     |     |     | 480 |     |     |     |      |

| GAA | GGA | ATT | AAA | ATC | GTC | CTG | CTT | GAG | TTG | GAG | AAA | ATC | CAA | GAC | TAT | 1542 |
|-----|-----|-----|-----|-----|-----|-----|-----|-----|-----|-----|-----|-----|-----|-----|-----|------|
| Glu | Gly | Ile | Lys | Ile | Val | Leu | Leu | Glu | Leu | Glu | Lys | Ile | Gln | Asp | Tyr |      |
|     | 485 |     |     |     |     | 490 |     |     |     |     | 495 |     |     |     |     |      |

| GAG | AAA | ATG | CCA | GAT | TCT | ATT | CAG | TTC | ATT | AAG | CAG | AAA | CAC | GGA | GTC | 1590 |
|-----|-----|-----|-----|-----|-----|-----|-----|-----|-----|-----|-----|-----|-----|-----|-----|------|
| Glu | Lys | Met | Pro | Asp | Ser | Ile | Gln | Phe | Ile | Lys | Gln | Lys | His | Gly | Val |      |
| 500 |     |     |     |     | 505 |     |     |     |     | 510 |     |     |     |     | 515 |      |

| ATT | TGC | TGG | TCA | GGA | GAC | TTT | CAA | GAA | AGA | CCA | CAG | TCT | GCA | AAG | ACC | 1638 |
|-----|-----|-----|-----|-----|-----|-----|-----|-----|-----|-----|-----|-----|-----|-----|-----|------|
| Ile | Cys | Trp | Ser | Gly | Asp | Phe | Gln | Glu | Arg | Pro | Gln | Ser | Ala | Lys | Thr |      |
|     |     |     |     | 520 |     |     |     |     | 525 |     |     |     |     | 530 |     |      |

| AGG | TTC | TGG | AAA | AAC | TTA | AGA | TAC | CAG | ATG | CCA | GCC | CAA | CGG | AGA | TCA | 1686 |
|-----|-----|-----|-----|-----|-----|-----|-----|-----|-----|-----|-----|-----|-----|-----|-----|------|
| Arg | Phe | Trp | Lys | Asn | Leu | Arg | Tyr | Gln | Met | Pro | Ala | Gln | Arg | Arg | Ser |      |
|     |     |     | 535 |     |     |     |     | 540 |     |     |     |     | 545 |     |     |      |

| CCA | TTG | TCT | AAA | CAC | CGC | TTA | CTA | ACC | CTG | GAT | CCT | GTG | CGG | GAC | ACT | 1734 |
|-----|-----|-----|-----|-----|-----|-----|-----|-----|-----|-----|-----|-----|-----|-----|-----|------|
| Pro | Leu | Ser | Lys | His | Arg | Leu | Leu | Thr | Leu | Asp | Pro | Val | Arg | Asp | Thr |      |
|     |     | 550 |     |     |     |     | 555 |     |     |     |     | 560 |     |     |     |      |

| AAG | GAG | AAA | CTG | CCG | GCA | GCA | ACA | CAC | TTA | CCA | CTC | GGC | TAGCATGGC | 1782 |
|-----|-----|-----|-----|-----|-----|-----|-----|-----|-----|-----|-----|-----|-----------|------|
| Lys | Glu | Lys | Leu | Pro | Ala | Ala | Thr | His | Leu | Pro | Leu | Gly |           |      |
|     | 565 |     |     |     |     | 570 |     |     |     |     | 575 |     |           |      |

( 2 ) INFORMATION FOR SEQ ID NO:4:

( i ) SEQUENCE CHARACTERISTICS:
        ( A ) LENGTH: 576 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Glu | Asn | Met | Lys | Val | Leu | Leu | Gly | Leu | Ile | Cys | Leu | Met | Val | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Leu | Ser | Leu | Glu | Ile | Asp | Val | Cys | Thr | Glu | Tyr | Pro | Asn | Gln | Ile |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Val | Leu | Phe | Leu | Ser | Val | Asn | Glu | Ile | Asp | Ile | Arg | Lys | Cys | Pro | Leu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Thr | Pro | Asn | Lys | Met | His | Gly | Asp | Thr | Ile | Ile | Trp | Tyr | Lys | Asn | Asp |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ser | Lys | Thr | Pro | Ile | Ser | Ala | Asp | Arg | Asp | Ser | Arg | Ile | His | Gln | Gln |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Asn | Glu | His | Leu | Trp | Phe | Val | Pro | Ala | Lys | Val | Glu | Asp | Ser | Gly | Tyr |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Tyr | Tyr | Cys | Ile | Val | Arg | Asn | Ser | Thr | Tyr | Cys | Leu | Lys | Thr | Lys | Val |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Thr | Val | Thr | Val | Leu | Glu | Asn | Asp | Pro | Gly | Leu | Cys | Tyr | Ser | Thr | Gln |

-continued

```
                    115                           120                           125
Ala  Thr  Phe  Pro  Gln  Arg  Leu  His  Ile  Ala  Gly  Asp  Gly  Ser  Leu  Val
     130                      135                      140
Cys  Pro  Tyr  Val  Ser  Tyr  Phe  Lys  Asp  Glu  Asn  Asn  Glu  Leu  Pro  Glu
145                      150                      155                      160
Val  Gln  Trp  Tyr  Lys  Asn  Cys  Lys  Pro  Leu  Leu  Asp  Asn  Val  Ser
                    165                      170                      175
Phe  Phe  Gly  Val  Lys  Asp  Lys  Leu  Leu  Val  Arg  Asn  Val  Ala  Glu  Glu
               180                      185                      190
His  Arg  Gly  Asp  Tyr  Ile  Cys  Arg  Met  Ser  Tyr  Thr  Phe  Arg  Gly  Lys
          195                      200                      205
Gln  Tyr  Pro  Val  Thr  Arg  Val  Ile  Gln  Phe  Ile  Thr  Ile  Asp  Glu  Asn
     210                      215                      220
Lys  Arg  Asp  Arg  Pro  Val  Ile  Leu  Ser  Pro  Arg  Asn  Glu  Thr  Ile  Glu
225                      230                      235                      240
Ala  Asp  Pro  Gly  Ser  Met  Ile  Gln  Leu  Ile  Cys  Asn  Val  Thr  Gly  Gln
                    245                      250                      255
Phe  Ser  Asp  Leu  Val  Tyr  Trp  Lys  Trp  Asn  Gly  Ser  Glu  Ile  Glu  Trp
               260                      265                      270
Asn  Asp  Pro  Phe  Leu  Ala  Glu  Asp  Tyr  Gln  Phe  Val  Glu  His  Pro  Ser
          275                      280                      285
Thr  Lys  Arg  Lys  Tyr  Thr  Leu  Ile  Thr  Thr  Leu  Asn  Ile  Ser  Glu  Val
     290                      295                      300
Lys  Ser  Gln  Phe  Tyr  Arg  Tyr  Pro  Phe  Ile  Cys  Val  Val  Lys  Asn  Thr
305                      310                      315                      320
Asn  Ile  Phe  Glu  Ser  Ala  His  Val  Gln  Leu  Ile  Tyr  Pro  Val  Pro  Asp
                    325                      330                      335
Phe  Lys  Asn  Tyr  Leu  Ile  Gly  Gly  Phe  Ile  Ile  Leu  Thr  Ala  Thr  Ile
               340                      345                      350
Val  Cys  Cys  Val  Cys  Ile  Tyr  Lys  Val  Phe  Lys  Val  Asp  Ile  Val  Leu
          355                      360                      365
Trp  Tyr  Arg  Asp  Ser  Cys  Ser  Gly  Phe  Leu  Pro  Ser  Lys  Ala  Ser  Asp
     370                      375                      380
Gly  Lys  Thr  Tyr  Asp  Ala  Tyr  Ile  Leu  Tyr  Pro  Lys  Thr  Leu  Gly  Glu
385                      390                      395                      400
Gly  Ser  Phe  Ser  Asp  Leu  Asp  Thr  Phe  Val  Phe  Lys  Leu  Leu  Pro  Glu
                    405                      410                      415
Val  Leu  Glu  Gly  Gln  Phe  Gly  Tyr  Lys  Leu  Phe  Ile  Tyr  Gly  Arg  Asp
               420                      425                      430
Asp  Tyr  Val  Gly  Glu  Asp  Thr  Ile  Glu  Val  Thr  Asn  Glu  Asn  Val  Lys
          435                      440                      445
Lys  Ser  Arg  Arg  Leu  Ile  Ile  Ile  Leu  Val  Arg  Asp  Met  Gly  Gly  Phe
     450                      455                      460
Ser  Trp  Leu  Gly  Gln  Ser  Ser  Glu  Glu  Gln  Ile  Ala  Ile  Tyr  Asn  Ala
465                      470                      475                      480
Leu  Ile  Gln  Glu  Gly  Ile  Lys  Ile  Val  Leu  Leu  Glu  Leu  Glu  Lys  Ile
                    485                      490                      495
Gln  Asp  Tyr  Glu  Lys  Met  Pro  Asp  Ser  Ile  Gln  Phe  Ile  Lys  Gln  Lys
               500                      505                      510
His  Gly  Val  Ile  Cys  Trp  Ser  Gly  Asp  Phe  Gln  Glu  Arg  Pro  Gln  Ser
          515                      520                      525
Ala  Lys  Thr  Arg  Phe  Trp  Lys  Asn  Leu  Arg  Tyr  Gln  Met  Pro  Ala  Gln
     530                      535                      540
```

-continued

| Arg | Arg | Ser | Pro | Leu | Ser | Lys | His | Arg | Leu | Leu | Thr | Leu | Asp | Pro | Val |
|-----|-----|-----|-----|-----|-----|-----|-----|-----|-----|-----|-----|-----|-----|-----|-----|
| 545 |     |     |     |     | 550 |     |     |     |     | 555 |     |     |     |     | 560 |

| Arg | Asp | Thr | Lys | Glu | Lys | Leu | Pro | Ala | Ala | Thr | His | Leu | Pro | Leu | Gly |
|-----|-----|-----|-----|-----|-----|-----|-----|-----|-----|-----|-----|-----|-----|-----|-----|
|     |     |     |     | 565 |     |     |     |     | 570 |     |     |     |     | 575 |     |

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: Primer Oligonuleotide to 5'Leader Sequence of
            IL-1 Receptor ( x i ) SEQUENCE DESCRIPTION: SEQ ID NO:5:

GCGGATCCCC TCCTGAGAAG CT                      22

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: Primer Oligonucleotide Upstream of
            Transmembrane Portion of ( x i ) SEQUENCE DESCRIPTION: SEQ ID NO:6:

GCGGATCCCA TGTGCTACTG G                       21